(12) United States Patent
Ramadass et al.

(10) Patent No.: US 11,795,496 B2
(45) Date of Patent: Oct. 24, 2023

(54) EPIGENETIC CHROMOSOME INTERACTIONS

(71) Applicant: Oxford Biodynamics PLC, Oxford (GB)

(72) Inventors: Aroul Ramadass, Oxford (GB); Ewan Hunter, Oxford (GB); Alexandre Akoulitchev, Oxford (GB)

(73) Assignee: Oxford Biodynamics PLC, Oxford (GB)

( * ) Notice: Subject to any disclaimer, the term of this patent is extended or adjusted under 35 U.S.C. 154(b) by 546 days.

(21) Appl. No.: 15/738,457

(22) PCT Filed: Jun. 24, 2016

(86) PCT No.: PCT/GB2016/051894
§ 371 (c)(1),
(2) Date: Dec. 20, 2017

(87) PCT Pub. No.: WO2016/207647
PCT Pub. Date: Dec. 29, 2016

(65) Prior Publication Data
US 2019/0071715 A1    Mar. 7, 2019

(30) Foreign Application Priority Data

Jun. 24, 2015  (GB) .................................. 1511079
Jun. 24, 2015  (GB) .................................. 1511080
Nov. 5, 2015   (GB) .................................. 1519555

(51) Int. Cl.
| C12Q 1/68 | (2018.01) |
| C12Q 1/6827 | (2018.01) |
| C12Q 1/6883 | (2018.01) |
| C12Q 1/6886 | (2018.01) |
| G16H 50/70 | (2018.01) |
| G16B 40/00 | (2019.01) |

(52) U.S. Cl.
CPC ......... *C12Q 1/6827* (2013.01); *C12Q 1/6883* (2013.01); *C12Q 1/6886* (2013.01); *G16B 40/00* (2019.02); *G16H 50/70* (2018.01); *C12Q 2521/501* (2013.01); *C12Q 2523/101* (2013.01); *C12Q 2537/159* (2013.01); *C12Q 2600/106* (2013.01)

(58) Field of Classification Search
CPC ......................................................... C12Q 1/68
See application file for complete search history.

(56) References Cited

U.S. PATENT DOCUMENTS

| 10,508,303 B2 * | 12/2019 | Ren ....................... C12Q 1/6874 |
| 2007/0238094 A1 | 10/2007 | Chaussabel et al. |
| 2010/0075861 A1 * | 3/2010 | De Laat ................... A61P 43/00 506/26 |
| 2010/0130373 A1 | 5/2010 | Dekker et al. |
| 2018/0274015 A1 | 9/2018 | Akoulitchev et al. |

FOREIGN PATENT DOCUMENTS

| WO | 2005/118873 A2 | 12/2005 |
| WO | 2007/093819 A2 | 8/2007 |
| WO | 2008/084405 A2 | 7/2008 |
| WO | 2009/147386 A1 | 12/2009 |
| WO | WO-2009147386 A1 * | 12/2009 ......... A61K 31/7088 |
| WO | 2012/159025 A2 | 11/2012 |
| WO | 2015/077414 A1 | 5/2015 |

OTHER PUBLICATIONS

Plant et al. Genetic and epigenetic predictors of responsiveness to treatment in RA. Nature Reviews Rheumatology; 2014; 10; 6: 329-337. (Year: 2014).*
Cobb et al. Genome-wide data reveal novel genes for methotrexate response in a large cohort of juvenile idiopathic arthritis cases. The Pharmacogenomics Journal; 2014; 14: 356-364. (Year: 2014).*
Plant et al. Genetic and epigenetic predictors of responsiveness to treatment in RA. Rheumatology; 2014; 10: 329-337 (Review). (Year: 2014).*
Crutchley et al. Chromatin conformation signatures: ideal human disease biomarkers. Biomarkers Med.; 2010; 4(4): 611-629 (Review). (Year: 2010).*
Li et al. Extensive Promoter-Centered Chromatin Interactions Provide a Topological Basis for Transcription Regulation. Cell; 2012; 148: 84-98. (Year: 2012).*
Sandhu et al. Large-Scale Functional Organization of Long-Range Chromatin Interaction Networks. Cell Rep.; 2012; 2(5): 1207-1219. (Year: 2012).*
Fullwood et al. An oestrogen-receptor-a-bound human chromatin interactome. Nature; 2009; 462: 58-64. (Year: 2009).*
Crutchley et al. Biomarkers Med.; 2010; 4(4): 611-629 (Review). (Year: 2010).*
Plant et al. Rheumatology; 2014;10: 329-337 (Review). (Year: 2014).*
Sandhu et al. Cell Rep.; 2012; 2(5): 1207-1219. (Year: 2012).*
Fullwood et al., Nature; 2009; 462: 58-64. (Year: 2009).*
Youdell, M., et al., "Development of Novel ALS Treatment on the Basis of Mechanisms of Cellular Chronological Life Span Control," Poster at the 12th annual Northeast ALS Consortium (NEALS); Oct. 7, 2013. Exhibit A—document providing enlarged sections of poster.
Brites, N. and Vaz, A.R., "Microglia centered pathogenesis in ALS: insights in cell interconnectivity," Frontiers in Cellular Neuroscience, 8(Article 117): 1-24 (2014).
Fontana, L., et al., "Extending Healthy Life Span—From Yeast to Humans," Science, 328: (5976), 321-326 (2010).
Bastonini, E., et al., "Chromatin barcodes as biomarkers for melanoma," Pigment Cell Melanoma Res., 27: 788-800 (2014).
Alshaker, H., et al., "Development of a new epigenetic-based blood test to stratify prostate cancer patients according to risk groups," International Journal of Molecular Medicine, 34 (Suppl S9) (2014).
Sun, J., et al., "A Novel Suppressive Long Noncoding RNA within the IGF1R Gene Locus Is Imprinted in Acute Myelocytic Leukemia," Blood, 124(21): p. 3592 (2014). Retrieved from the internet May 21, 2020. <<https://ashpublications.org/blood/article/124/21/3592/97498/A-Novel-Suppressive-Long-Noncoding-RNA-within-the?searcresult=1>>.

(Continued)

*Primary Examiner* — Ethan C Whisenant
(74) *Attorney, Agent, or Firm* — Elmore Patent Law Group, P.C.; Joseph C. Zucchero; Carolyn S. Elmore

(57) ABSTRACT

A method of determining responsiveness to therapy for rheumatoid arthritis.

1 Claim, 9 Drawing Sheets

Specification includes a Sequence Listing.

(56) References Cited

OTHER PUBLICATIONS

Oxford BioDynamics Website (2013-2014) http://web.archive.org/web/20131209081232/http://oxfordbiodynamics.com/applications/predictive-biomarkers.

Kubiak, M., et al., "Can chromatin conformation technologies bring light into human molecular pathology?" Acta Biochimica Polonica, 62(3): 483-489 (2015).

Mukhopadhyay, S., et al., "Formation of distinct chromatin conformation signatures epigenetically regulate macrophage activation," Intl. Immunopharmacol., 18: 7-11 (2013).

Cheng, J. X., et al., "Disease-Associated Chromatin Conformation and Therapeutic Implications In Leukemia," Blood, 122(21): 4892 (2013).

Jakub, J. W., et al., "A pilot study of chromosomal aberrations and epigenetic changes in peripheral blood samples to identify patients with melanoma," Melanoma Research, 25: 406-411 (2015).

Carini, et al., "Epigenetic Chromosome Conformations Predict MTX Responsiveness in Early Rheumatoid Arthritis Patients", Annual Meeting of the American-College-of-Rheumatology (ACR) and Association-of-Rheumatology-Health; San Francisco, CA, USA; 2015, vol. 67, Suppl. 10. Retrieved from the Internet: URL:http://acrabstracts.org/abstract/epigenetic-chromosome-conformations-predict-mtx-responsiveness-in-early-rheumatoid-arthritis-patients/ [retrieved on Sep. 8, 2016].

Jakub, J. W. et al., "Diagnostic Value of Epigenetic Chromatin Conformation Changes Identified in Peripheral Blood to Differentiate Early Stage Melanoma From Healthy Volunteers and Other Cutaneous Malignancies," WSA 2013 Annual Scientific Session, 2013.

Crutchley, J., et al., "Chromatin conformation signatures: ideal human disease biomarkers?", Biomarkers in Medicine, vol. 4, No. 4, Aug. 1, 2010 (Aug. 1, 2010), pp. 611-629.

Byers, R. J., et al., "Subtractive hybridization: Genetic takeaways and the search for meaning", International Review of Experimental Pathology, Blackwell Scientific, Oxford, GB, vol. 81, No. 6, pp. 391-404 (2000).

Ranganathan, P., et al., "Will pharmacogenetics allow better prediction of methotrexate toxicity and efficacy in patients with rheumatoid arthritis?" Annals of the Rheumatic Diseases, British Medical Association, GB, vol. 62, No. 1, Jan. 1, 2003 (Jan. 1, 2003), pp. 4-9.

Plant, D., et al., "Genetic and epigenetic predictors of responsiveness to treatment in RA," Nature Reviews, Rheumatology, vol. 10, No. 6, Jun. 1, 2014 (Jun. 1, 2014).

Wessels, J., et al., "A clinical pharmacogenetic model to predict the efficacy of methotrexate monotherapy in recent-onset rheumatoid arthritis", Arthritis & Rheumatism, vol. 56, No. 6, Jun. 1, 2007 (Jun. 1, 2007), pp. 1765-1775.

Martin, P., et al., "Capture Hi-C reveals novel candidate genes and complex long-range interactions with related autoimmune risk loci", Nature Communications, vol. 6(10069), www.nature.com/naturecommunications, Nov. 30, 2015 (Nov. 30, 2015).

Verlaan, D. J., et al., "Allele-Specific Chromatin Remodeling in the ZPBP2/GSDMB/ORMDL3 Locus Associated with the Risk of Asthma and Autoimmune Disease," The American Journal of Human Genetics, 85, 377-393 (2009).

Shulha, H. P., et al., "Human-Specific Histone Methylation Signatures at Transcription Start Sites in Prefrontal Neurons", PLoS Biol 10(11): e1001427.

McCord, R., et al., "Chromatin signatures of DLBCL subtypes" [abstract] in: Proceedings of the 105th Annual Meeting of the American Association for Cancer Research; Apr. 5-9, 2014; San Diego, CA. Philadelphia (PA): AACR; Cancer Research 2014;74(19 Suppl):Abstract 462. doi:10.1158/1538-7445.AM2014-462 [retrieved Aug. 20, 2018] <URL: http://cancerres.aacrjournals.org/content/74/19_Supplement/462.

Wikipedia, "Chromosoma conformation capture" as at Apr. 28, 2014 [retrieved Aug. 20, 2018] <URL: https://en.wikipedia.org/w/index.php?title=Chromosome_conformation_capture&oldid=606170436.

Wang, S., et al., "Disease mechanisms in rheumatology—tools and pathways: defining functional genetic variants in autoimmune diseases", Arthritis and Rheumatology, 67(1): 1-10 (2015).

Xu, Z., et al., "Mapping of long-range INS promoter interactions reveals a role for calcium-activated chloride channel ANO1 in insulin secretion", PNAS, 111(47): 16760-16765 (2014).

Dekker, J., et al., "Capturing chromosome conformation", Science, 295: 1306-1311 (2002).

Mitchell, R. M., "A CSF biomarker panel for identification of patients with amyotrophic lateral sclerosis", Neurology, 72(1): 14-19, (2009). Epub Nov. 5, 2008.

Mitchell, R. M., "Plasma biomarkers associated with ALS and their relationship to iron homeostasis", Muscle Nerve, 42:95-103 (2010).

Woollacott, I. O. C., et al., "The C9ORF72 expansion mutation: gene structure, phenotypic and diagnostic issues", Acta Neuropathol., 127(3): 319-332 (2014).

Salter, M., et al., "Initial Identification of a Blood-Based Chromosome Conformation Signature for Aiding in the Diagnosis of Amyotrophic Lateral Sclerosis.", EBioMedicine, 33: 169-184 (2018). doi: 10.1016/j.ebiom.2018.06.015. Epub Jun. 23, 2018.

Goodyear, C., et al., "Epigenetic Chromosome Conformations Predict MTX Responsiveness in Early Rheumatoid Arthritis Patients". Presentation made at ACR/ARHP Annual Meeting (Nov. 6-11, 2015 in San Francisco, CA).

Liao, K. P., et al., "Environmental influences on risk for rheumatoid arthritis," Curr. Opin. Rheumatol., 21: 279-283 (2009).

Bottini, N., et al., "Epigenetics in rheumatoid arthritis: a primer for rheumatologists," Curr. Rheumatol. Rep., 15, 372 (2013).

McInnes, I. B., et al., "The pathogenesis of rheumatoid arthritis," N. Engl. J. Med., 365(23): 2205-2219 (2011).

Liu, Y., et al., "Epigenome-wide association data implicate DNA methylation as an intermediary of genetic risk in rheumatoid arthritis," Nat. Biotechnol., 31(2): 142-147 (2013).

Nakano, K., et al., "DNA methylome signature in rheumatoid arthritis," Ann. Rheum. Dis., 72(1): 110-117 (2013).

De La Rica, L., et al., "Identification of novel markers in rheumatoid arthritis through integrated analysis of DNA methylation and microRNA expression," J. Autoimmun., 41: 6-16 (2013).

Matte, S., et al., Genetics and epigenetics of rheumatoid arthritis, Nat. Rev. Rheumatol., 9(3): 141-153 (2013).

Hider, S. L., et al., "Can clinical factors at presentation be used to predict outcome of treatment with methotrexate in patients with early inflammatory polyarthritis?" Ann. Rheum. Dis., 68: 57-62 (2009).

Farragher, T. M., et al., "Early treatment with, and time receiving, first disease-modifying antirheumatic drug predicts long-term function in patients with inflammatory polyarthritis," Ann. Rheum. Dis., 69: 689-695 (2010).

Bakker, M. F., et al., "Early clinical response to treatment predicts 5-year outcome in RA patients: follow-up results from the CAMERA study," Ann. Rheum. Dis., 70: 1099-1103 (2011).

Barrera, P., et al., "Drug survival, efficacy and toxicity of monotherapy with a fully human anti-tumour necrosis factor-$\alpha$ antibody compared with methotrexate in long-standing rheumatoid arthritis," Rheumatology, 41: 430-439 (2002).

Deng, W., et al., "Do chromatin loops provide epigenetic gene expression states?" Curr. Opin. Genet. Dev., 20(5): 548-54 (2010).

Kadauke, S., et al, "Chromatin loops in gene regulation," Biochim Biophys Acta., 1789(1): 17-25 (2009).

Christova, R., et al., "P-STAT1 mediates higher-order chromatin remodelling of the human MHC in response to IFN$\gamma$," J. Cell Sci., 120(18): 3262-3270 (2007).

Watanabe, T., et al., "Higher-Order Chromatin Regulation and Differential Gene Expression in the Human Tumour Necrosis Factor/Lymphotoxin Locus in Hepatocellular Carcinoma Cells," Mol. Cell. Biol., 32: 1529-1541 (2012).

Harismendy, O., et al., "9p21 DNA variants associated with coronary artery disease impair interferon-$\gamma$ signalling response," Nature, 470(11): 264-268 (2011).

(56) References Cited

OTHER PUBLICATIONS

Rau, R., et al., "Benefit and risk of methotrexate treatment in rheumatoid arthritis," Clin. Exp. Rheumatol., 22: S83-S94 (2004).
Kosaka, N., et al., "Unraveling the Mystery of Cancer by Secretory micro RNA: Horizontal microRNA Transfer between Living Cells," Front. in Genet., 2: 97 (2011).
Rozen, S., et al., "Primer3 on the WWW for general users and for biologist programmers," Methods Mol Biol., 132: 365-386 (2000).
Hunter, E., et al., U.S. Appl. No. 15/738,476, filed May 23, 2018.
Figueroa-Romero, C. et al., "Identification of Epigenetically Altered Genes in Sporadic Amyotrophic Lateral Sclerosis", PLOS One, vol. 7, No. 12, e52672, Dec. 2012.
"Amyotrophic Lateral Sclerosis (ALS) patients could benefit from a new tool being developed by Oxford Biodynamics partly funded by the UK government," Press Release From Oxford BioDynamics of Dec. 16, 2014.
"Biotechnology firm Oxford BioDynamics earns Technology Innovation Award for biomarker discovery platform EpiSwitch™," Press Release From Oxford BioDynamics of Oct. 22, 2015.
Press Release of Jun. 2, 2016: Oxford BioDynamics picks Malaysia to conduct a biomarker discovery programme for diabetes and pre-diabetes.
Press Releases from Oxford BioDynamics from Aug. 10, 2009 to Apr. 25, 2016.
Tests look at the development of type 2 diabetes to predict the progress of the condition; The Diabetes Research & Wellness Foundation, Apr. 21, 2016.
Development of Novel ALS Treatment on the Basis of Mechanisms of Cellular Chronological Life Span Control; Poster at the 12th annual Northeast ALS Consortium (NEALS), Oct. 7, 2013.
Babu, D., et al., "3D Genome Organization in Health And Disease: Emerging Opportunities In Cancer Translational Medicine", Nucleus 6:5, Sep./Oct. 2015, 382-393.
Biotechnology firm Oxford BioDynamics expands its biomarker discovery programme for ALS diagnosis; International Pharmaceutical Industry (IPI); Jan. 15, 2016. http:<<www.ipimediaworld.com/biotechnology-firm-oxford-biodynamics-expands-its-biomarker-discovery-programme-for-als-diagnosis/>>.
Hunter, E., et al., "Development of Epigenetic Profiling of ALS Patients with Chromosome Conformation Biomarkers Offers Novel Signatures for Non-invasive Diagnostic and Prognostic Stratifications", Annual 2015 ALS Consortium Conference in Tampa, Florida, Nov. 6, 2015.
Williams, M. T., et al., "Fcg Receptor Targeting Reduces Bone Disease in a Pre-clinical Model of Multiple Myeloma", 57th American Society of Hematology Meeting in Orlando, Dec. 9, 2015.
"New Frontiers in Epigenetics: Genomic Biomarkers with EpiSwitchTM Technology", OBD presentation at SingHealth, National Cancer Centre, Singapore (NCCS), Jan. 23, 2012, 1-7.
Akoulitchev, A. "Clinical evaluation of EpiSwitch OBD-27, a Breast Cancer Screening Tool, based on Epigenetics Concept on Japanese population", Chinese language Abstract O-065. Annual Meeting of Japanese Association of Breast Cancer Screening, Okinawa, Nov. 30, 2012.
Akoulitchev, A. et al., "Clinical evaluation of EpiSwitch OBD-27, a Breast Cancer Screening Tool, based on Epigenetics Concept on Japanese population", English translation of D68 [Abstract O-065. Annual Meeting of Japanese Association of Breast Cancer Screening, Okinawa, Nov. 30, 2012.
Akoulitchev, A. "Epigenetics and New Approaches in Molecular Diagnosis", CMR Seminar Announcement poster at SingHealth, Jan. 23, 2012.
Hughes, E. "Oxford BioDynamics expands biomarker discovery programme for ALS", EPM Magazine; Jan. 28, 2016. <<https://www.epmmagazine.com/news/oxford-biodynamics-expands-biomarker-discovery-programme-for/ >>.
Jeznach, M. et al., "Breast cancer: development of early non-invasive diagnostics to reduce disease mortality and psychological outcomes", Psychoonkologia, vol. 2, 2013, 35-49.
Jeznach, M. "Systemic Epigenetic Biomarkers for ALS Improve Early Diagnosis, Treatment and Trials", International Pharmaceutical Industry Magazine, vol. 8 Issue 1, Spring 2016.
Pchejetski, D. et al., "Validation of a New Epigenetic-Based Prognostic Blood Test to Predict Prostate Cancer Aggressiveness", Annals of Oncology, 24 (Supplement 9): ix31-ix65, 2013.
Campus Internal Grant Report (Academics year 2010-11). Journal of Saitama Medical University, 2012, vol. 39, No. 1, p. 4-8.
Goodyear, C., et al., "Epigenetic Chromosome Conformations Predict MTX Responsiveness in Early Rheumatoid Arthritis Patients". Presentation made at ACR/ARHP Annual Meeting (Nov. 6-11, 2015 in San Francisco, CA), publicly disclosed earlier on Mar. 31, 2014 at 'The Scottish Early Rheumatoid Arthritis (SERA) Meeting' in Perth, Scotland.
Imakaev, M. et al., "Iterative Correction of Hi-C Data Reveals Hallmarks of Chromosome Organization", Nature Methods, vol. 9, No. 10, Oct. 2012, 999-1003.
Lajoie, B. et al., "The Hitchhiker's Guide to Hi-C Analysis: Practical Guidelines", Methods, vol. 72, 2015, 65-75.

\* cited by examiner

SEQUENCE LISTING

<160> NUMBER OF SEQ ID NOS: 152

<210> SEQ ID NO 1
<211> LENGTH: 60
<212> TYPE: DNA
<213> ORGANISM: Homo sapiens

<400> SEQUENCE: 1
tgttttttgg ctgcataaat gtcttctttc gaataatca tcaaaatatt tttcattgac    60

<210> SEQ ID NO 2
<211> LENGTH: 60
<212> TYPE: DNA
<213> ORGANISM: Homo sapiens

```
<400> SEQUENCE: 2 caccccatc tccctttgct gactctcttc gatgaatcca ttttttgga aatagatgat    60

<210> SEQ ID NO 3
<211> LENGTH: 60
<212> TYPE: DNA
<213> ORGANISM: Homo sapiens

<400> SEQUENCE: 3 caccccatc tccctttgct gactctcttc gaactgtggc aattttaact tttcaaattg    60

<210> SEQ ID NO 4
<211> LENGTH: 60
<212> TYPE: DNA
<213> ORGANISM: Homo sapiens

<400> SEQUENCE: 4 caccccatc tccctttgct gactctcttc gaggcatgat ttgagtcttg acagaagttc    60

<210> SEQ ID NO 5
<211> LENGTH: 60
<212> TYPE: DNA
<213> ORGANISM: Homo sapiens

<400> SEQUENCE: 5
tgccagtatt ttattgagga tttttgcatc gagattgggt tgcatcatgt tggccaggct    60

<210> SEQ ID NO 6
<211> LENGTH: 60
<212> TYPE: DNA
<213> ORGANISM: Homo sapiens

<400> SEQUENCE: 6
tgttttttgg ctgcataaat gtcttctttc gaactcatgg gcacaagcaa tcctcccacc    60

<210> SEQ ID NO 7
<211> LENGTH: 60
<212> TYPE: DNA
<213> ORGANISM: Homo sapiens

<400> SEQUENCE: 7
tgccagtatt ttattgagga tttttgcatc gaacagatgg agggaagagg ggatagctcc    60

<210> SEQ ID NO 8
<211> LENGTH: 60
<212> TYPE: DNA
<213> ORGANISM: Homo sapiens

<400> SEQUENCE: 8
tgccctagag atctgtggaa ctttgaactc gagtcaaaga gatatcaaga gcttctatca    60

<210> SEQ ID NO 9
<211> LENGTH: 60
<212> TYPE: DNA
<213> ORGANISM: Homo sapiens

<400> SEQUENCE: 9 caccccatc tccctttgct gactctcttc gagggcagaa tgagcctcag acatctccag    60

<210> SEQ ID NO 10
<211> LENGTH: 60
<212> TYPE: DNA
<213> ORGANISM: Homo sapiens
```

```
<400> SEQUENCE: 10
tctcctgcct gattgccctg ccagaacttc gatttgggct atagtgttgt tccagtctaa    60

<210> SEQ ID NO 11
<211> LENGTH: 60
<212> TYPE: DNA
<213> ORGANISM: Homo sapiens

<400> SEQUENCE: 11 caccccatc tcctttgct gactctcttc gatcttgaag agatctcttc ttagcaaagc     60

<210> SEQ ID NO 12
<211> LENGTH: 60
<212> TYPE: DNA
<213> ORGANISM: Homo sapiens

<400> SEQUENCE: 12 caccccatc tcctttgct gactctcttc gaaatatttt tgcttgagct cctgtctcat    60

<210> SEQ ID NO 13
<211> LENGTH: 60
<212> TYPE: DNA
<213> ORGANISM: Homo sapiens

<400> SEQUENCE: 13
taggcgcaca tgcacacagc tcgcctcttc gacccaggaa gatccaaagg aggaactgag    60

<210> SEQ ID NO 14
<211> LENGTH: 60
<212> TYPE: DNA
<213> ORGANISM: Homo sapiens

<400> SEQUENCE: 14
cccccacccc catcccagga aattggtttc gatgagagaa ggcaagagaa catgggtct    60

<210> SEQ ID NO 15
<211> LENGTH: 60
<212> TYPE: DNA
<213> ORGANISM: Homo sapiens

<400> SEQUENCE: 15
tgccagtatt ttattgagga ttttttgcatc gagttcaaag ttccacagat ctctagggca    60

<210> SEQ ID NO 16
<211> LENGTH: 60
<212> TYPE: DNA
<213> ORGANISM: Homo sapiens

<400> SEQUENCE: 16
ctaaaaatta catccaggaa atgagatatc gaaagaagac atttatgcag ccaaaaaaca    60

<210> SEQ ID NO 17
<211> LENGTH: 60
<212> TYPE: DNA
<213> ORGANISM: Homo sapiens

<400> SEQUENCE: 17
taggcgcaca tgcacacagc tcgcctcttc gatgtacaag ctgcctattg atagactttc    60

<210> SEQ ID NO 18
<211> LENGTH: 60
<212> TYPE: DNA
<213> ORGANISM: Homo sapiens
```

<400> SEQUENCE: 18
aaagttgtgc aatcaggcaa gtcaagattc gaaagaagac atttatgcag ccaaaaaaca    60

<210> SEQ ID NO 19
<211> LENGTH: 60
<212> TYPE: DNA
<213> ORGANISM: Homo sapiens

<400> SEQUENCE: 19 caccccatc tccctttgct gactctcttc gagtggtgag cagccaaacc agggttcact    60

<210> SEQ ID NO 20
<211> LENGTH: 60
<212> TYPE: DNA
<213> ORGANISM: Homo sapiens

<400> SEQUENCE: 20
gggtcttgct atgttgccca ggctggcctc gagatcagcc tgggcaacac ggtgaaaacc    60

<210> SEQ ID NO 21
<211> LENGTH: 60
<212> TYPE: DNA
<213> ORGANISM: Homo sapiens

<400> SEQUENCE: 21
ctggtttagt cttgggagag tgtatgtgtc gagttaagcc atctgcaaat agcaagagag    60

<210> SEQ ID NO 22
<211> LENGTH: 60
<212> TYPE: DNA
<213> ORGANISM: Homo sapiens

<400> SEQUENCE: 22
agccttgcat cccagggatg aagcccactc gagatataga ttgagcccca gttttggag    60

<210> SEQ ID NO 23
<211> LENGTH: 60
<212> TYPE: DNA
<213> ORGANISM: Homo sapiens

<400> SEQUENCE: 23
atcgtgtggg ctgtgtgtgg cagactgttc gaaatcggaa gcctctctga aggtccaagg    60

<210> SEQ ID NO 24
<211> LENGTH: 60
<212> TYPE: DNA
<213> ORGANISM: Homo sapiens

<400> SEQUENCE: 24
tgccagtatt ttattgagga tttttgcatc gaattcctgg gtttatatcc caatcattgt    60

<210> SEQ ID NO 25
<211> LENGTH: 60
<212> TYPE: DNA
<213> ORGANISM: Homo sapiens

<400> SEQUENCE: 25 caccccatc tccctttgct gactctcttc gatattggtg tatattcaaa gggtacttga    60

<210> SEQ ID NO 26
<211> LENGTH: 60
<212> TYPE: DNA
<213> ORGANISM: Homo sapiens

<400> SEQUENCE: 26
tgatcactgt tccctatgag gatacagctc gaggggcagg gggcggtcct gggccaggcg      60

<210> SEQ ID NO 27
<211> LENGTH: 60
<212> TYPE: DNA
<213> ORGANISM: Homo sapiens

<400> SEQUENCE: 27
aacttatgat tctaatcttg aatgtctgtc gatctatgag gaaatgcccc cagcctccca      60

<210> SEQ ID NO 28
<211> LENGTH: 60
<212> TYPE: DNA
<213> ORGANISM: Homo sapiens

<400> SEQUENCE: 28
cataatgcat gtgcatgaaa actaatcttc gatctatgag gaaatgcccc cagcctccca      60

<210> SEQ ID NO 29
<211> LENGTH: 60
<212> TYPE: DNA
<213> ORGANISM: Homo sapiens

<400> SEQUENCE: 29
atcagtaagc tggtcagcta cccatgaatc gatctatgag gaaatgcccc cagcctccca      60

<210> SEQ ID NO 30
<211> LENGTH: 60
<212> TYPE: DNA
<213> ORGANISM: Homo sapiens

<400> SEQUENCE: 30
gtgtcccaat ttctagtgca ctgtgaactc gacctcgcgg gaggggtgcc aggccgcatc      60

<210> SEQ ID NO 31
<211> LENGTH: 60
<212> TYPE: DNA
<213> ORGANISM: Homo sapiens

<400> SEQUENCE: 31
ccggggcttc tcgtttaaga attctttgtc gatctatgag gaaatgcccc cagcctccca      60

<210> SEQ ID NO 32
<211> LENGTH: 60
<212> TYPE: DNA
<213> ORGANISM: Homo sapiens

<400> SEQUENCE: 32
gtctttgaag aaggactaat gcttagtatc gagtgcagcg ccggtgggcc agcactgctg      60

<210> SEQ ID NO 33
<211> LENGTH: 60
<212> TYPE: DNA
<213> ORGANISM: Homo sapiens

<400> SEQUENCE: 33
gttcatttaa acattttatt atgtatattc gaggggccag gcttttatac ccccatctga      60

<210> SEQ ID NO 34
<211> LENGTH: 60
<212> TYPE: DNA
<213> ORGANISM: Homo sapiens

```
<400> SEQUENCE: 34
ttctccacag ccggccggtc cttggcagtc gaggggcagg gggcggtcct gggccaggcg        60

<210> SEQ ID NO 35
<211> LENGTH: 60
<212> TYPE: DNA
<213> ORGANISM: Homo sapiens

<400> SEQUENCE: 35
gcaacacata caacgactaa tcttcttttc gacgccgagg agctctgcag tgggggcgta        60

<210> SEQ ID NO 36
<211> LENGTH: 60
<212> TYPE: DNA
<213> ORGANISM: Homo sapiens

<400> SEQUENCE: 36
gtaggtgctg agtaagtgag cacttgcctc gaggggcagg gggcggtcct gggccaggcg        60

<210> SEQ ID NO 37
<211> LENGTH: 60
<212> TYPE: DNA
<213> ORGANISM: Homo sapiens

<400> SEQUENCE: 37
cagaaagacc ttgcaatcat acggtgcttc gacgccgagg agctctgcag tgggggcgta        60

<210> SEQ ID NO 38
<211> LENGTH: 60
<212> TYPE: DNA
<213> ORGANISM: Homo sapiens

<400> SEQUENCE: 38
tactgtgctg tgctcgtcaa agagtatgtc gatctatgag gaaatgcccc cagcctccca        60

<210> SEQ ID NO 39
<211> LENGTH: 60
<212> TYPE: DNA
<213> ORGANISM: Homo sapiens

<400> SEQUENCE: 39
cagaaattaa tcaaatgcaa gtgcaccctc gaccacccaa gggctgagga gtgcgggcac        60

<210> SEQ ID NO 40
<211> LENGTH: 60
<212> TYPE: DNA
<213> ORGANISM: Homo sapiens

<400> SEQUENCE: 40
aagggaccta gtcccctatt aagatttctc gaggggccag gcttttatac ccccatctga        60

<210> SEQ ID NO 41
<211> LENGTH: 60
<212> TYPE: DNA
<213> ORGANISM: Homo sapiens

<400> SEQUENCE: 41
cctgccgaga cacgggacgt gggattgctc gatctatgag gaaatgcccc cagcctccca        60

<210> SEQ ID NO 42
<211> LENGTH: 60
<212> TYPE: DNA
<213> ORGANISM: Homo sapiens
```

```
<400> SEQUENCE: 42
ccaaagctcg ctttcttaac cactatgctc gaggggccag gcttttatac ccccatctga    60

<210> SEQ ID NO 43
<211> LENGTH: 60
<212> TYPE: DNA
<213> ORGANISM: Homo sapiens

<400> SEQUENCE: 43
tgaattgtgt agcgtaagaa tttatatctc gaagtttgtg aactggcagg tggacgggga    60

<210> SEQ ID NO 44
<211> LENGTH: 60
<212> TYPE: DNA
<213> ORGANISM: Homo sapiens

<400> SEQUENCE: 44
acctgatctg gggaagatta ggaattgttc gaaaccaatt tcctgggatg ggggtgggggg   60

<210> SEQ ID NO 45
<211> LENGTH: 60
<212> TYPE: DNA
<213> ORGANISM: Homo sapiens

<400> SEQUENCE: 45
gcaagaggat ctcttgaggc ccaggagttc gaggggccag gcttttatac ccccatctga    60

<210> SEQ ID NO 46
<211> LENGTH: 60
<212> TYPE: DNA
<213> ORGANISM: Homo sapiens

<400> SEQUENCE: 46
tatcaagtga tccaaaaggc tgccagtgtc gaggggcagg gggcggtcct gggccaggcg    60

<210> SEQ ID NO 47
<211> LENGTH: 60
<212> TYPE: DNA
<213> ORGANISM: Homo sapiens

<400> SEQUENCE: 47
aagggaccta gtcccctatt aagatttctc gaaaccaatt tcctgggatg ggggtggggg    60

<210> SEQ ID NO 48
<211> LENGTH: 60
<212> TYPE: DNA
<213> ORGANISM: Homo sapiens

<400> SEQUENCE: 48
tatggacttt gtagtctcat atcaaagctc gaaaccaatt tcctgggatg ggggtggggg    60

<210> SEQ ID NO 49
<211> LENGTH: 60
<212> TYPE: DNA
<213> ORGANISM: Homo sapiens

<400> SEQUENCE: 49
aaaaataatc tggctctaca cttaggattc gaaaccaatt tcctgggatg ggggtggggg    60

<210> SEQ ID NO 50
<211> LENGTH: 60
<212> TYPE: DNA
<213> ORGANISM: Homo sapiens
```

```
<400> SEQUENCE: 50
tgatcactgt ttcctatgag gatacagctc gaggggcagg gggcggtcct gggccaggcg    60

<210> SEQ ID NO 51
<211> LENGTH: 60
<212> TYPE: DNA
<213> ORGANISM: Homo sapiens

<400> SEQUENCE: 51
aacctggaga acgccaagcg cttcgccatc gaggggcagg gggcggtcct gggccaggcg    60

<210> SEQ ID NO 52
<211> LENGTH: 60
<212> TYPE: DNA
<213> ORGANISM: Homo sapiens

<400> SEQUENCE: 52
ctacctttgt ggcacttggt acagcaaatc gacgggcccc gtgaggcggg ggcgggaccc    60

<210> SEQ ID NO 53
<211> LENGTH: 60
<212> TYPE: DNA
<213> ORGANISM: Homo sapiens

<400> SEQUENCE: 53
catcaattat aactcacctt acagatcatc gacgggcccc gtgaggcggg ggcgggaccc    60

<210> SEQ ID NO 54
<211> LENGTH: 60
<212> TYPE: DNA
<213> ORGANISM: Homo sapiens

<400> SEQUENCE: 54
tgatcactgt ttcctatgag gatacagctc gaagattagg taaaggtggg gacgcggaga    60

<210> SEQ ID NO 55
<211> LENGTH: 60
<212> TYPE: DNA
<213> ORGANISM: Homo sapiens

<400> SEQUENCE: 55
gaaaggtaat tgcccccaat atttattttc gaaacagatc gggcggctcg ggttacacac    60

<210> SEQ ID NO 56
<211> LENGTH: 60
<212> TYPE: DNA
<213> ORGANISM: Homo sapiens

<400> SEQUENCE: 56
ttctccacag ccggccggtc cttggcagtc gaggggcagg gggcggtcct gggccaggcg    60

<210> SEQ ID NO 57
<211> LENGTH: 60
<212> TYPE: DNA
<213> ORGANISM: Homo sapiens

<400> SEQUENCE: 57
cgtgtcccaa tttctagtgc actgtgaact cgacctcgcg ggaggggtgc caggccgcat    60

<210> SEQ ID NO 58
<211> LENGTH: 60
<212> TYPE: DNA
```

```
<400> SEQUENCE: 58
cctctcttct aaaaggtctc aacatcactc gactggagag cccggggcct cgcgccgctt    60

<210> SEQ ID NO 59
<211> LENGTH: 60
<212> TYPE: DNA
<213> ORGANISM: Homo sapiens

<400> SEQUENCE: 59
gtttcccctt gatgctcaga gaaaggcctc gaaacagatc gggcggctcg ggttacacac    60

<210> SEQ ID NO 60
<211> LENGTH: 60
<212> TYPE: DNA
<213> ORGANISM: Homo sapiens

<400> SEQUENCE: 60
cataatgcat gtgcatgaaa actaatcttc gatctatgag gaaatgcccc cagcctccca    60

<210> SEQ ID NO 61
<211> LENGTH: 60
<212> TYPE: DNA
<213> ORGANISM: Homo sapiens

<400> SEQUENCE: 61
agatgtgtaa gtcaccaggg agtgcattcg cgacctcgcg ggaggggtgc caggccgcat    60

<210> SEQ ID NO 62
<211> LENGTH: 60
<212> TYPE: DNA
<213> ORGANISM: Homo sapiens

<400> SEQUENCE: 62
gtaatggtgc catcatagct caagctcctc gatctatgag gaaatgcccc cagcctccca    60

<210> SEQ ID NO 63
<211> LENGTH: 60
<212> TYPE: DNA
<213> ORGANISM: Homo sapiens

<400> SEQUENCE: 63
aatacaaagg atggtatatt ttgcatattc gatctatgag gaaatgcccc cagcctccca    60

<210> SEQ ID NO 64
<211> LENGTH: 60
<212> TYPE: DNA
<213> ORGANISM: Homo sapiens

<400> SEQUENCE: 64
cctctcttct aaaaggtctc aacatcactc gatggtgcgg gaggtggccg gcagggttgg    60

<210> SEQ ID NO 65
<211> LENGTH: 60
<212> TYPE: DNA
<213> ORGANISM: Homo sapiens

<400> SEQUENCE: 65
ataattcttc ctggcacata ataagtattc gaatcgggcg ggttccggcg tgggtttcag    60

<210> SEQ ID NO 66
<211> LENGTH: 60
<212> TYPE: DNA
<213> ORGANISM: Homo sapiens
```

```
<400> SEQUENCE: 66
tctaaaggga tttccactat atgtagattc gaggggcgtg tgcgcgcgtg gcggggcccg    60

<210> SEQ ID NO 67
<211> LENGTH: 60
<212> TYPE: DNA
<213> ORGANISM: Homo sapiens

<400> SEQUENCE: 67
aacttatgat tctaatcttg aatgtctgtc gatctatgag gaaatgcccc cagcctccca    60

<210> SEQ ID NO 68
<211> LENGTH: 60
<212> TYPE: DNA
<213> ORGANISM: Homo sapiens

<400> SEQUENCE: 68
gaggtgggca gatcacgggg tcagggtatc gaggcccatc actggcgggg agacgggagg    60

<210> SEQ ID NO 69
<211> LENGTH: 60
<212> TYPE: DNA
<213> ORGANISM: Homo sapiens

<400> SEQUENCE: 69
actgaatatg aaaaaaaatg taaaaattat cgacctcgcg ggaggggtgc caggccgcat    60

<210> SEQ ID NO 70
<211> LENGTH: 60
<212> TYPE: DNA
<213> ORGANISM: Homo sapiens

<400> SEQUENCE: 70
gattttatag caaatttaca aaaatgagtc gatctatgag gaaatgcccc cagcctccca    60

<210> SEQ ID NO 71
<211> LENGTH: 60
<212> TYPE: DNA
<213> ORGANISM: Homo sapiens

<400> SEQUENCE: 71
accaagagtt ggaccccctt tttgatgttc gatggtgcgg gaggtggccg gcagggttgg    60

<210> SEQ ID NO 72
<211> LENGTH: 60
<212> TYPE: DNA
<213> ORGANISM: Homo sapiens

<400> SEQUENCE: 72
tatattgcta tctactagca aaggataatc gaagaggttc agggcggtgc ccgcggcgct    60

<210> SEQ ID NO 73
<211> LENGTH: 60
<212> TYPE: DNA
<213> ORGANISM: Homo sapiens

<400> SEQUENCE: 73
atcagtaagc tggtcagcta cccatgaatc gatctatgag gaaatgcccc cagcctccca    60

<210> SEQ ID NO 74
<211> LENGTH: 60
<212> TYPE: DNA
<213> ORGANISM: Homo sapiens
```

<400> SEQUENCE: 74
tgaaaacagt tcatcctgag tttcagtctc gaagattagg taaaggtggg gacgcggaga    60

<210> SEQ ID NO 75
<211> LENGTH: 60
<212> TYPE: DNA
<213> ORGANISM: Homo sapiens

<400> SEQUENCE: 75
gtgcagagcg agagcggggc agaggcggtc gaaactggga gaattcatct gaaatgatta    60

<210> SEQ ID NO 76
<211> LENGTH: 60
<212> TYPE: DNA
<213> ORGANISM: Homo sapiens

<400> SEQUENCE: 76
gaggcaggca gatcatgagg tcaggagttc gagccctgga ccccaggcca gctaatgagg    60

<210> SEQ ID NO 77
<211> LENGTH: 60
<212> TYPE: DNA
<213> ORGANISM: Homo sapiens

<400> SEQUENCE: 77
gctcactgca acctccacct cccaggttcg cgaacctcct gataacttca gcattaacag    60

<210> SEQ ID NO 78
<211> LENGTH: 60
<212> TYPE: DNA
<213> ORGANISM: Homo sapiens

<400> SEQUENCE: 78
agggtcttgc tatgttgccc aggctggcct cgagatcagc ctgggcaaca cggtgaaaac    60

<210> SEQ ID NO 79
<211> LENGTH: 60
<212> TYPE: DNA
<213> ORGANISM: Homo sapiens

<400> SEQUENCE: 79
tgtaatataa gcatagctca ctgcagcctc gaagcatttg tacgacattc tcatcttctt    60

<210> SEQ ID NO 80
<211> LENGTH: 60
<212> TYPE: DNA
<213> ORGANISM: Homo sapiens

<400> SEQUENCE: 80
acagaggagc gaggcccgat ccttactttc gaactcctga cctcgtgatc tgcccacctc    60

<210> SEQ ID NO 81
<211> LENGTH: 60
<212> TYPE: DNA
<213> ORGANISM: Homo sapiens

<400> SEQUENCE: 81
gggtttcacc atgttagcca ggatggtctc gatctcctga cctcatgatc cgcctgcctc    60

<210> SEQ ID NO 82
<211> LENGTH: 60
<212> TYPE: DNA
<213> ORGANISM: Homo sapiens

<400> SEQUENCE: 82
gcatttcacc atgttggtga ggctggtctc gaagagttca cacgtgtcca aatttggtgg    60

<210> SEQ ID NO 83
<211> LENGTH: 60
<212> TYPE: DNA
<213> ORGANISM: Homo sapiens

<400> SEQUENCE: 83
ctgggatcac aggcatgtgc caccatgctc gacaagaata gtctccttgt ttctgaacat    60

<210> SEQ ID NO 84
<211> LENGTH: 60
<212> TYPE: DNA
<213> ORGANISM: Homo sapiens

<400> SEQUENCE: 84
gtatttctgg ttctagatcc ttgaggaatc gagcagaagg agtctctccc tgaggccacc    60

<210> SEQ ID NO 85
<211> LENGTH: 60
<212> TYPE: DNA
<213> ORGANISM: Homo sapiens

<400> SEQUENCE: 85
cgaggcgggc ggatcacgag gtcaggagat cgacccccac gttctcacca cctgtttctt    60

<210> SEQ ID NO 86
<211> LENGTH: 60
<212> TYPE: DNA
<213> ORGANISM: Homo sapiens

<400> SEQUENCE: 86
gtatttctgg ttctagatcc ttgaggaatc gacctcctgg gctcaaccta tcctcccacc    60

<210> SEQ ID NO 87
<211> LENGTH: 60
<212> TYPE: DNA
<213> ORGANISM: Homo sapiens

<400> SEQUENCE: 87
gggtttcact gtgttagcca ggatggtctc gacctccctg gctcaagtga tcttcccacc    60

<210> SEQ ID NO 88
<211> LENGTH: 60
<212> TYPE: DNA
<213> ORGANISM: Homo sapiens

<400> SEQUENCE: 88
tgccctagag atctgtggaa ctttgaactc gatatatgaa aatagttttt taattataaa    60

<210> SEQ ID NO 89
<211> LENGTH: 60
<212> TYPE: DNA
<213> ORGANISM: Homo sapiens

<400> SEQUENCE: 89
ggtgggggaa tcacttgagg tcagaagttc gagaccatcc tgggcaacat ggtaaaaccc    60

<210> SEQ ID NO 90
<211> LENGTH: 60
<212> TYPE: DNA
<213> ORGANISM: Homo sapiens

<400> SEQUENCE: 90
aatggcacga tcacggctca ctgcagcctc gaatgttact gacagtggac acagtaagaa    60

<210> SEQ ID NO 91
<211> LENGTH: 60
<212> TYPE: DNA
<213> ORGANISM: Homo sapiens

<400> SEQUENCE: 91
gagttttgcc atgttgccca ggctggtctc gagaacagcc tggccaacat ggtgaaaccc    60

<210> SEQ ID NO 92
<211> LENGTH: 60
<212> TYPE: DNA
<213> ORGANISM: Homo sapiens

<400> SEQUENCE: 92
aggtctcact atgttgcccg ggctggtctc gacgccgagg agctctgcag tgggggcgta    60

<210> SEQ ID NO 93
<211> LENGTH: 60
<212> TYPE: DNA
<213> ORGANISM: Homo sapiens

<400> SEQUENCE: 93
gggtttcacc atgttggcga ggctggtctc gaactcctga cctcaggtga tccgcctgcc    60

<210> SEQ ID NO 94
<211> LENGTH: 60
<212> TYPE: DNA
<213> ORGANISM: Homo sapiens

<400> SEQUENCE: 94
ggtgggtgga tcacctgagg tcaggagttc gacctaaggg tggtcataat tctgctgctg    60

<210> SEQ ID NO 95
<211> LENGTH: 60
<212> TYPE: DNA
<213> ORGANISM: Homo sapiens

<400> SEQUENCE: 95
gggtctcaca gccttcagag ctgagagcct aggcttcagt gagccataat cacgccacta    60

<210> SEQ ID NO 96
<211> LENGTH: 60
<212> TYPE: DNA
<213> ORGANISM: Homo sapiens

<400> SEQUENCE: 96
ctttgggagg ccaaggtgag tggattgctc gacatctcat ttgataggat taagtcaacg    60

<210> SEQ ID NO 97
<211> LENGTH: 60
<212> TYPE: DNA
<213> ORGANISM: Homo sapiens

<400> SEQUENCE: 97
aggtctcact atgttgcccg ggctggtctc gaacagcagc gtgtgcgccg acagcgcgcc    60

<210> SEQ ID NO 98
<211> LENGTH: 60
<212> TYPE: DNA
<213> ORGANISM: Homo sapiens

<400> SEQUENCE: 98
tctgtcgccc aggttggagt acagtggctc gaggatgtcc tattttgcca ccttatctaa         60

<210> SEQ ID NO 99
<211> LENGTH: 60
<212> TYPE: DNA
<213> ORGANISM: Homo sapiens

<400> SEQUENCE: 99
ttatatctcc tacctccaag cctggcagtc gattccaaag tgaagcaaaa aaaaaacttc         60

<210> SEQ ID NO 100
<211> LENGTH: 60
<212> TYPE: DNA
<213> ORGANISM: Homo sapiens

<400> SEQUENCE: 100
aaagaccctg tctctaaata aatagaacat cgagatcatg ccactgcact ccagcctggg         60

<210> SEQ ID NO 101
<211> LENGTH: 60
<212> TYPE: DNA
<213> ORGANISM: Homo sapiens

<400> SEQUENCE: 101
ggggtttttc catgttagtc aggctggtct aatggctccc ttaccttgct ggctgtgggc         60

<210> SEQ ID NO 102
<211> LENGTH: 60
<212> TYPE: DNA
<213> ORGANISM: Homo sapiens

<400> SEQUENCE: 102
agtggcatga tcacagctca ctgccacctc gaaaccaaac cctgtgactt caacacccaa         60

<210> SEQ ID NO 103
<211> LENGTH: 60
<212> TYPE: DNA
<213> ORGANISM: Homo sapiens

<400> SEQUENCE: 103
ccctccctca acatgcaggg attacaattc gaagatggtc tgaaggaagc aattgggaaa         60

<210> SEQ ID NO 104
<211> LENGTH: 60
<212> TYPE: DNA
<213> ORGANISM: Homo sapiens

<400> SEQUENCE: 104
tatataattt ccactttgtt tttaataatc gaaacataac tgttctaaaa tatgtcaagt         60

<210> SEQ ID NO 105
<211> LENGTH: 60
<212> TYPE: DNA
<213> ORGANISM: Homo sapiens

<400> SEQUENCE: 105
tgctgaaaga aaacacaatt tatttaagtc gagaccatcc tagctaacac ggtgaaaccc         60

<210> SEQ ID NO 106
<211> LENGTH: 60
<212> TYPE: DNA
<213> ORGANISM: Homo sapiens

```
<400> SEQUENCE: 106
gttttaacat ttaaagataa aatccccatc gaacccaggg aggcagaggt agcagtgagc    60

<210> SEQ ID NO 107
<211> LENGTH: 60
<212> TYPE: DNA
<213> ORGANISM: Homo sapiens

<400> SEQUENCE: 107
agctgattgt gtaactctca gtctgagctc gaacccaggg aggcagaggt agcagtgagc    60

<210> SEQ ID NO 108
<211> LENGTH: 60
<212> TYPE: DNA
<213> ORGANISM: Homo sapiens

<400> SEQUENCE: 108
gggaaataaa tattatgaag ctttagtgtc gaacccaggg aggcagaggt agcagtgagc    60

<210> SEQ ID NO 109
<211> LENGTH: 60
<212> TYPE: DNA
<213> ORGANISM: Homo sapiens

<400> SEQUENCE: 109
taccaggaag atattttata aatgaatgtc gaagacagtt ttgagatttg cttttcctag    60

<210> SEQ ID NO 110
<211> LENGTH: 60
<212> TYPE: DNA
<213> ORGANISM: Homo sapiens

<400> SEQUENCE: 110
taagtgggag aaaagacaaa gatttctctc gaggtgagcg gatcacctga ggtcaggagt    60

<210> SEQ ID NO 111
<211> LENGTH: 60
<212> TYPE: DNA
<213> ORGANISM: Homo sapiens

<400> SEQUENCE: 111
agatcttaaa gcaagctaaa agagctattc gaacccaggg aggcagaggt agcagtgagc    60

<210> SEQ ID NO 112
<211> LENGTH: 60
<212> TYPE: DNA
<213> ORGANISM: Homo sapiens

<400> SEQUENCE: 112
tctccttttg ggcacatagg acataaaatc gaacccaggg aggcagaggt agcagtgagc    60

<210> SEQ ID NO 113
<211> LENGTH: 60
<212> TYPE: DNA
<213> ORGANISM: Homo sapiens

<400> SEQUENCE: 113
ttcattcccg caaagggtc atatatactc gaacccaggg aggcagaggt agcagtgagc    60

<210> SEQ ID NO 114
<211> LENGTH: 60
<212> TYPE: DNA
<213> ORGANISM: Homo sapiens
```

<400> SEQUENCE: 114
atactgacac actattccac ccacaaagtc gaacccaggg aggcagaggt agcagtgagc      60

<210> SEQ ID NO 115
<211> LENGTH: 60
<212> TYPE: DNA
<213> ORGANISM: Homo sapiens

<400> SEQUENCE: 115
ctaatgtgct agtttgtcca catattaatc gagcctgcag tgagccatga tcatgccact      60

<210> SEQ ID NO 116
<211> LENGTH: 60
<212> TYPE: DNA
<213> ORGANISM: Homo sapiens

<400> SEQUENCE: 116
ttctttcttt aagctttgct tctatcattc gagataattt agaattaaga aggaataaac      60

<210> SEQ ID NO 117
<211> LENGTH: 60
<212> TYPE: DNA
<213> ORGANISM: Homo sapiens

<400> SEQUENCE: 117
aggttttgcc aagttggctg ggatggtctc gagaccagcc tgaccaacat ggagaaaccc      60

<210> SEQ ID NO 118
<211> LENGTH: 60
<212> TYPE: DNA
<213> ORGANISM: Homo sapiens

<400> SEQUENCE: 118
ggaaccaaac tggaattcag gagacaattc gaacccaggg aggcagaggt agcagtgagc      60

<210> SEQ ID NO 119
<211> LENGTH: 60
<212> TYPE: DNA
<213> ORGANISM: Homo sapiens

<400> SEQUENCE: 119
cacattaaca cctgtcaata aacaggattc gaacccaggg aggcagaggt agcagtgagc      60

<210> SEQ ID NO 120
<211> LENGTH: 60
<212> TYPE: DNA
<213> ORGANISM: Homo sapiens

<400> SEQUENCE: 120
gtacaaagaa gtgatgtagc atgtcctgtc gaacccaggg aggcagaggt agcagtgagc      60

<210> SEQ ID NO 121
<211> LENGTH: 60
<212> TYPE: DNA
<213> ORGANISM: Homo sapiens

<400> SEQUENCE: 121
tatataattt ccactttgtt tttaataatc gaaggacata tgatgggtgt ggctcgcctg      60

<210> SEQ ID NO 122
<211> LENGTH: 60
<212> TYPE: DNA
<213> ORGANISM: Homo sapiens

<400> SEQUENCE: 122
agaaatgagt caggttcaat gaattgtctc gagaccatca tggctaacac ggtgaaaccc     60

<210> SEQ ID NO 123
<211> LENGTH: 60
<212> TYPE: DNA
<213> ORGANISM: Homo sapiens

<400> SEQUENCE: 123
caagtggatg ggacacccac catgtccctc gaacccaggg aggcagaggt agcagtgagc     60

<210> SEQ ID NO 124
<211> LENGTH: 60
<212> TYPE: DNA
<213> ORGANISM: Homo sapiens

<400> SEQUENCE: 124
aatctttcat gaggaggcaa tcaagatgtc gactgctgtg ctagcaatga gcgaggctcc     60

<210> SEQ ID NO 125
<211> LENGTH: 60
<212> TYPE: DNA
<213> ORGANISM: Homo sapiens

<400> SEQUENCE: 125
gaagtcaccg tcggcaggtt ctgctgcttc gaacccaggg aggcagaggt agcagtgagc     60

<210> SEQ ID NO 126
<211> LENGTH: 60
<212> TYPE: DNA
<213> ORGANISM: Homo sapiens

<400> SEQUENCE: 126
gtcaaacctt tgaaaactgc agctccagtc gactgctgtg ctagcaatga gcgaggctcc     60

<210> SEQ ID NO 127
<211> LENGTH: 60
<212> TYPE: DNA
<213> ORGANISM: Homo sapiens

<400> SEQUENCE: 127
gttgtgacaa ttttcacaga agcgttgttc gaacccaggg aggcagaggt agcagtgagc     60

<210> SEQ ID NO 128
<211> LENGTH: 60
<212> TYPE: DNA
<213> ORGANISM: Homo sapiens

<400> SEQUENCE: 128
aatgcttatg ttctaattcc aaaaggaatc gagcctgcag tgagccatga tcatgccact     60

<210> SEQ ID NO 129
<211> LENGTH: 60
<212> TYPE: DNA
<213> ORGANISM: Homo sapiens

<400> SEQUENCE: 129
gctctgtcaa gaagacagag caaggtcttc gagcctgcag tgagccatga tcatgccact     60

<210> SEQ ID NO 130
<211> LENGTH: 60
<212> TYPE: DNA
<213> ORGANISM: Homo sapiens

<400> SEQUENCE: 130
gggtttcacc gtgttagcca ggatggtctc gagaccatcc tggctaacat ggtgaaacca    60

<210> SEQ ID NO 131
<211> LENGTH: 60
<212> TYPE: DNA
<213> ORGANISM: Homo sapiens

<400> SEQUENCE: 131
atataaatta catgtcaaga agataatgtc gagaccatcc tgaccaacat ggtgaaacct    60

<210> SEQ ID NO 132
<211> LENGTH: 60
<212> TYPE: DNA
<213> ORGANISM: Homo sapiens

<400> SEQUENCE: 132
catgatagtt aagagatcat atctagaatc gattctctat ttcatttatt tccactgtaa    60

<210> SEQ ID NO 133
<211> LENGTH: 60
<212> TYPE: DNA
<213> ORGANISM: Homo sapiens

<400> SEQUENCE: 133
gggtttcacc atattggcca ggctggtctc gagaccagcc tggccaacat ggtgaaaccc    60

<210> SEQ ID NO 134
<211> LENGTH: 60
<212> TYPE: DNA
<213> ORGANISM: Homo sapiens

<400> SEQUENCE: 134
aggttttgcc aagttggctg gatggtctc gagaccatcc tggccaacat ggtgaaaacc    60

<210> SEQ ID NO 135
<211> LENGTH: 60
<212> TYPE: DNA
<213> ORGANISM: Homo sapiens

<400> SEQUENCE: 135
ggctggcaga tcacctaagg tcaggcattc gagagcatga aataaagact tgttaaggct    60

<210> SEQ ID NO 136
<211> LENGTH: 60
<212> TYPE: DNA
<213> ORGANISM: Homo sapiens

<400> SEQUENCE: 136
gagtgattgt ggttccgagg tcaggaggtc gacatatttc ctgttccctt ggaataaaaa    60

<210> SEQ ID NO 137
<211> LENGTH: 60
<212> TYPE: DNA
<213> ORGANISM: Homo sapiens

<400> SEQUENCE: 137
tccaggtact tctcttagcc ttatggcttc gatgtgagag gcactctctt tcactaatag    60

<210> SEQ ID NO 138
<211> LENGTH: 60
<212> TYPE: DNA
<213> ORGANISM: Homo sapiens

```
<400> SEQUENCE: 138
ggttttcacc atgttggcca ggatggtctc gagaccagcc tggccaacat ggtgaaaccc    60

<210> SEQ ID NO 139
<211> LENGTH: 60
<212> TYPE: DNA
<213> ORGANISM: Homo sapiens

<400> SEQUENCE: 139
tttatatttt aaaaatttgg gttttttttc gaggctgcaa tgagccatga tcacaccact    60

<210> SEQ ID NO 140
<211> LENGTH: 60
<212> TYPE: DNA
<213> ORGANISM: Homo sapiens

<400> SEQUENCE: 140
tgctgaaaga aaacacaatt tatttaagtc gaataaatgt gtggctatct tacagtgatt    60

<210> SEQ ID NO 141
<211> LENGTH: 60
<212> TYPE: DNA
<213> ORGANISM: Homo sapiens

<400> SEQUENCE: 141
gggtttcacc atgttagcca ggatggtctc gagaccagcc tggccaacat ggtgaaaccc    60

<210> SEQ ID NO 142
<211> LENGTH: 60
<212> TYPE: DNA
<213> ORGANISM: Homo sapiens

<400> SEQUENCE: 142
gagtttcacc atgttgacca ggctggtctc gagatcagcc tgggcaacat ggtgaaaccc    60

<210> SEQ ID NO 143
<211> LENGTH: 60
<212> TYPE: DNA
<213> ORGANISM: Homo sapiens

<400> SEQUENCE: 143
gggaggactg gatcaggaat ctgtgtcttc gaacccaggg aggcagaggt agcagtgagc    60

<210> SEQ ID NO 144
<211> LENGTH: 60
<212> TYPE: DNA
<213> ORGANISM: Homo sapiens

<400> SEQUENCE: 144
tacaacaatt aagatatcac ctatattctc gagaccatcc tagctaacat ggtgaaatct    60

<210> SEQ ID NO 145
<211> LENGTH: 60
<212> TYPE: DNA
<213> ORGANISM: Homo sapiens

<400> SEQUENCE: 145
gagggaaaaa tactaaggcc actaaaaatc gagaccatcc tggacaacat ggagaaacac    60

<210> SEQ ID NO 146
<211> LENGTH: 60
<212> TYPE: DNA
<213> ORGANISM: Homo sapiens
```

```
<400> SEQUENCE: 146 gggtttttaac atattggcca ggctggtctc gagaccagcc tggccaatgt ggtgaaaccc    60

<210> SEQ ID NO 147
<211> LENGTH: 60
<212> TYPE: DNA
<213> ORGANISM: Homo sapiens

<400> SEQUENCE: 147
ggatttcacc atgttggcca ggctggtctc gagaccagcc tggccaacat ggtgaaaccc    60

<210> SEQ ID NO 148
<211> LENGTH: 60
<212> TYPE: DNA
<213> ORGANISM: Homo sapiens

<400> SEQUENCE: 148
gtttattgca gcattggcct gtggagactc gagcctgcag tgagccatga tcatgccact    60

<210> SEQ ID NO 149
<211> LENGTH: 60
<212> TYPE: DNA
<213> ORGANISM: Homo sapiens

<400> SEQUENCE: 149
aaacgggacc agcagcgcta ctcaggcctc gactgctgtg ctagcaatga gcgaggctcc    60

<210> SEQ ID NO 150
<211> LENGTH: 60
<212> TYPE: DNA
<213> ORGANISM: Homo sapiens

<400> SEQUENCE: 150
ccatgttggt caggctggtc tcaaactctc gagaccagcc tggccaacat ggtgaaaccc    60

<210> SEQ ID NO 151
<211> LENGTH: 60
<212> TYPE: DNA
<213> ORGANISM: Homo sapiens

<400> SEQUENCE: 151
gggtttctcc atgctggtca ggctggtctc gagaccagcc tggccaacat ggtgaaaccc    60

<210> SEQ ID NO 152
<211> LENGTH: 60
<212> TYPE: DNA
<213> ORGANISM: Homo sapiens

<400> SEQUENCE: 152
gggtttcgcc atgttggcca ggctggtctc gagaccagcc tggccaacat ggtgaaaccc    60
```

EPIGENETIC CHROMOSOME INTERACTIONS

FIELD OF THE INVENTION

The invention relates to detecting chromosome interactions and rheumatoid arthritis. More particularly, the invention relates to a method of determining responsiveness to a specific therapy for rheumatoid arthritis in a subject; a companion diagnostic method; a therapeutic agent for use in the treatment and/or prophylaxis of rheumatoid arthritis in an individual (in particular in a human individual); a method of screening for (identifying) an agent, in particular a therapeutic agent, which is capable of changing responsiveness (in particular of an individual e.g. human individual) to a therapy for rheumatoid arthritis; a method of determining the effect of a drug (e.g. therapeutic agent) comprising detecting the change in epigenetic chromosome interactions caused by the drug; and/or a library of nucleic acid and/or a nucleic acid.

Background of the Invention

Healthcare costs are spiralling and so there is a need to treat people more effectively using existing drugs. Some patients are non-responsive to particular pharmaceutical treatments. One example is the treatment of rheumatoid arthritis by methotrexate (MTX).

Rheumatoid arthritis (RA) is a chronic autoimmune disease affecting up to 1% of the global population. Pathogenesis is multifactorial and characterized by primarily immune host gene loci interacting with environmental factors, particularly smoking and other pulmonary stimuli[1,2,3]. The exposure of a genetically susceptible individual to such environmental factors suggests an epigenetic context for disease onset and progression. Recent studies of chromatin markers (e.g. methylation status of the genome) provide the first evidence of epigenetic differences associated with RA[4,5,6,7]. However, to date neither genetic associations, nor epigenetic changes, have provided a validated predictive marker for response to a given therapy. Moreover, clinical presentation only weakly predicts the efficacy and toxicity of known disease modifying anti-rheumatic drugs (DMARDs) such as methotrexate (MTX).

MTX[8], the commonest first-choice medication recommended by EULAR and ACR management guidelines, delivers clinically meaningful response rates ranging from 50% to 65% after 6 months of treatment[11]. Such responses, and especially the rather smaller proportion that exhibits high hurdle responses, cannot currently be predicted in an individual patient. This begets a 'trial and error' based approach to therapeutic regimen choice (mono or combinatorial therapeutics).

The ability to predict responsiveness to MTX, and/or other RA drugs, in an individual patient would be an invaluable clinical tool, given that response to first-line treatment is the most significant predictor of long-term outcome[9,10].

SUMMARY OF THE INVENTION

The inventors have investigated the use of epigenetic chromosome interactions as the basis of or for use in conjunction with companion diagnostics to rheumatoid arthritis (RA), and in particular in the detection of epigenetic states to determine responsiveness to RA therapy, in particular pharmaceutical therapy of RA such as methotrexate.

The inventors' work shows the role played by epigenetic interactions and provides methods for identifying the relevant chromosomal interactions. The invention relates to using chromosome interactions as the basis for companion diagnostic tests.

Accordingly, a first aspect of the present invention provides a method of determining responsiveness to a specific therapy (in particular a specific pharmaceutical therapy) for rheumatoid arthritis in a subject (preferably a mammalian such as human subject), comprising detecting the presence or absence of 5 or more (in particular 7 or more, or 10 or more, or 15 or more, or 20 or more) chromosomal interactions, wherein said chromosomal interactions are preferably at 5 or more (for example 5) different loci.

Preferably, in all aspects of the invention, said detecting comprises determining for each interaction whether or not the regions of a chromosome which are part of the interaction have been brought together.

More preferably, in all aspects of the invention, said detecting comprises determining for each interaction whether or not the regions of a chromosome which are part of the interaction have been brought together, by cross-linking chromosome interactions in a sample from the subject and detecting whether a sequence from both chromosome regions which are brought together is present in the cross-linked product.

Preferably, in all aspects of the invention, the chromosome interactions are or have been identified in an assay method that that identifies chromosome interactions which are relevant to subgroups that comprises contacting a first set of nucleic acids from the subgroups with a second set of nucleic acids representing an index population of chromosome interactions, and allowing complementary sequences to hybridise, wherein the nucleic acids in the first and second sets of nucleic acids represent (in particular are in the form of) a ligated product comprising sequences from both of the chromosome regions that have come together in the epigenetic chromosome interaction, and wherein the pattern of hybridisation between the first and second set of nucleic acids allows a determination of which epigenetic chromosome interactions are specific to subgroups in the population, wherein the subgroups differ in responsiveness to a specific therapy for rheumatoid arthritis.

Preferably, in all aspects of the invention, the feature " . . . the nucleic acids in the first and second sets of nucleic acids represent a ligated product comprising sequences from both of the chromosome regions that have come together in the epigenetic chromosome interaction . . . " comprises or is: " . . . the nucleic acids in the first and second sets of nucleic acids are in the form of a ligated product(s) (preferably a ligated nucleic acid(s), more preferably ligated DNA) comprising sequences from both of the chromosome regions that have come together in the epigenetic chromosome interaction".

More preferably, in all aspects of the invention:
the first set of nucleic acids is from at least 8 individuals, and/or
the first set of nucleic acids is from at least 4 individuals from a first subgroup and at least 4 individuals from a second subgroup which is preferably non-overlapping with the first subgroup, and/or
the second set of nucleic acids represents an unselected group of chromosome interactions, and/or
the second set of nucleic acids is bound to an array at defined locations, and/or
the second set of nucleic acids represents chromosome interactions in least 100 different genes or loci, and/or the second set of nucleic acids comprises at least 1000 different nucleic acids representing at least 1000 different epigenetic chromosome interactions, and/or the first set of nucleic acids and the second set of nucleic acids comprise nucleic acid sequences of length 10 to 100 nucleotide bases, and/or the first set of nucleic acids is or has been generated in a method comprising the steps:
  (i) in vitro cross-linking of chromosome regions which have come together in a chromosome interaction;
  (ii) subjecting said cross-linked DNA to restriction digestion cleavage with an enzyme; and
  (iii) ligating said cross-linked cleaved DNA ends to form the first set of nucleic acids (in particular comprising ligated DNA).

Preferably, in all aspects of the invention, the subject is human; and/or the subgroups are subgroups in a human population.

Preferably, in all aspects of the invention:
a. said locus is a gene, and/or
b. a microRNA (miRNA) is expressed from the locus, and/or
c. a non-coding RNA (ncRNA) is expressed from the locus, and/or
d. the locus expresses a nucleic acid sequence encoding at least 10 contiguous amino acid residues, and/or
e. the locus expresses a regulating element.

Preferably, in all aspects of the invention, 5 or more (in particular 5 to 20, 5 to 100, 5 to 300, or 5 to 500), 7 or more (e.g. 7 to 500 or 7 to 100), more preferably 10 or more or 15 or more (e.g. 10 to 500 or 10 to 100 or 15 to 500 or 15 to 100), or even more preferably 20 or more (e.g. 20 to 500, 20 to 300 or 20 to 100), yet more preferably 50 or more e.g. 50 to 100, epigenetic chromosome interactions are typed.

Preferably, in the first aspect (and/or all other aspects) of the invention, the specific therapy (in particular the specific pharmaceutical therapy) for rheumatoid arthritis, and/or the therapeutic agent (in particular the pharmaceutical therapeutic agent), comprises a pharmaceutically active agent (e.g. a compound or a biologic/biological agent such as a protein or antibody) suitable for use (in particular human use) in the treatment and/or prophylaxis of rheumatoid arthritis (RA), preferably a disease modifying anti-rheumatic drug (DMARD); in particular in a mammal, more particularly in a human.

More preferably, in all aspects of the invention, the pharmaceutically active agent comprises:
a synthetic disease modifying anti-rheumatic drug (sDMARD), preferably comprising:
  a sDMARD which inhibits the metabolism and/or action of folic acid (preferably a sDMARD being an inhibitor of mammalian dihydrofolate reductase (DHFR), most preferably methotrexate, or less preferably pemetrexed);
  sulfasalazine, or 5-aminosalicylic acid (5-ASA, mesalazine) which is an active metabolite of sulfasalazine,
  a sDMARD which is a pyrimidine synthesis inhibitor (in particular a dihydroorotate dehydrogenase (DHODH) inhibitor), most preferably leflunomide or its active metabolite teriflunomide,
  a quinolone-class antimalarial drug and sDMARD, most preferably hydroxychloroquine,
  a Janus kinase (JAK) inhibitor sDMARD, preferably a JAK-1 and/or JAK-3 inhibitor sDMARD, most preferably tofacitinib,
  or a combination of 2, 3 or more of the sDMARDs listed herein (such a combination can, in particular, comprise or be: methotrexate+sulfasalazine, methotrexate+leflunomide, methotrexate+hydroxychloroquine, sulfasalazine+leflunomide, methotrexate+sulfasalazine+hydroxychloroquine, [sulfasalazine and/or leflunomide]+hydroxychloroquine, or tofacitinib+[methotrexate, sulfasalazine, leflunomide, and/or hydroxychloroquine]);
wherein each sDMARD compound mentioned hereinabove can, independently, be in the form of the free compound and/or a pharmaceutically acceptable salt thereof; and/or a TNF-alpha (tumor necrosis factor alpha) inhibitor, in particular: a monoclonal antibody TNF-alpha inhibitor such as infliximab, adalimumab, certolizumab pegol, golimumab, or a biosimilar (in particular a USA- (e.g. FDA-) and/or European- (e.g. EMEA-) approved biosimilar) of any of these (in particular a biosimilar of infliximab such as CT-P13); and/or a circulating receptor fusion protein TNF-alpha inhibitor such as etanercept or a biosimilar thereof (in particular a USA- (e.g. FDA-) and/or European-(e.g. EMEA-) approved biosimilar thereof); and/or a T cell costimulation inhibitor such as abatacept; and/or
an interleukin 1 (IL-1) inhibitor such as anakinra; and/or
a monoclonal antibody against B cells such as rituximab or a biosimilar thereof (in particular a USA-(e.g. FDA-) and/or European- (e.g. EMEA-) approved biosimilar thereof), and/or an interleukin-6 (IL-6) receptor inhibitor monoclonal antibody such as tocilizumab or a biosimilar thereof (in particular a USA- (e.g. FDA-) and/or European- (e.g. EMEA-) approved biosimilar thereof); and/or a glucocorticoid drug suitable for use in the treatment and/or prophylaxis of rheumatoid arthritis such as prednisone, prednisolone or dexamethasone (in particular a glucocorticoid drug in combination with an sDMARD, e.g. as listed hereinabove).

Even more preferably, in all aspects of the invention, the pharmaceutically active agent comprises:
a synthetic disease modifying anti-rheumatic drug (sDMARD), preferably comprising:
  a sDMARD which inhibits the metabolism and/or action of folic acid (preferably a sDMARD being an inhibitor of mammalian dihydrofolate reductase (DHFR), most preferably methotrexate, or less preferably pemetrexed);
  sulfasalazine, or 5-aminosalicylic acid (5-ASA, mesalazine) which is an active metabolite of sulfasalazine,
  a sDMARD which is a pyrimidine synthesis inhibitor (in particular a dihydroorotate dehydrogenase (DHODH) inhibitor), most preferably leflunomide or its active metabolite teriflunomide,
  a quinolone-class antimalarial drug and sDMARD, most preferably hydroxychloroquine,
  a Janus kinase (JAK) inhibitor sDMARD, preferably a JAK-1 and/or JAK-3 inhibitor sDMARD, most preferably tofacitinib,
  or a combination of 2, 3 or more of the sDMARDs listed herein (such a combination can, in particular, comprise or be: methotrexate+sulfasalazine, methotrexate+leflunomide, methotrexate+hydroxychloroquine, sulfasalazine+leflunomide, methotrexate+sulfasalazine+hydroxychloroquine, [sulfasalazine and/ or leflunomide]+hydroxychloroquine, or tofacitinib+ [methotrexate, sulfasalazine, leflunomide, and/or hydroxychloroquine]);

wherein each sDMARD compound mentioned hereinabove can, independently, be in the form of the free compound and/or a pharmaceutically acceptable salt thereof.

Most preferably, in all aspects of the invention, the pharmaceutically active agent comprises:

a synthetic disease modifying anti-rheumatic drug (sDMARD) which inhibits the metabolism and/or action of folic acid (preferably a sDMARD being an inhibitor of mammalian dihydrofolate reductase (DHFR), most preferably methotrexate, or less preferably pemetrexed);

or a combination of methotrexate or pemetrexed (preferably methotrexate) with 1 or more of the following sDMARDs: sulfasalazine, leflunomide, hydroxychloroquine, and/or tofacitinib;

wherein each sDMARD compound mentioned hereinabove can, independently, be in the form of the free compound and/or a pharmaceutically acceptable salt thereof.

Most preferably, in all aspects of the invention, the specific therapy for rheumatoid arthritis comprises methotrexate or a pharmaceutically acceptable salt thereof, in particular for use in the treatment and/or prophylaxis of rheumatoid arthritis.

A second aspect of the present invention provides an agent (in particular a pharmaceutically active agent, preferably methotrexate or a pharmaceutically acceptable salt thereof) which is therapeutic for rheumatoid arthritis, for use in treatment and/or prophylaxis of rheumatoid arthritis in an individual (preferably in a human individual) that has been identified as being in need of said agent by a method according to the first aspect of the invention. The second aspect of the invention also provides the use of an agent (in particular a pharmaceutically active agent, preferably methotrexate or a pharmaceutically acceptable salt thereof) which is therapeutic for rheumatoid arthritis, in the manufacture of a medicament (e.g. pharmaceutical composition comprising the pharmaceutically active agent) for use in treatment and/or prophylaxis of rheumatoid arthritis in an individual (preferably in a human individual) that has been identified as being in need of said agent by a method according to the first aspect of the invention. The second aspect of the invention also provides a method of treatment and/or prophylaxis of rheumatoid arthritis in an individual (preferably in a human individual), comprising administering to the individual an agent (in particular a pharmaceutically active agent, preferably methotrexate or a pharmaceutically acceptable salt thereof) which is therapeutic for rheumatoid arthritis, wherein the individual has been identified as being in need of said agent by a method according to the first aspect of the invention.

A third aspect of the present invention provides a method of identifying a substance which is capable of changing in an individual (preferably in a human individual) a non-responsive state to a responsive state, in respect of the individual's responsiveness to a therapeutic agent for rheumatoid arthritis, comprising determining whether or not a candidate agent is capable of changing the chromosomal interactions from those corresponding to a non-responsive state to those which correspond to a responsive state.

A fourth aspect of the present invention provides a method of determining whether a candidate substance (in particular a pharmaceutically active agent) is suitable for the treatment and/or prophylaxis of rheumatoid arthritis, comprising detecting the change in epigenetic chromosome interactions caused by the drug (i.e. the candidate substance, in particular a pharmaceutically active agent), wherein said interactions relate to the mechanism of action of the drug or the pharmacodynamics properties of the drug.

A fifth aspect of the present invention provides a library of nucleic acids (e.g. DNA and/or isolated nucleic acids) which comprises at least 200 different second nucleic acids (e.g. DNA and/or isolated nucleic acids), as defined herein, optionally bound to an array.

Preferably, in the fifth aspect of the invention, the library comprises 5 or more, 7 or more, 10 or more, 15 or more, 20 or more, 25 or more, 30 or more, or 40 or more, or 50 or more, nucleic acids (e.g. DNA and/or isolated nucleic acids) each of which comprise (for example each of which consist essentially of, e.g. consist of) a nucleic acid sequence (e.g. DNA sequence) selected from the group consisting of:

(i) the nucleic acid (e.g. DNA) sequences listed in Table 7a and/or Table 8a and/or Table 9 (preferably Table 7a and/or Table 8a, most preferably Table 7a); and (ii) nucleic acid (e.g. DNA) sequences having at least 70%, at least 80%, at least 85%, at least 90%, at least 95%, at least 97%, at least 98%, or at least 99% identity to one or more sequences listed in Table 7a and/or Table 8a and/or Table 9 (preferably Table 7a and/or Table 8a, most preferably Table 7a).

A sixth aspect of the present invention provides a library of nucleic acids (e.g. DNA and/or isolated nucleic acids) comprising 5 or more, 7 or more, 10 or more, 15 or more, 20 or more, 25 or more, 30 or more, or 40 or more, or 50 or more, or 70 or more, nucleic acids (e.g. DNA and/or isolated nucleic acids), each of which comprise (for example each of which consist essentially of, e.g. consist of) a nucleic acid sequence (e.g. DNA sequence) selected from the group consisting of:

(i) the nucleic acid (e.g. DNA) sequences listed in Table 7a and/or Table 8a and/or Table 9 (preferably Table 7a and/or Table 8a, most preferably Table 7a); and (ii) nucleic acid (e.g. DNA) sequences having at least 70%, at least 80%, at least 85%, at least 90%, at least 95%, at least 97%, at least 98%, or at least 99% identity to one or more sequences listed in Table 7a and/or Table 8a and/or Table 9 (preferably Table 7a and/or Table 8a, most preferably Table 7a).

A seventh aspect of the present invention provides a nucleic acid (e.g. DNA and/or an isolated nucleic acid) comprising (for example consisting essentially of, e.g. consisting of) a nucleic acid sequence (e.g. DNA sequence) selected from the group consisting of:

(i) the nucleic acid (e.g. DNA) sequences listed in Table 7a and/or Table 8a and/or Table 9 (preferably Table 7a and/or Table 8, most preferably Table 7a); and (ii) nucleic acid (e.g. DNA) sequences having at least 80%, at least 85%, at least 90%, at least 95%, at least 97%, at least 98%, or at least 99% identity to one or more sequences listed in Table 7a and/or Table 8a and/or Table 9 (preferably Table 7a and/or Table 8a, most preferably Table 7a).

The invention also provides a nucleic acid (e.g. DNA and/or an isolated nucleic acid) comprising (for example consisting essentially of, e.g. consisting of) a nucleic acid sequence (e.g. DNA sequence) selected from the nucleic acid (e.g. DNA) sequences listed in Table 7a and/or Table 8a and/or Table 9 (preferably Table 7a and/or Table 8a, most preferably Table 7a).

For clarity, sequence identity is the amount of nucleotide characters that match exactly between two sequences, and these values are typically estimated by common algorithms such as BLAST and/or BLAT. See hereinafter under "Homologues" for more information.

DETAILED DESCRIPTION OF THE INVENTION

Figure 1:
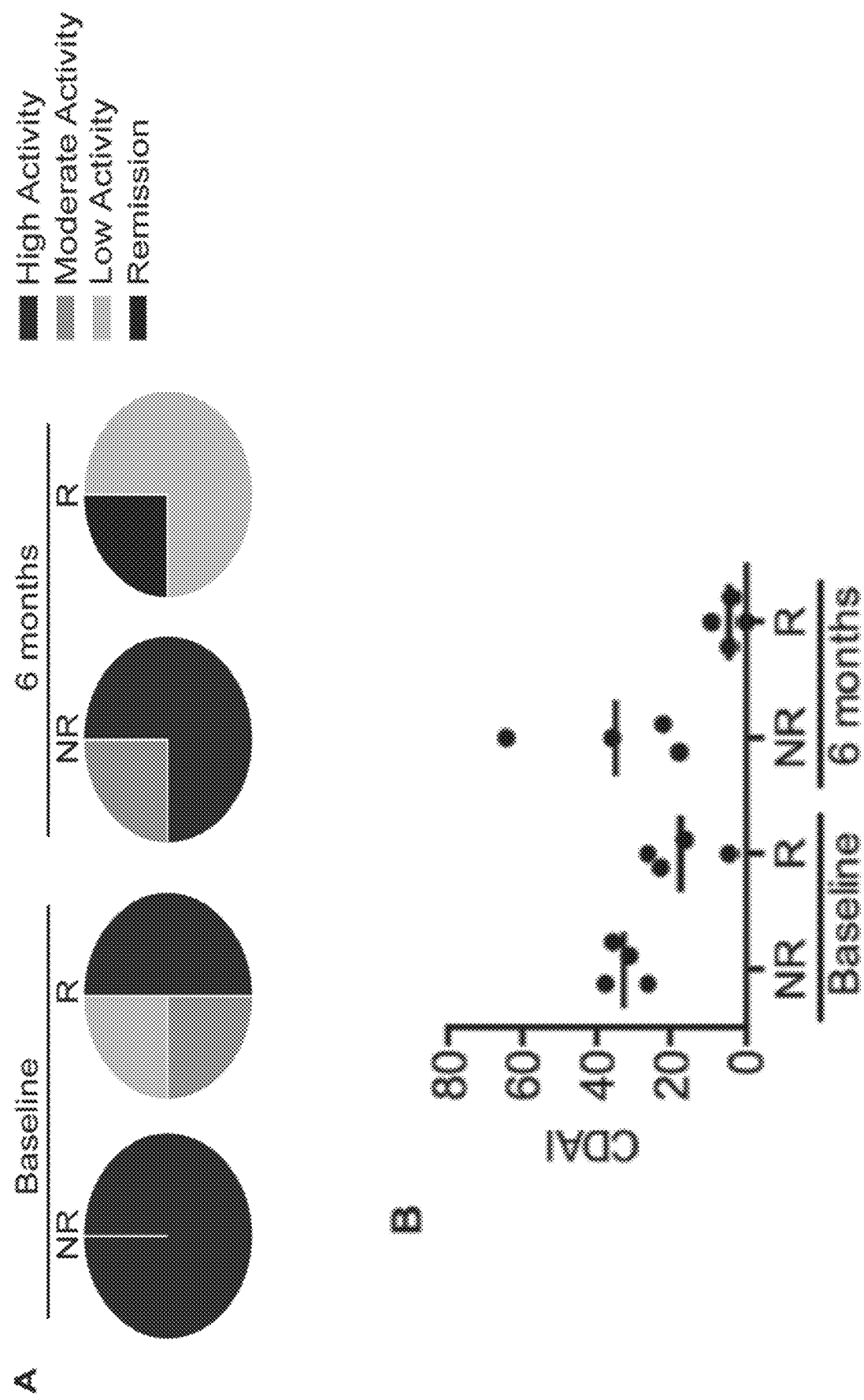
FIG. 1 is a figure comprising pie-charts and graphs relating to: Chromosome Conformation Signature EpiSwitch™ Markers discriminate MTX responders (R) from non-responders (NR). A discovery cohort of responder (R) and non-responder (NR) RA patients were selected based on DAS28 (Disease Activity Score of 28 joints) EULAR (The European League Against Rheumatism) response criteria (see methods). (A) Pie charts show the clinical interpretation of CDAI scores for both R and NR patients at baseline and 6 months. (B) CDAI scores of R and NR patients at baseline and 6 months. (C) EpiSwitch™ array analysis of peripheral blood mononuclear cells taken at diagnosis from R and NR, and healthy controls (HC) identified 922 statistically significant stratifying marker candidates. Further analysis revealed that 420 were specific for NR, 210 to R and 159 to HC. Pie charts show the proportion in relation to the 13,322 conditional chromosome conformations screened. All markers showed adjusted p<0.2. (D) Hierarchical clustering using Manhattan distance measure with complete linkage agglomeration is shown by the heatmaps. Marker selection using binary pattering across the 3 groups (R, NR and HC) initially reduced the 922 EpiSwitch™ Markers to 65 and then the top 30 markers.
Figure 1:
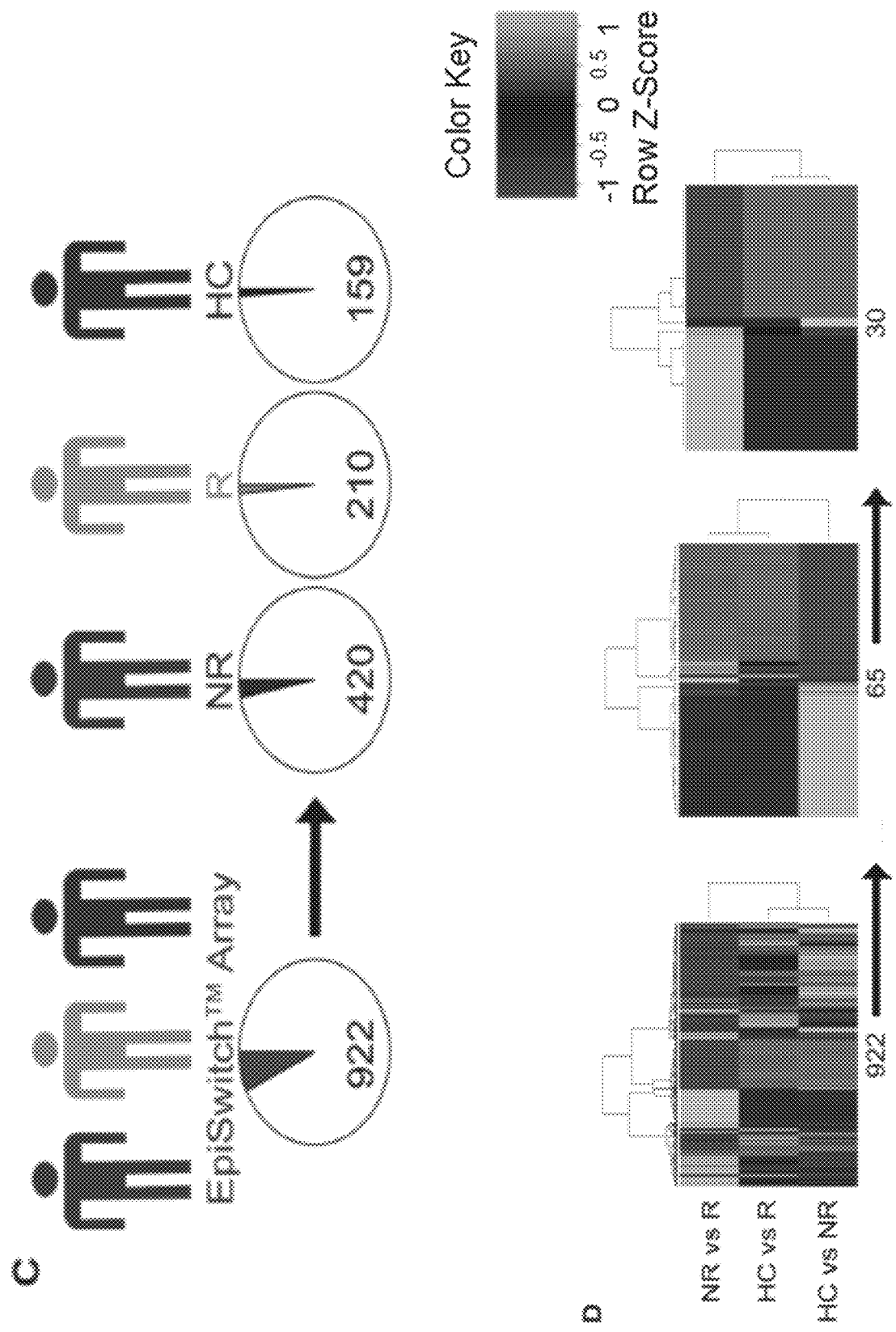

The invention has several different aspects:
- a method of determining responsiveness to a specific therapy for rheumatoid arthritis in a subject;
- a companion diagnostic method;
- a therapeutic agent for use in treatment and/or prophylaxis of an individual (specifically, in the treatment and/or prophylaxis of rheumatoid arthritis in an individual, in particular in a human individual), wherein said individual has been identified as being in need of the therapeutic agent in particular by a method of determining responsiveness and/or a companion diagnostic method of the invention;
- a method of screening for (identifying) an agent, in particular a therapeutic agent, which is capable of changing responsiveness (in particular of an individual e.g. human individual) to a therapy for rheumatoid arthritis;
- a method of determining the effect of a drug (e.g. therapeutic agent) comprising detecting the change in epigenetic chromosome interactions caused by the drug.

Epigenetic Interactions

As used herein, the term 'epigenetic' interactions typically refers to interactions between distal regions of a locus on a chromosome, said interactions being dynamic and altering, forming or breaking depending upon the status of the region of the chromosome.

In particular methods of the invention chromosome interactions are detected by first generating a ligated nucleic acid that comprises sequence(s) from both regions of the chromosomes that are part of the chromosome interactions. In such methods the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a disease condition will normally occur early in the disease process, for example compared to other epigenetic markers such as methylation or changes to binding of histone proteins. Thus the companion diagnostic method of the invention is able to detect early stages of a disease state. This allows early treatment which may as a consequence be more effective. Another advantage of the invention is that no prior knowledge is needed about which loci are relevant for identification of relevant chromosome interactions. Furthermore there is little variation in the relevant chromosome interactions between individuals within the same subgroup. Detecting chromosome interactions is highly informative with up to 50 different possible interactions per gene, and so methods of the invention can interrogate 500,000 different interactions.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions.

The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNP's within and/or outside of the genes, gene fusions and/or deletions of intergenic DNA, microRNA, and non-coding RNA. For example, it is known that roughly 20% SNPs are in non-coding regions, and therefore the method as described is also informative in non-coding situation. In one embodiment the regions of the chromosome which come together to form the interaction are less than 5 kb, 3 kb, 1 kb, 500 base pairs or 200 base pairs apart.

The chromosome interaction which is detected in the companion diagnostic method is preferably one which is within any of the genes mentioned in the Tables herein. However it may also be upstream or downstream of the genes, for example up to 50,000, 30,000, 20,000, 10,000 or 5000 bases upstream or downstream from the gene or from the coding sequence.

The chromosome interaction which is detected may or may not be one which occurs between a gene (including coding sequence) and its regulatory region, such as a promoter. The chromosome interaction which is detected may or may not be one which is inherited, for example an inherited imprinted characteristic of a gene region. The individual may be male or female. The individual may be 30 years old or older. The individual may be 29 years old or younger.

Types of Clinical Situation

The specific case of use of methotrexate (MTX) to treat RA (Rheumatoid Arthritis) illustrates the general principles. There are currently no tests that clinicians can use a priori to determine if patients will respond to MTX when the patients are first given the drug. Since a significant number (about 30%) of patients do not respond to MTX, being able to predict whether a patient is a responder or non-responder will increase the chances of successfully treating RA, as well as saving time and money.

The invention allows stratification based on biomarkers for specific phenotypes relating to rheumatoid arthritis, i.e. by recognising a particular chromosome confirmation signature and/or a change in that particular signature.

The method may or may not be used for diagnosis of the presence of rheumatoid arthritis. The methods of the invention can be used to type loci where the mechanisms of disease are unknown, unclear or complex. Detection of chromosome interactions provides an efficient way of following changes at the different levels of regulation, some of which are complex. For example in some cases around 37,000 non-coding RNAs can be activated by a single impulse.

Subgroups and Personalised Treatment

As used herein, a "subgroup" preferably refers to a population subgroup (a subgroup in a population), more preferably a subgroup in a or the population of a particular animal such as a particular mammal (e.g. human, non-human primate, or rodent e.g. mouse or rat) or a particular nematode worm (e.g. *C. elegans*). Most preferably, a "subgroup" refers to a subgroup in a or the human population.

Particular populations, e.g. human populations, of interest include: the human population overall, the human RA population (i.e. humans suffering from RA), the human healthy population (healthy controls), the human population which is healthy in the sense of not suffering from RA, the human (healthy and/or RA) population who are responders to a particular drug/therapy, or the human (healthy and/or RA) population who are non-responders to a particular drug/therapy.

The invention relates to detecting and treating particular subgroups in a population, preferably in a or the human population. Within such subgroups the characteristics discussed herein (such as responsiveness to treatment and/or prophylaxis; in particular responsiveness to a specific e.g. pharmaceutical treatment and/or prophylaxis e.g. to a therapeutically active substance/therapeutic agent e.g. pharmaceutical therapeutic agent) will be present or absent. Epigenetic interaction differences on a chromosome are, generally speaking, structural differences which exist at a genomic level. The inventors have discovered that these differ between subsets (for example two, or two or more, subsets) in a given population. Identifying these differences will allow physicians to categorize their patients as a part of one subset of the population as described in the method. The invention therefore provides physicians with a method of personalizing medicine for the patient based on their epigenetic chromosome interactions, and provide an alternative more effective treatment and/or prophylaxis regime.

In another embodiment, threshold levels for determining to what extent a subject is defined as belonging to one subgroup and not to a or the other subgroup of the population (e.g. human population, e.g. human RA population) are applied. In one preferable embodiment wherein the subgroups comprise responders versus non-responders of a therapy for the treatment of a particular disease (e.g. or i.e. RA), said threshold may be measured by change in DAS28 score (Disease Activity Score of 28 joints). In one embodiment, a score above 1.2 units indicates a subject falls into the responder subgroup, whilst a score below 1.2 units indicates a subject is defined as a non-responder.

Typically a subgroup will be at least 10%, at least 30%, at least 50%, at least 70%, or at least 80% of the general population.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

One such method, in particular one particular method of detecting chromosome interactions and/or one particular method of determining epigenetic chromosome interactions and/or one particular method of generating ligated nucleic acids (e.g. DNA), comprises the steps of:

(i) in vitro crosslinking of said epigenetic chromosomal interactions present at the chromosomal locus;

(ii) optionally isolating the cross-linked DNA from said chromosomal locus;

(iii) subjecting said cross-linked DNA to restriction digestion with an enzyme that cuts it at least once (in particular an enzyme that cuts at least once within said chromosomal locus);

(iv) ligating said cross-linked cleaved DNA ends (in particular to form DNA loops); and (v) identifying the presence of said ligated DNA and/or said DNA loops, in particular using techniques such as PCR (polymerase chain reaction), to identify the presence of a specific chromosomal interaction.

One particularly preferable method of detecting, determining and/or monitoring chromosome interactions and/or epigenetic changes, involving inter alia the above-mentioned steps of crosslinking, restriction digestion, ligating, and identifying, is disclosed in WO 2009/147386 A1 (Oxford Biodynamics Ltd), the entire disclosure of which (in particular claim 1, 2, 3, 4, 5, 6, 7, 8, 9, 10, 11, 12, 13, 14, 15, 16, 17, 18, 19, 20 or 21 of which) are incorporated herein by reference as though fully set forth. Claim 1 of WO 2009/147386 A1, which can be used in those methods of the present invention which involve a ligated product(s) and/or a ligated nucleic acid(s), discloses a method of monitoring epigenetic changes comprising monitoring changes in conditional long range chromosomal interactions at at least one chromosomal locus where the spectrum of long range interaction is associated with a specific physiological condition, said method comprising the steps of:—

(i) in vitro crosslinking of said long range chromosomal interactions present at the at least one chromosomal locus;

(ii) isolating the cross linked DNA from said chromosomal locus;

(iii) subjecting said cross linked DNA to restriction digestion with an enzyme that cuts at least once within the at least one chromosomal locus;

(iv) ligating said cross linked cleaved DNA ends to form DNA loops; and (v) identifying the presence of said DNA loops;

wherein the presence of DNA loops indicates the presence of a specific long range chromosomal interaction.

PCR (polymerase chain reaction) may be used to detect or identify the ligated nucleic acid, for example the size of the PCR product produced may be indicative of the specific chromosome interaction which is present, and may therefore be used to identify the status of the locus. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is TakaRa LA Taq polymerase.

Embodiments such as EpiSwitch™ Technology

The EpiSwitch™ Technology relates to the use of microarray EpiSwitch™ marker data in the detection of epigenetic chromosome conformation signatures specific for phenotypes. The present inventors describe herein how the EpiSwitch™ Array Platform has been used for discovery of chromosome signature pool of potential biomarkers specific for particular disadvantageous phenotypes subgroups versus healthy controls. The inventors also provide examples of validated use and translation of chromosome conformation signatures from microarray into PCR platform with examples of several markers specific between subgroups from the cohorts tested on the array.

Embodiments such as EpiSwitch™ which utilise ligated nucleic acids in the manner described herein (for identifying relevant chromosome interactions and in companion diagnostic methods) have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 hours to 6 hours.

Samples and Sample Treatment

The sample will contain DNA from the individual. It will normally contain cells. In one embodiment a sample is obtained by minimally invasive means, and may for example be blood. DNA may be extracted and cut up with standard restriction enzymes. This can pre-determine which chromosome conformations are retained and will be detected with the EpiSwitch™ platforms. In one embodiment wherein the sample is a blood sample previously obtained from the patient, the described method is advantageous because the procedure is minimally invasive. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic acids of the invention

The disclosure herein mentions first and second nucleic acids. In addition the nucleic acids are used in the companion diagnostic method and in other embodiments to detect the presence or absence of chromosome interactions (for example by binding to ligated nucleic acids generated from samples). The nucleic acids of the invention typically comprise two portions each comprising sequence from one of the two regions of the chromosome which come together in the chromosome interaction. Typically each portion is at least 8, 10, 15, 20, 30 or 40 nucleotides in length. Preferred nucleic acids comprise sequence from any of the genes mentioned in the tables, in particular where the nucleic acid is used in embodiments relevant to the condition relevant for that table. Preferred nucleic acids comprise the specific probe sequences mentioned in the tables for specific conditions or fragments or homologues of such sequences. Preferably the nucleic acids are DNA. It is understood that where a specific sequence is provided the invention may use the complementary as required in the particular embodiment.

The Second Set of Nucleic Acids—the 'Index' Sequences

The second set of nucleic acid sequences has the function of being an index, and is essentially a set of nuclei acid sequences which are suitable for identifying subgroup specific sequence. They can represents the 'background' chromosomal interactions and might be selected in some way or be unselected. They are a subset of all possible chromosomal interactions.

The second set of nucleic acids may be derived by any suitable method. The can be derived computationally or they may be based on chromosome interaction in individuals. They typically represent a larger population group than the first set of nucleic acids. In one embodiment, the second set of nucleic acids represents all possible epigenetic chromosomal interactions in a specific set of genes. In another embodiment, the second set of nucleic acids represents a large proportion of all possible epigenetic chromosomal interactions present in a population described herein. In one embodiment, the second set of nucleic acids represents at least 50% or at least 80% of epigenetic chromosomal interactions in at least 20, 50, 100 or 500 genes.

The second set of nucleic acids typically represents at least 100 possible epigenetic chromosome interactions which modify, regulate or any way mediate a disease state/phenotype in population. The second set of nucleic acids may represent chromosome interactions that affect a diseases state in a species, for example comprising nucleic acids sequences which encode cytokines, kinases, or regulators associated with any disease state, predisposition to a disease or a disease phenotype. The second set of nucleic acids comprises sequences representing epigenetic interactions relevant and not relevant to the companion diagnostic method.

In one embodiment the second set of nucleic acids derive at least partially from naturally occurring sequences in a population, and are typically obtained by in silico methods. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one embodiment, the second set of nucleic acids may comprise sequence representing a homologue and/or orthologue with at least 70% sequence identity to the corresponding portion of nucleic acids present in the naturally occurring species. In another embodiment, at least 80% sequence identity or at least 90% sequence identity to the corresponding portion of nucleic acids present in the naturally occurring species is provided.

Properties of the Second Set of Nucleic Acids

In one embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All or at least 90% or at least 50% or these would correspond to different chromosomal interactions.

In one embodiment, the second set of nucleic acids represent chromosome interactions in at least different loci or genes, preferably at least 40 different loci or genes, and more preferably at least 100, at least 500, at least 1000 or at least 5000 different loci or genes, such as 100 to 10,000 different loci or genes.

The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different disease characteristics.

The First Set of Nucleic Acids

The first set of nucleic acids are normally from individuals known to be in two or more distinct subgroups defined by presence or absence of a characteristic relevant to a companion diagnostic, such as any such characteristic mentioned herein. The first nucleic acids may have any of the characteristics and properties of the second set of nucleic acids mentioned herein. The first set of nucleic acids is normally derived from a sample from the individuals which has undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Library of Nucleic Acids

The invention provides a library of nucleic acids which comprises at least 200, 500, 1000, 5000 or at least 10,000 different nucleic acids from the second set of nucleic acids. The invention provides a particular library of nucleic acids which typically comprises at least 200 different nucleic acids. The library of nucleic acids may have any of the characteristics or properties of the second set of nucleic acids mentioned herein. The library may be in the form of nucleic acids bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light.

The pattern of hybridisation, for example on an array described herein, represents differences in epigenetic chromosome interactions between the two subgroups, and thus provides a method of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Companion Diagnostic Method The invention provides a companion diagnostic method based on information provided by chromosome interactions. Two distinct companion diagnostic methods are provided which identify whether an individual has a particular characteristic relevant to a companion diagnostic. One method is based on typing a locus in any suitable way and the other is based on detecting the presence or absence of chromosome interactions. The characteristic may be any one of the characteristics mentioned herein relating to a condition. The companion diagnostic method can be carried out at more than one time point, for example where monitoring of an individual is required.

Companion Diagnostic Method Based on Typing a Locus

The method of the invention which identified chromosome interactions that are specific to subgroups can be used to identity a locus, which may be a gene that can be typed as the basis of companion diagnostic test. Many different gene-related effects can lead to the same chromosome interaction occurring. In this embodiment any characteristic of the locus may be typed, such as presence of a polymorphism in the locus or in an expressed nucleic acid or protein, the level of expression from the locus, the physical structure of the locus or the chromosome interactions present in the locus. In one particular embodiment the locus may be any of the genes mentioned herein in the tables, in particular in Tables 1, 3, 7, 8 and/or 9 (in particular Tables 1 and/or 3), or any property of a locus which is in the vicinity of a chromosome interaction found to be linked to the relevant condition.

Companion Diagnostic Method Based on Detecting Chromosome Interactions

The invention provides a companion diagnostic method which comprises detecting the presence or absence of chromosome interactions, typically 5 to 20 or 5 to 500 such interactions, preferably 20 to 300 or 50 to 100 interactions, in order to determine the presence or absence of a characteristic in an individual. Preferably the chromosome interactions are those in any of the genes mentioned herein. In one particular embodiment the chromosome interactions which are typed are those represented by the nucleic acids disclosed in the tables herein, in particular in in Tables 7a, 8a and/or 9, for example when the method is for the purpose of determining the presence or absence of characteristics defined in those tables.

Specific Conditions

The companion diagnostic method can be used to detect the presence of any of the specific conditions or characteristics mentioned herein. The companion diagnostic method can be used to detect responsiveness to methotrexate in rheumatoid arthritis patients.

Preferably the presence or absence of any of the chromosome interactions within any of the relevant genes mentioned in the tables is detected. For example in at least 1, 3, 10, 20, 50 of the genes mentioned in any one of the tables. Preferably the presence or absence of chromosome interactions represented by the probes sequences in the Tables I s determined in the method. For example at least 1, 3, 10, 20, 50, or 100 of the relevant chromosome interactions from any one of the tables. These numbers of genes or chromosome interactions can be used in any of the different embodiments mentioned herein.

The Individual Tested Using the Companion Diagnostic Method

The individual to be tested may or may not have any symptoms of any disease condition or characteristic mentioned herein. The individual may be at risk of any such condition or characteristic. The individual may have recovered or be in the process of recovering from the condition or characteristic. The individual is preferably a mammal, such as a primate, human or rodent.

Screening Method

A method of identifying a substance which is capable of changing in an individual a non-responsive state to a responsive state to a therapeutic agent for rheumatoid arthritis comprising determining whether a candidate agent is capable of changing the chromosomal interactions from those corresponding to a non-responsive state to those which correspond to a responsive state.

In one particular embodiment the method determines whether a candidate agent is capable of changing any chromosomal interaction mentioned herein.

The method may be carried out in vitro (inside or outside a cell) or in vivo (upon a non-human organism). In one particular embodiment the method is carried out on a cell, cell culture, cell extract, tissue, organ or organism, such as one which comprises the relevant chromosome interaction(s). The method is typically carried out by contacting (or administering) the candidate agent with the gene, cell, cell culture, cell extract, tissue, organ or organism.

Suitable candidate substances which tested in the above screening methods include antibody agents (for example, monoclonal and polyclonal antibodies, single chain antibodies, chimeric antibodies and CDR-grafted antibodies). Furthermore, combinatorial libraries, defined chemical identities, peptide and peptide mimetics, oligonucleotides and natural agent libraries, such as display libraries (e.g. phage display libraries) may also be tested. The candidate substances may be chemical compounds, which are typically derived from synthesis around small molecules which may have any of the properties of the agent mentioned herein.

Preferred Loci, Genes and Chromosome Interactions

For all aspects of the invention preferred loci, genes and chromosome interactions are mentioned in the tables. For all aspects of the invention preferred loci, genes and chromosome interactions are provided in the tables. Typically the methods chromosome interactions are detected from at least 1, 3, 10, 20, 30 or 50 of the relevant genes listed in the table. Preferably the presence or absence pf at least 1, 3, 10, 20, 30 or 50 of the relevant specific chromosome interactions represented by the probe sequences in any one table is detected.

The loci may be upstream or downstream of any of the genes mentioned herein, for example 50 kb upstream or 20 kb downstream.

Preferred Embodiments for Sample Preparation and Chromosome Interaction Detection Methods of preparing samples and detecting chromosome conformations are described herein.

Optimised (non-conventional) versions of these methods can be used, for example as described in this section.

Typically the sample will contain at least $2\times10^5$ cells. The sample may contain up to $5\times10^5$ cells. In one embodiment, the sample will contain $2\times10^5$ to $5.5\times10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55°

C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

Homologues

Homologues of polynucleotide/nucleic acid (e.g. DNA) sequences are referred to herein. Such homologues typically have at least 70% homology, preferably at least 80, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to % sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG Package provides the BESTFIT program which can be used to calculate homology and/or % sequence identity (for example used on its default settings) (Devereux et al (1984) Nucleic Acids Research 12, p387-395). The PILEUP and BLAST algorithms can be used to calculate homology and/or % sequence identity and/or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent SurePrint G3 Custom CGH microarray platform. Detection of binding of first nucleic acids to the array may be performed by a dual colour system.

Therapeutic Agents

Therapeutic agents are mentioned herein. The invention provides such agents for use in preventing or treating the relevant condition. This may comprise administering to an individual in need a therapeutically effective amount of the agent. The invention provides use of the agent in the manufacture of a medicament to prevent or treat the disease. The methods of the invention may be used to select an individual for treatment. The methods of the invention, and in particular the method for carrying out a companion diagnostic test, may include a treatment step where a person identified by the method may then be administered with an agent that prevents or treats the relevant condition.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

Forms of the Substance Mentioned Herein

Any of the substances, such as nucleic acids or therapeutic agents, mentioned herein may be in purified or isolated form. The may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all the of specific nucleic acid sequences mentioned herein in single or double stranded form, and thus includes the complementary strand to any sequence which is disclosed.

The invention also provides a kit for carrying out any method of the invention, including detection of a chromosomal interaction associated with a particular subgroup. Such a kit can include a specific binding agent capable of detecting the relevant chromosomal interaction, such as agents capable of detecting a ligated nucleic acid generated by methods of the invention. Preferred agents present in the kit include probes capable of hybridising to the ligated nucleic acid or primer pairs, for example as described herein, capable of amplifying the ligated nucleic acid in a PCR reaction.

The invention also provides a device that is capable of detecting the relevant chromosome interactions. The device preferably comprises any specific binding agents, probe or primer pair capable of detecting the chromosome interaction, such as any such agent, probe or primer pair described herein.

PUBLICATIONS

The contents of all publications mentioned herein are incorporated by reference into the present specification and may be used to further define the features relevant to the invention.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalization of the arrays is done using the normalized within Arrays function in Limma* and this done to the on chip Agilent positive controls and EpiSwitch™ positive controls. The data is filtered based on the Agilent Flag calls, the Agilent control probes are removed and the technical replicate probes are averaged, in order for them to be analyzed using Limma*. The probes are modelled based on their difference between the 2 scenarios being compared and then corrected by using False Discover rate. Probes with Coefficient of Variation (CV) <30% that are <1 or >1 and pass the p=0.01 FDR p-value are used for further screening. To reduce the probe set further Multiple Factor Analysis is performed using the FactorMineR package in R.

*Note: LIMMA is Linear Models and Empirical Bayes Methods for Assessing Differential Expression in Microarray Experiments. Limma is a R package for the analysis of gene expression data arising from microarray or RNA-Seq.

The pool of probes is initially selected based on adjusted p-value, FC and CV <30% (arbitrary cut off point) parameters for final picking. Further analyses and the final list are drawn based only on the first two parameters (adj p-value; FC).

Publications

The contents of all publications mentioned herein are incorporated by reference into the present specification and may be used to further define the features relevant to the invention.

Specific Embodiments

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalisation of the arrays is done using the normalised within Arrays function in Limma* and this is done to the on chip Agilent positive controls and EpiSwitch™ positive controls. The data is filtered based on the Agilent Flag calls, the Agilent control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV) <=30% that are <=−1.1 or =>1.1 and pass the p<=0.1 FDR p-value are used for further screening. To reduce the probe set further Multiple Factor Analysis is performed using the FactorMineR package in R.

*Note: LIMMA is Linear Models and Empirical Bayes Methods for Assessing Differential Expression in Microarray Experiments. Limma is a R package for the analysis of gene expression data arising from microarray or RNA-Seq.

The pool of probes is initially selected based on adjusted p-value, FC and CV <30% (arbitrary cut off point) parameters for final picking. Further analyses and the final list are drawn based only on the first two parameters (adj p-value; FC).

EXAMPLES

The invention is illustrated by the following non-limiting Examples.

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1 Probes are selected based on their corrected p-value (False Discovery Rate, FDR), which is the product of a modified linear regression model. Probes below p-value <=0.1 are selected and then further reduced by their Epigenetic ratio (ER), probes ER have to be <=−1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Example 1: A Method of Determining the Chromosome Interactions which are Relevant to a Companion Diagnostic that Distinguishes Between Non-Responders and Responders of Methotrexate for the Treatment of Rheumatoid Arthritis Source: Glasgow Scottish Educational Research Association (SERA) cohort.

Introduction to and Brief Summary of Example 1

Stable epigenetic profiles of individual patients modulate sensitivity of signalling pathways, regulate gene expression, influence the paths of disease development, and can render ineffective the regulatory controls responsible for effective action of the drug and response to treatment. Here we analysed epigenetic profiles of rheumatoid arthritis (RA) patients in order to evaluate its role in defining the non-responders to Methotrexate (MTX) treatment.

Reliable clinical prediction of response to first-line disease modifying anti-rheumatic drugs (DMARDs, usually methotrexate (MTX)) in rheumatoid arthritis is not currently possible. Currently the ability to determine response to first line DMARDs (in particular, methotrexate (MTX) is dependent on empiric clinical measures after the therapy.

In early rheumatoid arthritis (ERA), it has not been possible to predict response to first line DMARDs (in particular methotrexate (MTX)) and as such treatment decisions rely primarily on clinical algorithms. The capacity to classify drug naïve patients into those that will not respond to first line DMARDs would be an invaluable tool for patient stratification. Here we report that chromosome conformational signatures (highly informative and stable epigenetic modifications that have not previously been described in RA) in blood leukocytes of early RA patients can predict non-responsiveness to MTX treatment.

Methods:

Peripheral blood mononuclear cells (PBMCs) were obtained from DMARD naïve ERA patients recruited in the Scottish early rheumatoid arthritis (SERA) inception cohort. Inclusion in this study was based on diagnosis of RA (fulfilling the 2010 ACR/EULAR Criteria) with moderate to high disease activity (DAS28 ≥3.2) and subsequent monotherapy with methotrexate (MTX). DAS28=Disease Activity Score of 28 joints. EULAR=The European League Against Rheumatism. ACR=American College of Rheumatology. MTX responsiveness was defined at 6 months using the following criteria: Responders—DAS28 remission (DAS28 <2.6) or a good response (DAS28 improvement of >1.2 and DAS28 3.2). Non-responders—no improvement in DAS28 (≤16). Initial analysis of chromosome conformational signatures (CCS) in 4 MTX responders, 4 MTX non-responders and 4 healthy controls was undertaken using an EpiSwitch™ array containing 13,322 unique probes covering 309 RA-related genetic loci. Differentiating CCS were defined by LIMMA* linear modeling, subsequent binary filtering and cluster analysis. A validation cohort of 30 MTX responders and 30 non-responders were screened for the differentiating CCS using the EpiSwitch™ PCR platform. The differentiating signature was further refined using binary scores and logistical regression modeling, and the accuracy and robustness of the model determined by ROC** analysis.

* Note: LIMMA is Linear Models and Empirical Bayes Methods for Assessing Differential Expression in Microarray Experiments. Limma is a R package for the analysis of gene expression data arising from microarray or RNA-Seq.

** Note: ROC means Receiver Operating Characteristic and refers to ROC curves. An ROC curve is a graphical plot that illustrates the performance of a binary classifier system as its discrimination threshold is varied. The curve is created by plotting the true positive rate against the false positive rate at various threshold settings.

CCS EpiSwitch™ array analysis identified a 30-marker stratifying profile differentiating responder and non-responder ERA patients. Subsequent evaluation of this signature in our validation cohort refined this to a 5-marker CCS signature that was able to discriminate responders and non-responders. Prediction modeling provided a probability score for responders and non-responders, ranging from 0.0098 to 0.99 (0=responder, 1=non-responder). There was a true positive rate of 92% (95% confidence interval [95% CI] 75-99%) for responders and a true negative rate of 93% (95% CI 76-99%) for non-responders. Importantly; ROC analysis to validate this stratification model demonstrated that the signature had a predictive power of sensitivity at 92% for NR to MTX.

We have identified a highly informative systemic epigenetic state in the peripheral blood of DMARD naïve ERA patients that has the power to stratify patients at the time of diagnosis. The capacity to differentiate patients a priori into non-responders, using a blood-based clinical test, would be an invaluable clinical tool; paving the way towards stratified medicine and justifying more aggressive treatment regimes in ERA clinics.

Detailed Version of Example 1

The capacity to differentiate patients a priori into responders (R) and non-responders (NR) would be an invaluable tool for patient stratification leading to earlier introduction of effective treatment. We have used the EpiSwitch™ biomarker discovery platform to identify Chromosome Conformation Signatures (CCS) in blood-derived leukocytes, which are indicative of disease state and MTX responsiveness. Thereby we identified an epigenetic signature contained in the CXCL13, IFNAR1, IL-17A, IL-21R and IL-23 loci that provide the first prognostic molecular signature that enables the stratification of treatment naïve early RA (ERA) patients into MTX R and NR. Importantly, this stratification model had a predictive power of sensitivity at 92% for NR to MTX. This epigenetic RA biomarker signature can distinguish between ERA and healthy controls (HC). This combinatorial, predictive peripheral blood signature can support earlier introduction of more aggressive therapeutics in the clinic, paving the way towards personalized medicine in RA.

RA is a chronic autoimmune disease affecting up to 1% of the global population. Pathogenesis is multifactorial and characterized by primarily immune host gene loci interacting with environmental factors, particularly smoking and other pulmonary stimuli[1,2,3]. The exposure of a genetically susceptible individual to such environmental factors suggests an epigenetic context for disease onset and progression. Recent studies of chromatin markers (e.g. methylation status of the genome) provide the first evidence of epigenetic differences associated with RA[4,5,6,7]. However, to date neither genetic associations, nor epigenetic changes, have provided a validated predictive marker for response to a given therapy. Moreover, clinical presentation only weakly predicts the efficacy and toxicity of conventional DMARDs. MTX[8], the commonest first-choice medication recommended by EULAR (The European League Against Rheumatism) and ACR (American College of Rheumatology) management guidelines, delivers clinically meaningful response rates ranging from 50 to 65% after 6 months of treatment[11]. Such responses, and especially the rather smaller proportion that exhibits high hurdle responses, cannot currently be predicted in an individual patient. This begets a 'trial and error' based approach to therapeutic regimen choice (mono or combinatorial therapeutics). The ability to predict drug responsiveness in an individual patient would be an invaluable clinical tool, given that response to first-line treatment is the most significant predictor of long-term outcome[9,10].

Herein we focused on epigenetic profiling of DMARD-naïve, ERA patients from the Scottish Early Rheumatoid Arthritis (SERA) inception cohort in order to ascertain if there is a stable blood-based epigenetic profile that indicates NR to MTX treatment and thus enables a priori identification and stratification of such patients to an alternate therapeutic. The source Epigenetic modulation can strongly influence cellular activation and transcriptional profiles. Conceivably; the mode of action for a drug could be affected by epigenetically modified loci. We have focused on CCS, also known as long-range chromatin interactions, because they reflect highly informative and stable high-order epigenetic status which have significant implications for transcriptional regulation[12,13,14]. They also offer significant advantages[15] and early functional links to phenotypic differences[16], and have been reported as informative biomarkers candidates in oncology and other disease areas[17,18,19].

We used early RA (ERA) patients provided by the Scottish early rheumatoid arthritis (SERA) inception cohort. Demographic, clinical and immunological factors were obtained at diagnosis and 6 months. Inclusion in this study was based on a diagnosis of RA (fulfilling the 2010 ACR/EULAR Criteria) with moderate to high disease activity (DAS28 3.2) and subsequent monotherapy with MTX. Responders were defined as patients who upon receiving MTX achieved DAS28 remission (DAS28 <2.6) or a good response (DAS28 improvement of >1.2 and DAS28 3.2) at 6 months. Non-responders were defined as patients who upon receiving MTX had no improvement in DAS28 (0.6) at 6 months. Blood samples for epigenetic analysis were collected at diagnosis. (DAS28=Disease Activity Score of 28 joints.)

We used a binary epigenetic biomarker profiling by analysing over 13,322 chromosome conformation signatures (CCS) (13,322 unique probes) across 309 genetic loci functionally linked to RA. CCS, as a highly informative class of epigenetic biomarkers (1), were read, monitored and evaluated on EpiSwitch™ platform which has been already successfully utilized in blood based stratifications of Mayo Clinic cohort with early melanoma (2) and is currently used for predictive stratification of responses to immunotherapies with PD-1/PD-L1.

Identified epigenetic profiles of naïve RA patients were subject to statistical analysis using GraphPad Prism, WEKA and R Statistical language. By using EpiSwitch™ platform and extended cohort of 90 clinical samples we have identified a pool of over 922 epigenetic lead biomarkers, statistically significant for responders, non-responders, RA patients and healthy controls.

To identify a pre-treatment circulating CCS status in ERA patients, 123 genetic loci (Table 1) associated with RA pathogenesis were selected and annotated with chromosome conformations interactions predicted using the EpiSwitch™ in silico prediction package[20]. The EpiSwitch™ in silico prediction generated 13,322 high-confidence CCS marker candidates (Table 1). These candidates were used to generate a bespoke discovery EpiSwitch™ array (FIG. 5) to screen peripheral blood mononuclear cells isolated at the time of diagnosis (DMARD-naïve) from 4 MTX responders (R) and 4 MTX NR, all clinically defined after 6 months therapy (FIG. 1A, B and Table 2), and 4 healthy controls (HC). To identify the CCS that differentiated R, NR and HC, a LIMMA linear model of the normalized epigenetic load was employed. A total of 922 statistically significant stratifying markers (significance assessed on the basis of adjusted p value and EpiSwitch™ Ratio) were identified. Of the 922 lead markers, 420 were associated with NR, 210 with R and 159 with HC (FIG. 1C). Binary filtering and cluster analysis was applied to the EpiSwitch™ markers to assess the significance of CCS identified. A stepwise hierarchical clustering approach (using Manhattan distance measure with complete linkage agglomeration and taking into account R vs NR, HC vs R & HC vs NR) reduced the number of significant markers from 922 to 65 and finally resulted in a 30-marker stratifying profile (FIG. 1D and Table 3).

Figure 2:
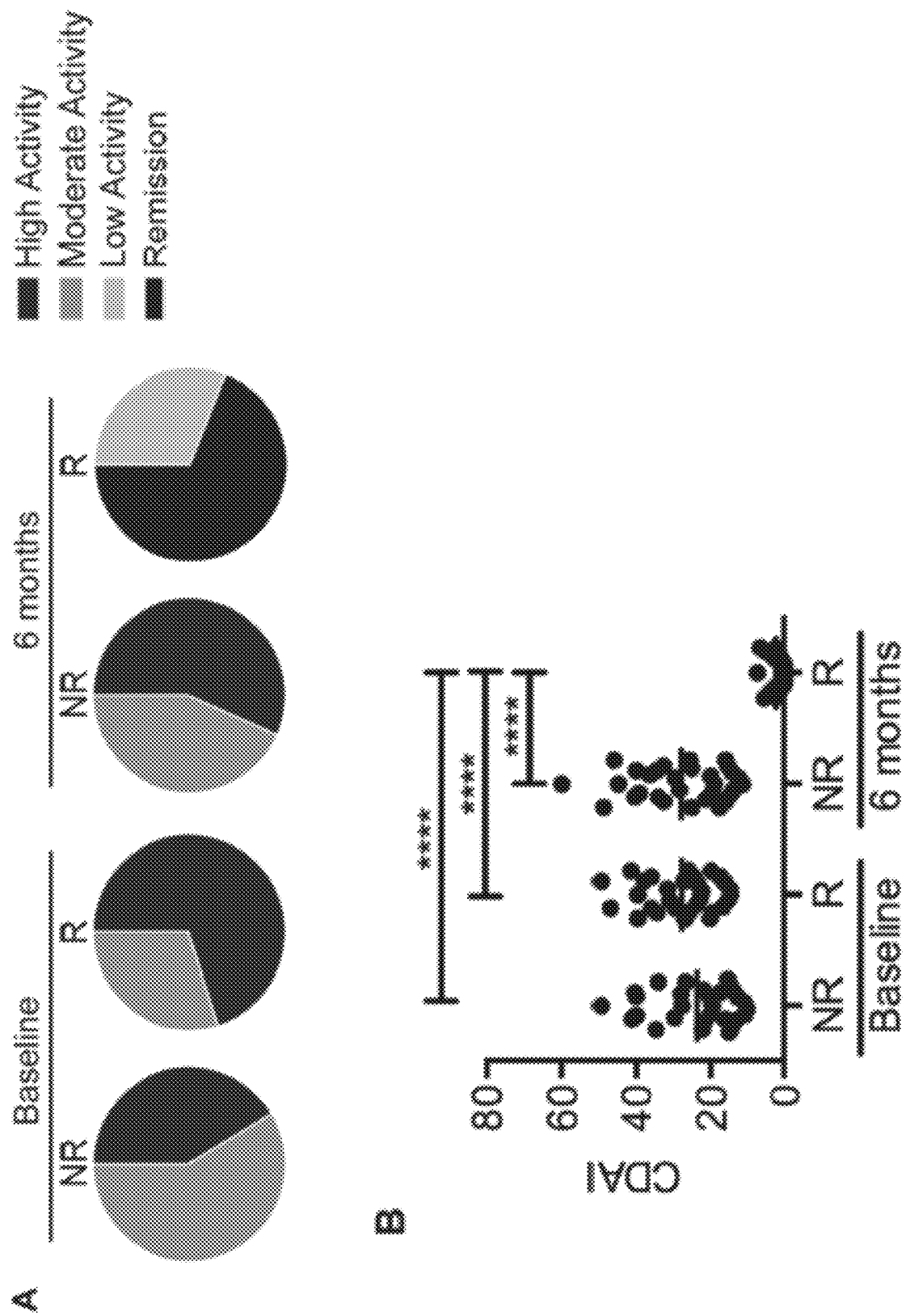
FIG. 2 is a figure comprising pie-charts and graphs relating to: Refinement and validation of the Chromosome Conformation Signature EpiSwitch™ Markers. The validation cohort of responder (R) and non-responder (NR) RA patients were selected based on DAS28 (Disease Activity Score of 28 joints) EULAR (The European League Against Rheumatism) response criteria (see methods). (A) Pie charts show the clinical interpretation of CDAI scores for both R and NR patients at baseline and 6 months. (B) CDAI scores of R and NR patients at baseline and 6 months. ****P<0.0001 by Kruskal-Wallis test with Dunn's multiple comparison post test (C) Correlation plot of the classifying 5 EpiSwitch™ markers. The red box indicates the markers that define NR whilst the orange box indicated markers that define R. (D) Principle Component Analysis (PCA) for a 60 patient cohort based on their binary scores for the classifying 5 EpiSwitch™ markers.
Figure 2:
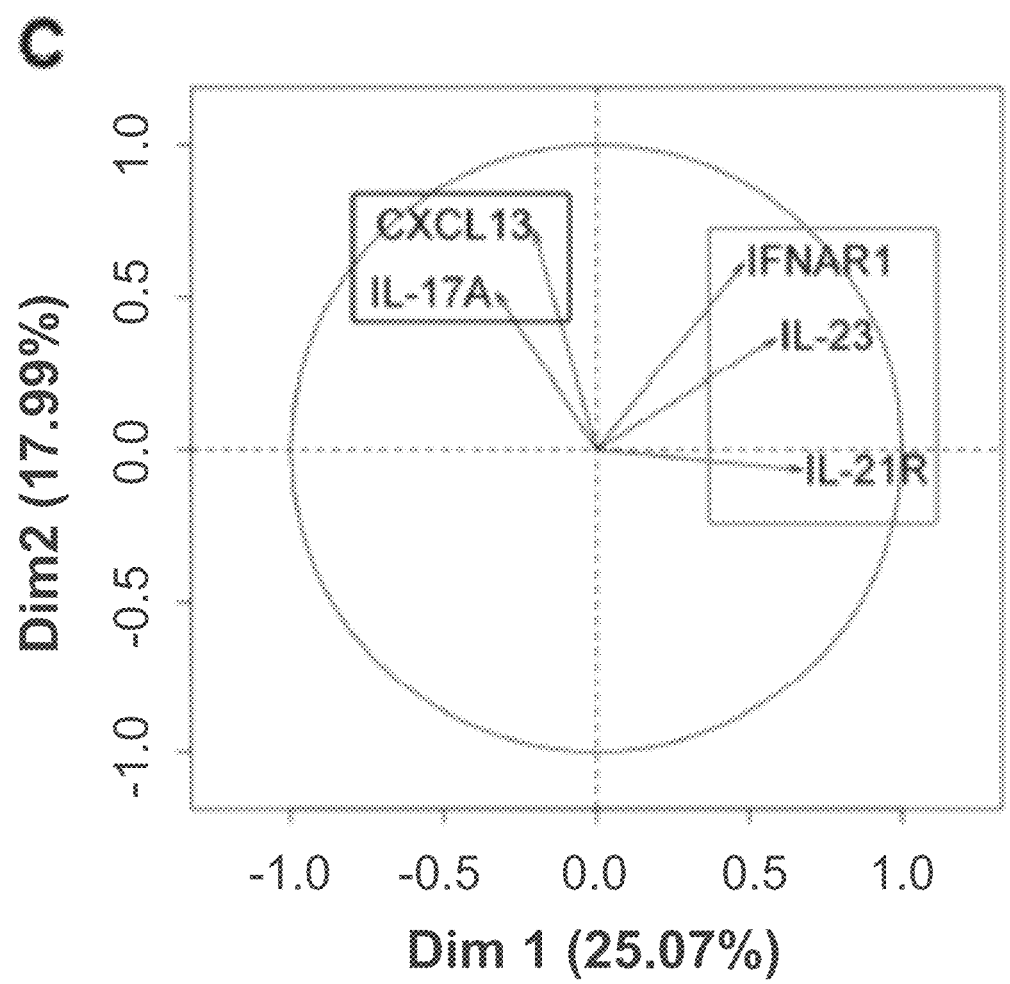
Figure 2:
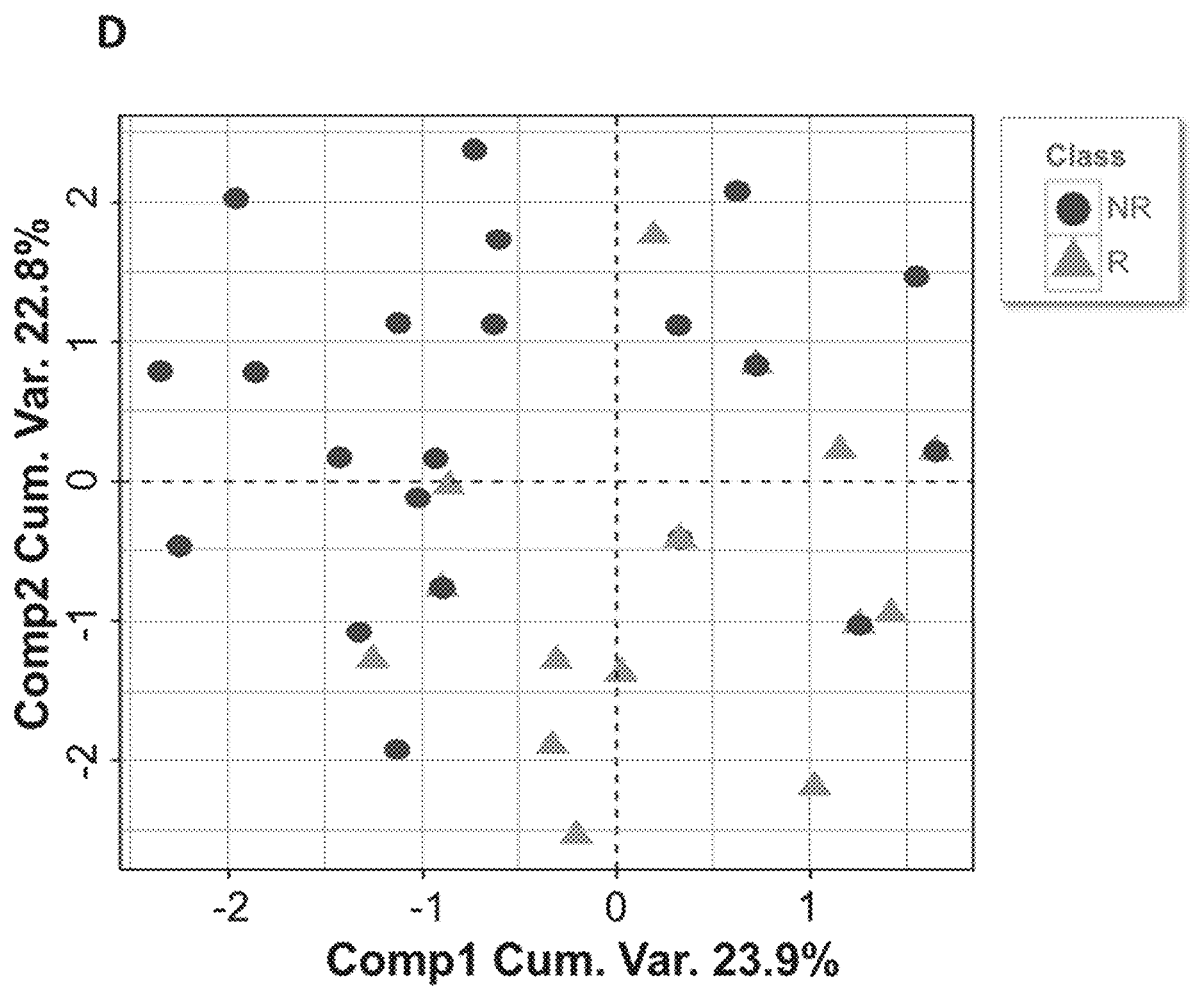
Figure 5:
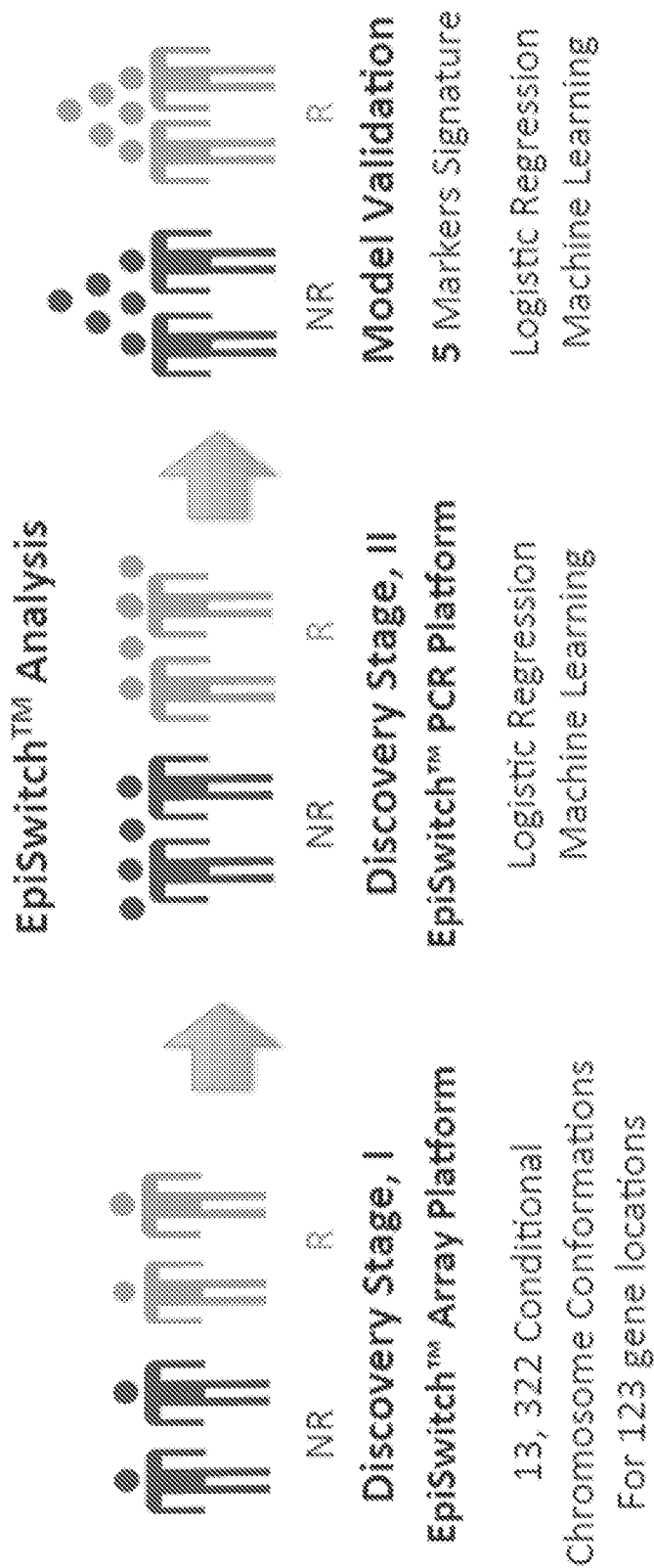
FIG. 5 is a Scheme illustrating the Design for Discovery and Validation of Epigenetic Stratifying Biomarker Signature for DMARDS Naïve ERA patients, who were confirmed within 6 months of MTX treatment as responders (N) or non-responders (NR). Epigenetic stratification was based on conditional chromosome confirmations screened and monitored by EpiSwitch™ Array and PCR (polymerase chain reaction) platforms. Disease specific epigenetic nature of the identified biomarkers was confirmed by stratification against healthy controls (HC). Validation was performed on 60 RA patients (30 responders and 30 non-responders) and 30 HC.

To refine and validate the CCS signature, the 30 identified markers were screened in a second ERA patient cohort of R and NR (FIG. 2A, B and Table 4) in a stepwise approach, using the EpiSwitch™ PCR platform (FIG. 5). In the first instance, the entire 30 CCS markers were run in 12 ERA patients (6 R and 6 NR). The best differentiating CCS markers were identified by applying a Chi-squared test for independence with Yate's continuity correction on the binary scores, revealing a 12-marker CCS profile (Table 5). These 12 CCS markers were run on an additional 12 ERA patients (6 R and 6 NR) and the data combined with the previous 12 ERA. Combining the 24 patient samples (12 R and 12 NR) a logistic regression Model in the WEKA classification platform (using 5-fold cross validation to score the discerning power of each marker) was built and run 10 times by random data re-sampling of the initial data set to generate 10 different start points for model generation. The markers with the highest average scores were selected, thus reducing the profile to the 10 best discerning CCS markers (Table 5). The 10 CCS markers were used to probe a further 36 ERA samples (18 R and 18 NR). Combining all data (30 R and 30 NR), and using the same logistical regression and score calculation analysis, revealed a 5 CCS marker signature (IFNAR1, IL-21R, IL-23, IL-17A and CXCL13) that distinguished MTX R from NR (FIG. 2C, and Table 5). CCS in the CXCL13 and IL-17A loci were associated with non-responders whilst CCS in the IFNAR1, IL-23 and IL-21R loci were associated with responders. This was an intriguing profile given the central role postulated for the IL-17 axis in human autoimmunity.

Importantly, the composition of the stratifying signature identifies the location of chromosomal conformations that potentially control genetic locations of primary importance for determining MTX response. Principal component analysis (PCA) of the binary scores for the classifying 5 EpiSwitch™ CCS markers provided clear separation of ERA patients based on their MTX response (FIG. 2D). The model provided a prediction probability score for responders and non-responders, ranging from 0.0098 to 0.99 (0=responder, 1=non-responder). The cut-off values were set at 0.30 for responders and ≥0.70 for non-responders. The score of 0.30 had a true positive rate of 92% (95% confidence interval [95% CI] 75-99%) whilst a score of 0.70 had a true negative response rate of 93% (95% CI 76-99%). The number of observed and predicted patients per response category (R or NR to MTX) is shown in Table 6. With the EpiSwitch™ CCS marker model, 53 patients (88%) were classified as either responder or non-responder.

TABLE 6

Observed and predicted number of R and NR to MTX monotherapy at 6 months using the EpiSwitch ™ CCS model

| Observed response | Predicted response | | |
|---|---|---|---|
| | Non-responder | Undefined | Responder |
| Non-responder | 25 | 3 | 2 |
| Responder | 2 | 4 | 24 |

Notes to Table 6:
Cut off levels were chosen based on the probability of response to MTX of (approximately) >0.70 for NR and <0.3 for R. NR and R were defined as described in the methods.

Figure 3:
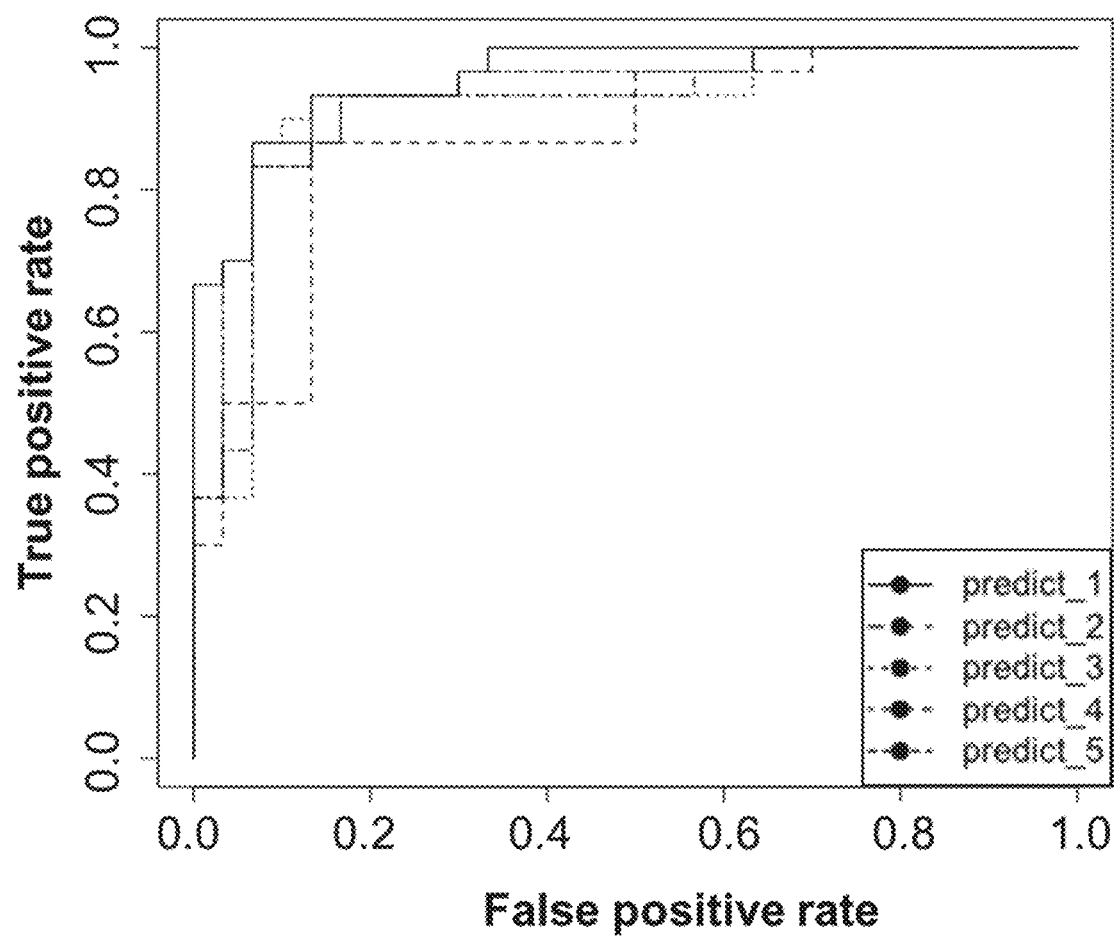
FIG. 3 is a figure comprising graphs relating to: Prognostic stratification and model validation for response to methotrexate (MTX) treatment. (A) Representative examples of 5 selected Receiver Operating Characteristics (ROC) curves from 150 randomisations of the data using the 5 CCS marker logistic regression classifiers. (B) Factor Analysis for responder (R) and non-responder (NR) RA patients vs healthy controls (HC) using EpiSwitch™ CCS markers selected for discerning MTX responders from MTX non-responders.
Figure 3:
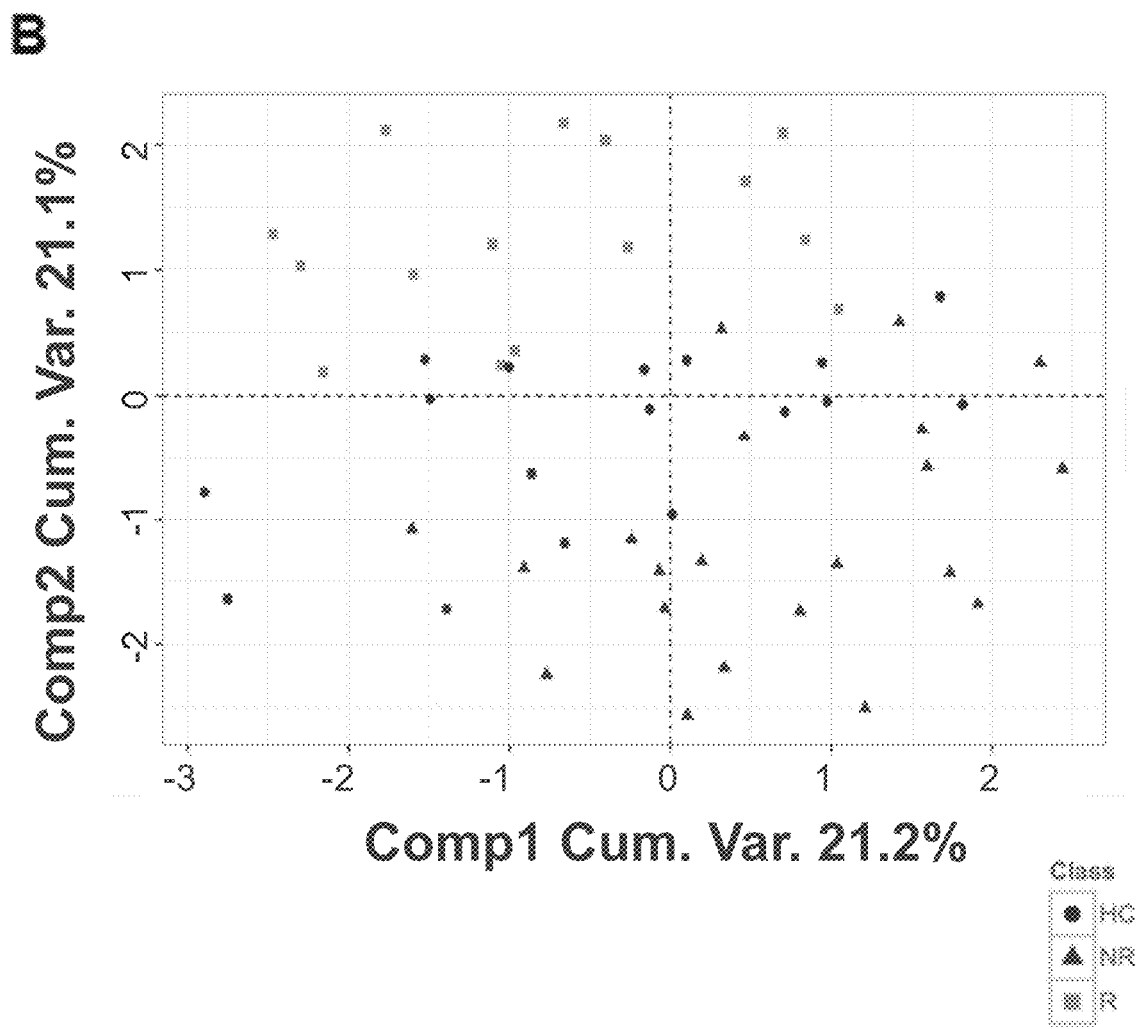
Figure 4:
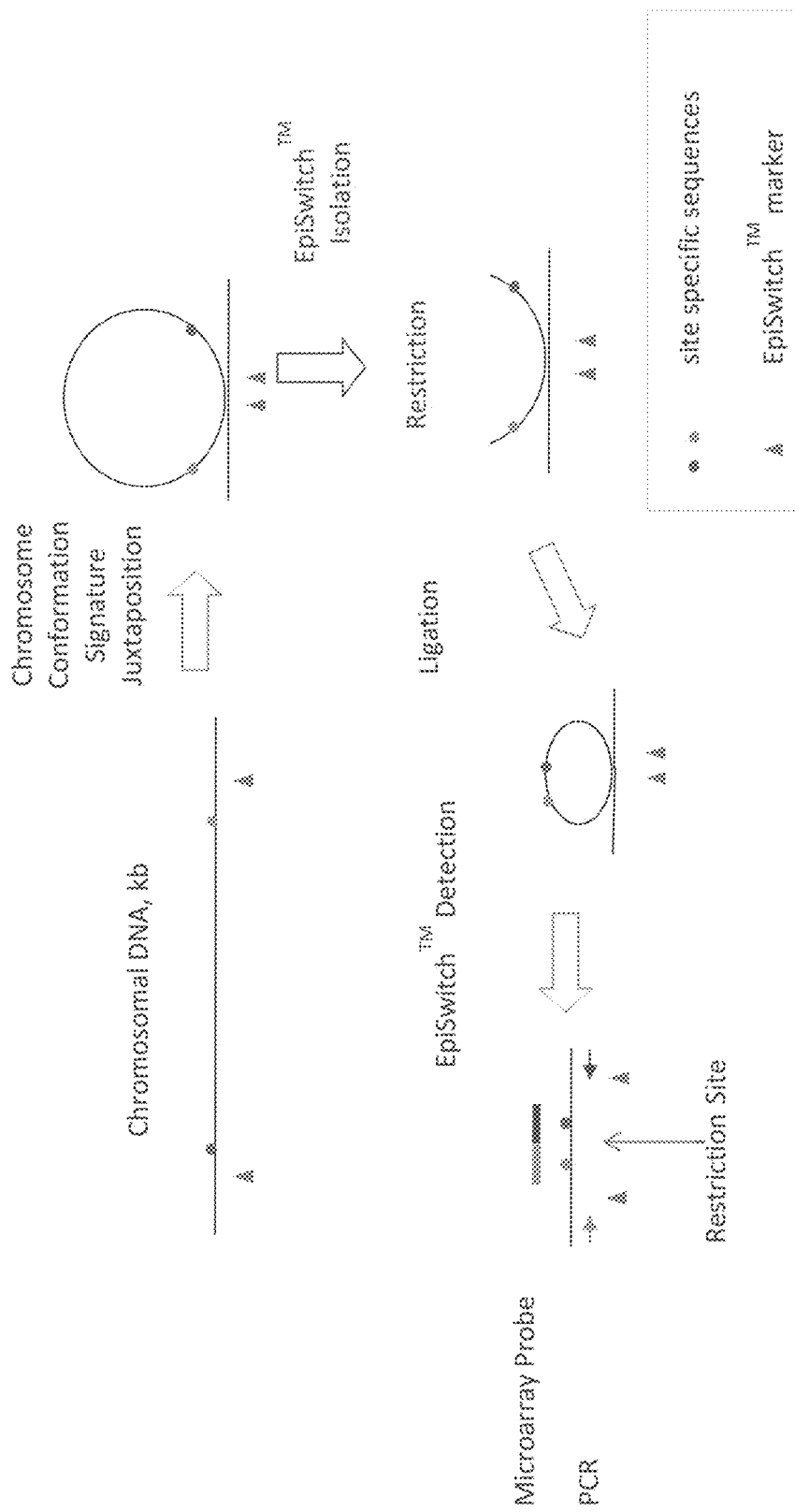
FIG. 4 is a Schematic diagram of the 3C extraction process. 3C means chromatin conformation capture, or chromosome conformation capture.

In order to test the 'accuracy' and 'robustness of performance' of the logistic classifying model that determined the 5 EpiSwitch™ CSS markers, 150 ROC** curves (with unique start points) were generated by random data re-sampling of the R and NR data (FIG. 3A). This resulted in the data being split into training (66%, equivalent to 6000 known class samples) and test (34%, equivalent to 3000 unknown class samples) groups; importantly the same split is never seen in the data for cross validation. The average discriminative ability (AUC) of the model was 89.9% (95% CI 87-100%), with an average sensitivity (adjusted for response prevalence) for NR of 92% and an average specificity for R of 84%. To determine the predictive capability of the model, the average model accuracy statistics were adjusted for population R/NR to MTX using Bayes prevalence theorem[21]. Using a 55% MTX response rate, the positive predictive value (PPV) was 90.3% whilst the negative predictive value (NPV) was 86.5%. If the response rate was adjusted to 60%, this decreased the PPV to 87% whilst increasing the NPV to 89%.

** Note: ROC means Receiver Operating Characteristic and refers to ROC curves. An ROC curve is a graphical plot that illustrates the performance of a binary classifier system as its discrimination threshold is varied. The curve is created by plotting the true positive rate against the false positive rate at various threshold settings.

As an independent evaluation of the discerning powers of the selected 5 EpiSwitch™ CCS markers, factor analysis of mixed data (FAMD) incorporating 30 HC was performed. This illustrated that the signature not only has the power to differentiate between MTX R and NR but also retains sufficient disease-specific features to differentiate between healthy individuals and RA patients (FIG. 3B).

Example 1—Table 8a—Stratifying Between RA-MTX Responders and Non-Responders

Table 8a, and continuation Table 8b, presented hereinafter, show inter alia a list of about 54 DNA probes (60mers) and their DNA sequences. These probes represent some of the probes used in Example 1. Without being bound, most of the probes illustrated in Table 8a+8b are thought likely to be significant to/useful in stratifying between RA-MTX responders and RA-MTX non-responders. The shown probes were investigated further by PCR. P Value=Probability value; adj.=adjusted.

Example 1—Conclusion

In conclusion, our study of the epigenetic: profile classification of DMARD naïve ERA patients on the basis of prospective clinical assessment for R/NR has identified a consistent epigenetic signature, which discriminates an epigenetic state that is conducive and non-conducive to MTX response. This is to our knowledge, the first example of a stable and selectively differentiating blood based epigenetic biomarker in early RA patients that appears disease related (versus healthy controls) and that can predict non-responsiveness to first-line MIX therapy. This model offers direct and practical benefits with a validated classifier based on 5 conditional CCS and their detection by the industrial ISO-13485 EpiSwitch™ platform, which has the potential to be routinely available in the near future within clinical practice. Importantly, by adopting this predictive signature it should be possible to stratify MTX naïve ERA patients into R and NR cohorts. This offers the potential to accelerate patient progression through the currently approved treatment strategy for ERA seeking earlier use of effective therapeutics, hence leading to a 'personalised' treatment regime. Furthermore, it is conceivable that alternative CCS signatures are present in RA patients (and patients with other autoimmune diseases) that could be used to justify fast-tracked biological treatment regimes in the clinic. This would have far reaching socio-economic implications, providing more cost effective and robust therapeutic approaches.

Example 1—Material and Methods

Example 1—RA Patient Population

ERA patients in this study are part of the Scottish early rheumatoid arthritis (SERA) inception cohort. Demographic, clinical and immunological factors were obtained at diagnosis and 6 months (Table 2). Inclusion in the inception cohort was based on clinical diagnosis of undifferentiated polyarthritis or RA (≥1 swollen joint) at a secondary care rheumatology unit in Scotland. Exclusion criteria were previous or current DMARD/biological therapy and/or established alternative diagnosis (i.e. psoriatic arthritis, reactive arthritis). Inclusion in this study was based on a diagnosis of RA (fulfilled the 2010 ACR/EULAR criteria for RA) with moderate to high disease activity (DAS28 ≥3.2) and subsequent monotherapy with MTX. [DAS28=Disease Activity Score of 28 joints. EULAR=The European League Against Rheumatism. ACR=American College of Rheumatology.] Responders were defined as patients who upon receiving MTX achieved DAS28 remission (DAS28 <2.6) or a good response (DAS28 improvement of >1.2 and DAS28 ≤12) at 6 months. Non-responders were defined as patients who upon receiving MTX had no improvement in DAS28 (≤0.6) at 6 months. Blood samples were collected at diagnosis (Baseline) in EDTA tubes and centrifuged to generate a buffy layer containing PBMCs, which was harvested and stored at −80° C. Local ethics committees approved the study protocol and all patients gave informed consent before enrolment into the study.

Example 0.1—EpiSwitch™ Processing, Array and PCR Detection. Probe Design and Locations for EpiSwitch™ Assays Pattern recognition methodology was used to analyse human genome data in relation to the transcriptional units in the human genome. The proprietary EpiSwitch™ pattern recognition software[18,20] provides a probabilistic score that a region is involved in chromatin interaction. Sequences from 123 gene loci were downloaded and processed to generate a list of the 13,322 most probable chromosomal interactions. 60mer probes were designed to interrogate these potential interactions and uploaded as a custom array to the Agilent SureDesign website. Sequence-specific oligonucleotides were designed using Primer3[23], at the chosen sites for screening potential markers by nested PCR. Oligonucleotides were tested for specificity using oligonucleotide specific BLAST.

Example 1—Chromatin Conformation Signature Analysis from Patient PBMC's

Template preparation: Chromatin from 50 µl of each PBMC sample was extracted using the EpiSwitch™ assay following the manufacturer's instructions (Oxford BioDynamics Ltd). Briefly, the higher order structures are fixed with formaldehyde, the chromatin extracted, digested with TaqI, dilution and ligation in conditions to maximize intramolecular ligation, and subsequent proteinase K treatment. EpiSwitch™ microarray: EpiSwitch™ microarray hybridization was performed using the custom Agilent 8×60k array using the Agilent system, following the manufacturer's instructions (Agilent). Each array contains 55088 probes spots, representing 13,322 potential chromosomal interactions predicted by the EpiSwitch™ pattern recognition software quadruplicated, plus EpiSwitch™ and Agilent controls. Briefly, 1 µg of EpiSwitch™ template was labelled using the Agilent SureTag labelling kit. Processing of labelled DNA was performed. Array analysis was performed immediately after washing using the Agilent scanner and software. In order to compare all the experiments the data was background corrected and normalized. Since each spot in the array is present in quadruplicate, the median of the four spots of each probe in the array was calculated and its log 2 transformed value was used for further analysis. The coefficient of variation and p-value was calculated for each probe replicate. EpiSwitch™ PCR detection: Oligonucleotides were tested on template to confirm that each primer set was working correctly. To accommodate for technical and replicate variations, each sample was processed four times. All the extracts from these four replicates were pooled and the final nested PCR was performed on each sample. This procedure permitted the detection of limited copy-number templates with higher accuracy[24]. All PCR amplified samples were visualised by electrophoresis in the LabChip® GX from Perkin Elmer, using the LabChip DNA 1K Version2 kit (Perkin Elmer) and internal DNA marker was loaded on the DNA chip according to the manufacturer's protocol using fluorescent dyes. Fluorescence was detected by laser and electropherogram read-outs translated into a simulated band on gel picture using the instrument software. The threshold we set for a band to be deemed positive was 30 fluorescence units and above.

Example 1—Statistical Methods and Packages

GraphPad Prism and SPSS were used for all statistical analyses of clinical data. The chi-square test and Fisher's exact test (for categorical variables), the t-test for independent samples (for continuous normally distributed variables), and the Mann-Whitney U test (for continuous variables without normal distribution) were used to identify differences. The level of statistical significance was set at 0.05, and all tests were 2-sided. R (and appropriate packages) was used for evaluation of EpiSwitch™ data. This included Stats package for Chi-square test and GLM (logit), ROCR package for ROC curves from WEKA odds probabilities, gplot & stats package in R for Heatmaps. FactorMiner package was used for PCA and Factor plots. Weka was used for Attribute Reduction, data randomisation and re-sampling, Logistic Model Classifier, AUC calculations and model accuracy calculations.

References for Example 1 and for all of the Present Patent Specification

1. Liao, K. P., Alfredsson, L. and Karlson, E. W. Environmental influences on risk for rheumatoid arthritis. *Curr. Opin. Rheumatol.* 21, 279-283 (2009).
2. Bottini, N. & Firestein, G. S. Epigenetics in rheumatoid arthritis: a primer for rheumatologists. *Curr. Rheumatol. Rep.* 15, 372 (2013).
3. McInnes, I. B. & Schett, G. The pathogenesis of rheumatoid arthritis. *N. Engl. J. Med.* 365, 2205-19 (2011).
4. Liu, Y. et al. Epigenome-wide association data implicate DNA methylation as an intermediary of genetic risk in rheumatoid arthritis. *Nat. Biotechnol.* 31, 142-7 (2013).
5. Nakano, K., Whitaker, J. W., Boyle, D. L., Wang, W. & Firestein, G. S. DNA methylome signature in rheumatoid arthritis. *Ann. Rheum. Dis.* 72, 110-17 (2013).
6. De la Rica, L. et al. Identification of novel markers in rheumatoid arthritis through integrated analysis of DNA methylation and microRNA expression. *J. Autoimmun.* 41, 6-16 (2013).
7. Viatte, S., Plant, D. & Raychaudhuri, S. Genetics and epigenetics of rheumatoid arthritis. *Nat. Rev. Rheumatol.* 9, 141-53 (2013).
8. Hider, S. L. et al. Can clinical factors at presentation be used to predict outcome of treatment with methotrexate in patients with early inflammatory polyarthritis? *Ann. Rheum. Dis.* 68, 57-62 (2009).
9. Farragher, T. M., Lunt, M., Fu, B., Bunn, D. & Symmons, D. P. M. Early treatment with, and time receiving, first disease-modifying antirheumatic drug predicts long-term function in patients with inflammatory polyarthritis. *Ann. Rheum. Dis.* 69, 689-95 (2010).
10. Bakker, M. F. et al. Early clinical response to treatment predicts 5-year outcome in RA patients: follow-up results from the CAMERA study. *Ann. Rheum. Dis.* 70, 1099-103 (2011).
11. Barrera, P. et al. Drug survival, efficacy and toxicity of monotherapy with a fully human anti-tumour necrosis factor-alpha antibody compared with methotrexate in long-standing rheumatoid arthritis. *Rheumatology (Oxford).* 41, 430-439 (2002).
12. Ling, J. Q. & Hoffman, A. R. Epigenetics of long-range chromatin interactions. *Pediatr. Res.* 61, 11R-16R (2007).
13. Deng, W. & Blobel, G. A. Do chromatin loops provide epigenetic gene expression states? *Curr. Opin. Genet. Dev.* 20, 548-54 (2010).
14. Kadauke, S. & Blobel, G. A. Chromatin loops in gene regulation. *Biochim Biophys Acta.* 1789, 17-25 (2009).
15. Crutchley, J. L., Wang, X. Q. D., Ferraiuolo, M. a & Dostie, J. Chromatin conformation signatures: ideal human disease biomarkers? *Biomark. Med.* 4, 611-29 (2010).
16. Christova, R. et al. P-STAT1 mediates higher-order chromatin remodelling of the human MHC in response to IFNgamma. *J. Cell Sci.* 120, 3262-3270 (2007).
17. Watanabe, T. et al. Higher-Order Chromatin Regulation and Differential Gene Expression in the Human Tumour Necrosis Factor/Lymphotoxin Locus in Hepatocellular Carcinoma Cells. *Mol. Cell. Biol.* 32, 1529-1541 (2012).
18. Mukhopadhyay, S., Ramadass, A. S., Akoulitchev, A. & Gordon, S. Formation of distinct chromatin conformation signatures epigenetically regulate macrophage activation. *Int. Immunopharmacol.* 18, 7-11 (2013).
19. Harismendy, O. et al. 9p21 DNA variants associated with coronary artery disease impair interferon-γ signalling response. *Nature* 470, 264-268 (2011).
20. Bastonini, E. et al. Chromatin barcodes as biomarkers for melanoma. *Pigment Cell Melanoma Res.* (2014). doi:10.1111/pcmr.12258.
21. Rau, R. & Herborn, G. Benefit and risk of methotrexate treatment in rheumatoid arthritis. *Clin. Exp. Rheumatol.* 22, S83-S94 (2004).
22. Kosaka, N. & Ochiya, T. Unraveling the Mystery of Cancer by Secretory microRNA: Horizontal microRNA Transfer between Living Cells. *Front. Genet.* 2, 97 (2011).
23. Rozen, S. & Skaletsky, H. Primer3 on the WWW for general users and for biologist programmers. *Methods Mol Biol.* 132, 365-386 (2000).
24. Dekker, J., Rippe, K., Dekker, M. & Kleckner, N. Capturing chromosome conformation. *Science* 295, 1306-11 (2002).

TABLE 1

Example 1-Selected genes for EpiSwitch ™ Array

| GENE | Description | Comments | Number of identified EpiSwitch ™ sites |
|---|---|---|---|
| ABCB1 | ATP-binding cassette, sub-family B (MDR/TAP), member 1 | MTX related genes | 56 |
| ABCG2 | ATP-binding cassette, sub-family G (WHITE), member 2 | MTX related genes | 84 |
| ADORA2A | Adenosine A2a receptor | MTX related genes | 72 |
| AFF3 | AF4/FMR2 family, member 3 | RA SNP association | 140 |

TABLE 1-continued

Example 1-Selected genes for EpiSwitch ™ Array

| GENE | Description | Comments | Number of identified EpiSwitch ™ sites |
|---|---|---|---|
| AMPD1 | Adenosine monophosphate deaminase 1 | MTX related genes | 24 |
| ApoE | Apolipoprotein E | Apolipoproteins | 96 |
| ATIC | 5-aminoimidazole-4-carboxamide ribonucleotide formyltransferase/IMP cyclohydrolase | MTX related genes | 32 |
| BLK | B lymphoid tyrosine kinase | RA SNP association | 196 |
| BTNL2 | Butyrophilin-like 2 (MHC class II associated) | Associated with RA via exome sequencing | 44 |
| C5orf30 | Chromosome 5 open reading frame 30 | RA SNP association | 96 |
| CCL2 | Chemokine (C-C motif) ligand 2 | Cytokines & Chemokines | 404 |
| CCL21 | Chemokine (C-C motif) ligand 21 | Cytokines & Chemokines | 28 |
| CCL3 | Chemokine (C-C motif) ligand 3 | Cytokines & Chemokines | 52 |
| CCL5 | Chemokine (C-C motif) ligand 5 | Cytokines & Chemokines | 52 |
| CCR1 | Chemokine (C-C motif) receptor 1 | Cytokines & Chemokines receptors | 172 |
| CCR2 | Chemokine (C-C motif) receptor 2 | Cytokines & Chemokines receptors | 164 |
| CCR6 | Chemokine (C-C motif) receptor 6 | Cytokines & Chemokines receptors | 56 |
| CD28 | Cluster of Differentiation 28 | RA SNP association | 132 |
| CD40 | Cluster of Differentiation 40 | RA SNP association | 148 |
| CD80 | Cluster of Differentiation 80 | Cell surface | 76 |
| CHI3L1 | Chitinase 3-like 1 (cartilage glycoprotein-39) | Extracellular | 64 |
| CHUK | Conserved helix-loop-helix ubiquitous kinase | NFKB | 92 |
| CIITA | Class II, major histocompatibility complex, transactivator | NLR pathway | 80 |
| CLEC12A | C-type lectin domain family 12, member A | Other | 52 |
| CLEC16A | C-type lectin domain family 16, member A | Other | 108 |
| COL2A1 | Collagen, type II, alpha 1 | Collagens | 100 |
| CTLA4 | Cytotoxic T-lymphocyte-associated protein 4 | RA SNP association | 68 |
| CX3CL1 | Chemokine (C-X3-C motif) ligand 1 | Cytokines & Chemokines | 92 |
| CXCL12 | Chemokine (C-X-C motif) ligand 12 | Cytokines & Chemokines | 80 |
| CXCL13 | Chemokine (C-X-C motif) ligand 13 | Cytokines & Chemokines | 80 |
| CXCL8 | Chemokine (C-X-C motif) ligand 8 | Cytokines & Chemokines | 48 |
| CXCR3 | Chemokine (C-X-C motif) receptor 3 | Cytokines & Chemokines receptors | 72 |
| CXCR4 | Chemokine (C-X-C motif) receptor 4 | Cytokines & Chemokines receptors | 56 |
| DHFR | Dihydrofolate reductase | MTX related genes | 72 |
| ESR1 | Oestrogen receptor 1 | FLS MTX responsive genes | 140 |
| FCGR2A | Fc fragment of IgG, low affinity IIa, receptor (CD32) | RA SNP association | 100 |
| FCGR3B | Fc fragment of IgG, low affinity IIIb, receptor (CD16b) | RA SNP association | 192 |
| FCRL3 | Fc receptor-like 3 | Other | 68 |
| FPGS | Folylpolyglutamate synthase | MTX related genes | 56 |
| HTR2A | 5-hydroxytryptamine (serotonin) receptor 2A, G protein-coupled | Other | 80 |
| ICAM1 | Intercellular adhesion molecule 1 | FLS MTX responsive genes | 132 |
| ICOS | Inducible T-cell co-stimulator | RA SNP association | 200 |
| IFNAR1 | Interferon (alpha, beta and omega) receptor 1 | Cytokines & Chemokines receptors | 80 |
| IFNg | Interferon, gamma | Cytokines & Chemokines | 52 |
| IKBKB | Inhibitor of kappa light polypeptide gene enhancer in B-cells, kinase beta | NFKB | 128 |
| IL-10 | Interleukin 10 | Cytokines & Chemokines | 48 |
| IL-15 | Interleukin 15 | Cytokines & Chemokines | 76 |
| IL-17A | Interleukin 17A | Cytokines & Chemokines | 32 |
| IL-18 | Interleukin 18 | Cytokines & Chemokines | 64 |
| IL-1a | Interleukin 1 alpha | Cytokines & Chemokines | 196 |
| IL-2 | Interleukin 2 | Cytokines & Chemokines | 44 |
| IL-21R | Interleukin 21 receptor | Cytokines & Chemokines receptors | 60 |
| IL-23 | Interleukin 23 | Cytokines & Chemokines | 56 |
| IL-23R | Interleukin 23 receptor | Cytokines & Chemokines receptors | 104 |
| IL-2RA | Interleukin 2 receptor, alpha | Cytokines & Chemokines receptors | 100 |
| IL-2RB | Interleukin 2 receptor, beta | Cytokines & Chemokines receptors | 72 |
| IL-32 | Interleukin 32 | Cytokines & Chemokines | 44 |
| IL-4 | Interleukin 4 | Cytokines & Chemokines | 32 |
| IL-4R | Interleukin 4 receptor | Cytokines & Chemokines receptors | 76 |
| IL-6 | Interleukin 6 | Cytokines & Chemokines | 48 |
| IL-6ST | Interleukin 6 signal transducer (gp130, oncostatin M receptor) | Cytokines & Chemokines receptors | 72 |
| IL-7 | Interleukin 7 | Cytokines & Chemokines | 72 |
| IL1RN | Interleukin 1 receptor antagonist | MTX related genes | 28 |
| IRAK3 | Interleukin-1 receptor-associated kinase 3 | Signalling | 80 |

TABLE 1-continued

Example 1-Selected genes for EpiSwitch ™ Array

| GENE | Description | Comments | Number of identified EpiSwitch ™ sites |
|---|---|---|---|
| IRF5 | Interferon regulatory factor 5 | Signalling | 76 |
| ITGA4 | Integrin, alpha 4 (antigen CD49D, alpha 4 subunit of VLA-4 receptor) | Cell surface | 100 |
| ITPA | Inosine triphosphatase (nucleoside triphosphate pyrophosphatase) | MTX related genes | 56 |
| JAG1 | Jagged 1 | FLS MTX responsive genes | 84 |
| M-CSF | Colony stimulating factor 1 | Cytokines & Chemokines | 96 |
| MafB | V-maf musculoaponeurotic fibrosarcoma oncogene homolog B | Transcription factors | 52 |
| MAL | Mal, T-cell differentiation protein | TLR pathway | 68 |
| MEFV | Mediterranean fever | Other | 76 |
| MMP14 | Matrix metallopeptidase 14 | Matrix Metalloproteinases | 92 |
| MMP2 | Matrix metallopeptidase 2 | Matrix Metalloproteinases | 212 |
| MMP9 | Matrix metallopeptidase 9 | Matrix Metalloproteinases | 68 |
| MTHFD1 | Methylenetetrahydrofolate dehydrogenase (NADP + dependent) 1, methenyltetrahydrofolate cyclohydrolase, formyltetrahydrofolate synthetase | MTX related genes | 80 |
| MTHFR | Methylenetetrahydrofolate reductase (NAD(P)H) | MTX related genes | 52 |
| MyD88 | Myeloid differentiation primary response gene 88 | TLR pathway | 80 |
| NFAT | Nuclear factor of activated T cells | Transcription factors | 204 |
| NFATC2IP | Nuclear factor of activated T-cells, cytoplasmic, calcineurin-dependent 2 interacting protein | RA SNP association | 84 |
| NFKB1 | Nuclear factor of kappa light polypeptide gene enhancer in B-cells 1 | NFKB | 96 |
| NFKB2 | Nuclear factor of kappa light polypeptide gene enhancer in B-cells 2 (p49/p100) | NFKB | 64 |
| NFKBIB | Nuclear factor of kappa light polypeptide gene enhancer in B-cells inhibitor, beta | NFKB | 120 |
| NFKBIA | Nuclear factor of kappa light polypeptide gene enhancer in B-cells inhibitor, alpha | NFKB | 88 |
| NLRP1 | NLR family, pyrin domain containing 1 | NLR pathway | 108 |
| NLRP3 | NLR family, pyrin domain containing 3 | NLR pathway | 128 |
| PADI4 | Peptidyl arginine deiminase, type IV | RA SNP association | 168 |
| PRDM1 | PR domain containing 1, with ZNF domain | RA SNP association | 120 |
| PRKCQ | Protein kinase C, theta | RA SNP association | 216 |
| PRKCZ | Protein kinase C, zeta | Other | 184 |
| PSTPIP1 | Proline-serine-threonine phosphatase interacting protein 1 | Cytoskeletal | 96 |
| PTGS2 | Prostaglandin-endoperoxide synthase 2 (prostaglandin G/H synthase and cyclooxygenase) | Signalling | 52 |
| PTPN22 | Protein tyrosine phosphatase, non-receptor type 22 | RA SNP association | 196 |
| PXK | PX domain containing serine/threonine kinase | RA SNP association | 296 |
| RBPJ | Recombination signal binding protein for immunoglobulin kappa J region | RA SNP association | 296 |
| REL | V-rel reticuloendotheliosis viral oncogene homolog A | NFKB | 92 |
| RFC-1 | Replication factor C (activator) 1, 145 kDa | MTX related genes | 52 |
| RGMB | RGM domain family, member B | FLS MTX responsive genes | 80 |
| RUNX1 | Runt-related transcription factor 1 | RA SNP association | 212 |
| SH2B3 | SH2B adaptor protein 3 | RA SNP association | 124 |
| SHMT | Serine hydroxymethyltransferase 1 (soluble) | MTX related genes | 68 |
| SLC19A1 | Solute carrier family 19 (folate transporter), member 1 | MTX related genes | 76 |
| SPRED2 | Sprouty-related, EVH1 domain containing 2 | RA SNP association | 336 |
| STAT4 | Signal transducer and activator of transcription 4 | Signalling | 128 |
| SUMO1 | SMT3 suppressor of mif two 3 homolog 1 | SUMO | 132 |
| TAGAP | T-cell activation RhoGTPase activating protein | RA SNP association | 92 |
| TLR1 | Toll-like receptor 1 | TLR pathway | 204 |
| TLR2 | Toll-like receptor 2 | TLR pathway | 52 |
| TLR4 | Toll-like receptor 4 | TLR pathway | 52 |
| TNF | Tumour necrosis factor | Cytokines & Chemokines | 68 |
| TNFAIP3 | Tumour necrosis factor, alpha-induced protein 3 | RA SNP association | 180 |
| TNERSF11B | Tumour necrosis factor receptor superfamily, member 11b | Cytokines & Chemokines receptors | 80 |
| TNIFRSF13C | Tumour necrosis factor receptor superfamily, member 13C | Cytokines & Chemokines receptors | 52 |
| TNFRSF14 | Tumour necrosis factor receptor superfamily, member 14 | RA SNP association | 112 |
| TNERSF17 | Tumour necrosis factor receptor superfamily, member 17 | Cytokines & Chemokines receptors | 44 |
| TNFRSF1A | Tumour necrosis factor receptor superfamily, member 1A | Cytokines & Chemokines receptors | 72 |
| TNFRSF1B | Tumour necrosis factor receptor superfamily, member 1B | Cytokines & Chemokines receptors | 72 |
| TNFSF11 | Tumour necrosis factor (ligand) superfamily, member 11 | Cytokines & Chemokines | 52 |
| TNFSF13 | Tumour necrosis factor (ligand) superfamily, member 13 | Cytokines & Chemokines | 48 |
| TRAF1 | TNF receptor-associated factor 1 | RA SNP association | 120 |
| TRAF6 | TNF receptor-associated factor 6 | RA SNP association | 72 |
| TYMS | Thymidylate synthetase | MTX related genes | 48 |
| WISP3 | WNT1 inducible Signalling pathway protein 3 | Signalling | 88 |

TABLE 2

Example 1 - Patient Characteristics - Discovery Cohort

| | Baseline | | | 6 months | | | |
|---|---|---|---|---|---|---|---|
| | Non-responder | Responder | P value | Non-responder | Responder | P value | Healthy control |
| Age - years | 55 ± 6.1 | 55 ± 19.7 | >0.99 | — | — | — | 52 ± 13.3 |
| Males - no. (%) | 1 (25) | 1 (25) | 1 | — | — | — | 3 (38) |
| Caucasian - no. (%) | 4 (100) | 4 (100) | — | — | — | — | 8 (100) |
| Body mass index - kg/m² | 29.5 ± 0.96$ | 25.0 ± 4.88 | 0.19 | — | — | — | — |
| Patient global assessment (VAS, 0-100 mm) | 54.3 ± 33.5 | 39.3 ± 30.2 | 0.53 | 54.5 ± 20.0 | 9.3 ± 6.2 | 0.029 | — |
| Physician global assessment (VAS, 0-100 mm) | 55 ± 29.7 | 38.5 ± 17.8 | 0.38 | 32.5 ± 20.2 | 8.8 ± 7.0 | 0.068 | — |
| Number of swollen joints (0-28) | 11.3 ± 5.3 | 4.8 ± 3.9 | 0.09 | 15 ± 10.7 | 2.0 ± 2.8 | 0.057 | — |
| Number of tender joints (0-28) | 10.5 ± 7.7 | 4.8 ± 6.4 | 0.2 | 11.25 ± 10.6 | 0.5 ± 1.0 | 0.029 | — |
| CDAI | 32.7 ± 5.2 | 17.3 ± 9.6 | 0.03 | 35.0 ± 21.2 | 4.3 ± 3.7 | 0.03 | — |
| DAS28-CRP | 5.1 ± 0.2 | 4.2 ± 0.77 | 0.06 | — | — | — | — |
| DAS28-ESR | 5.5 ± 0.5$ | 4.6 ± 0.9$ | 0.4 | 5.3 ± 1.3 | 2.8 ± 0.7 | 0.016 | — |
| RF (IU/ml) | 35.4 ± 25.6 | 321 ± 140$ | 0.06 | — | — | — | — |
| CCP (U/ml) | 10.3 ± 7.2 | 340 ± 0$ | 0.06 | — | — | — | — |
| Current smoker - no. (%) | 2 (50) | 1 (25) | — | — | — | — | — |
| Previous smoker - no. (%) | 1 (25) | 1 (25) | — | — | — | — | — |
| Non-smoker - no. (%) | 1 (25) | 2 (50) | — | — | — | — | — |

The Fisher exact unconditional test is used to assess differences in proportions between the two groups. To examine differences in continuous variables between the two groups, the independent samples t-test or the Mann-Whitney U-test (depending on distribution of data) is used.
$n = 3

TABLE 3

Example 1 - 65 Selected genes from EpiSwitch™ Array analysis

| Gene | Probes* | adjusted p value | EpiSwitch™ ratio | HC_NR_MTX | HC_R_MTX | NR_R_MTX | Association |
|---|---|---|---|---|---|---|---|
| 19_55449062_55451429_55484960_55486708_RF | 19_55449062_55451429_55484960_55486708_RF | 0.079228864 | −1.43395525 | 0 | −1 | −1 | R |
| C5orf30 | C5orf30_Site5_Site2_FF | 0.079228864 | −1.24257534 | −1 | −1 | −1 | R |
| CHUK | CHUK_Site7_Site2_RF | 0.079228864 | −1.32868581 | 1 | −1 | −1 | R |
| CXCL13 | CXCL13_Site1_Site3_RR | 0.079228864 | −1.29833859 | 0 | −1 | −1 | R |
| TLR1 | TLR1_Site4_Site7_FR | 0.079228864 | −1.43064593 | 1 | −1 | −1 | R |
| 11_47175706_47180170_47251505_47252468_FR | 11_47175706_47180170_472451505_47252468_FR | 0.083312472 | −1.20859706 | 1 | −1 | −1 | R |
| C5orf30 | C5orf30_Site4_Site2_FF | 0.084204721 | −1.20024867 | 1 | −1 | −1 | R |
| TLR1 | TLR1_Site9_Site2_FF | 0.086622849 | −1.37554182 | 1 | −1 | −1 | R |
| FCRL3 | FCRL3_Site9_Site7_FF | 0.090200643 | −1.25121814 | 1 | −1 | −1 | R |
| SH2B3 | SH2B3_Site6_Site5_FF | 0.090200643 | −1.32.868581 | 1 | −1 | −1 | R |
| 12_69705360_69711928_69799162_69800678_RF | 12_69705360_69711928_69799162_69800678_RF | 0.097224197 | −1.20580783 | 1 | −1 | −1 | R |
| IL-23R | IL-23R_Site5_Site8_FF | 0.108787769 | −1.26868449 | 1 | −1 | −1 | R |
| CLEC12A | CLEC12A_Site6_Site1_FR | 0.112869007 | −1.22264028 | 0 | −1 | −1 | R |
| CXCL8 | CXCL8_Site7_Site6_FR | 0.118123176 | −1.13288389 | 0 | −1 | −1 | R |
| MyD88 | MyD88_Site5_Site1_FR | 0.129904996 | −1.18372449 | 1 | 0 | −1 | R |
| PRDM1 | PRDM1_Site6_Site2_RR | 0.144057138 | −1.19195794 | 1 | −1 | −1 | R |

TABLE 3-continued

Example 1 - 65 Selected genes from EpiSwitch™ Array analysis

| Gene | Probes* | adjusted p value | EpiSwitch ™ ratio | HC_NR_MTX | HC_R_MTX | NR_R_MTX | Association |
|---|---|---|---|---|---|---|---|
| MMP2 | MMP2_Site8_Site9_FF | 0.146105678 | −1.20859706 | 1 | −1 | −1 | R |
| SPRED2 | SPRED2_Site4_Site8_RF | 0.149371667 | −1.38510947 | 1 | −1 | −1 | R |
| C5orf30 | C5orf30_Site4_Site8_RF | 0.150085134 | −1.17826714 | 1 | −1 | −1 | R |
| 19_10294661_10295285_10370560_10371551_RR | 19_10294661_10295285_10370560_10371551_RR | 0.153140631 | −1.20859706 | 1 | −1 | −1 | R |
| TNFRSF13C | TNFRSF13C_Site3_Site6_FF | 0.15333898 | −1.20580783 | 1 | −1 | −1 | R |
| IL-23 | IL-23_Site4_Site5_F | 0.160960834 | −1.18099266 | 0 | −1 | −1 | R |
| NFKBIB | NFKBIB_Site8_Site9_FR | 0.168381727 | −1.23114441 | 1 | −1 | −1 | R |
| TNFRSF13C | TNFRSF13C_Site1_Site6_FF | 0.16921449 | −1.1198716 | 1 | −1 | −1 | R |
| CD28 | CD28_Site5_Site9_RR | 0.171723501 | −1.14340249 | 1 | −1 | −1 | R |
| NFKB1 | NFKB1_Site4_Site8_RR | 0.185725586 | −1.20024867 | 1 | −1 | −1 | R |
| CHUK | CHUK_Site3_Site5_RF | 0.188137111 | −1.13026939 | 1 | −1 | −1 | R |
| TLR1 | TLR1_Site9_Site3_FR | 0.188137111 | −1.19747871 | 1 | −1 | −1 | R |
| M-CSF | M-CSF_Site5_Site6_FF | 0.191292635 | −1.20859706 | 1 | −1 | −1 | R |
| NFKBIB | NFKBIB_Site1_Site8_FF | 0.191922112 | −1.12766093 | 1 | −1 | −1 | R |
| 11_47175706_47180170_47202910_47204016_FF | 11_47175706_47180170_47202910_47204016_FF | 0.192002056 | −1.20580783 | 1 | −1 | −1 | R |
| PRDM1 | PRDM1_Site6_Site1_RR | 0.194604588 | −1.18920712 | 1 | −1 | −1 | R |
| TNFRSF14 | TNFRSF14_Site4_Site1_RR | 0.082014717 | 1.526259209 | 0 | 1 | 1 | NR |
| SH2B3 | SH2B3_Site3_Site2_FF | 0.083312472 | 1.228303149 | −1 | 1 | 1 | NR |
| MyD88 | MyD88_Site2_Site4_FR | 0.086246871 | 1.211392737 | 0 | 1 | 1 | NR |
| MafB | MafB_Site2_Site4_FF | 0.090511832 | 1.170128253 | −1 | 1 | 1 | NR |
| PRKCZ | PRKCZ_Site6_Site3_RF | 0.093763087 | 1.316462719 | 0 | 1 | 1 | NR |
| NFAT | NFAT_Site2_Site10_FR | 0.093849223 | 1.208597056 | −1 | 1 | 1 | NR |
| NFAT | NFAT_Site5_Site10_RR | 0.094393734 | 1.25411241 | −1 | 1 | 1 | NR |
| MAL | MAL_Site2_Site6_RF | 0.095094028 | 1.274560627 | 0 | 1 | 1 | NR |
| FCGR2A | FCGR2A_Site3_Site6_RR | 0.096581892 | 1.170128253 | −1 | 1 | 1 | NR |
| IL-32 | IL-32_Site5_Site4_FR | 0.097224197 | 1.205807828 | 0 | 1 | 1 | NR |
| MTHFD1 | MTHFD1_Site1_Site7_RF | 0.114751424 | 1.175547906 | −1 | 1 | 1 | NR |
| TLR2 | TLR2_Site1_Site5_RR | 0.120590183 | 1.217003514 | −1 | 1 | 1 | NR |
| NFAT | NFAT_Site6_Site_10_RR | 0.129631525 | 1.211392737 | −1 | 1 | 1 | NR |
| ICAM1 | ICAM1_Site4_Site9_FR | 0.131386096 | 1.180992661 | −1 | 1 | 1 | NR |
| NFAT | NFAT_Site5_Site10_FR | 0.133034069 | 1.170128253 | −1 | 1 | 1 | NR |
| MTHFD1 | MTHFD1_Site5_Site7_RF | 0.144559523 | 1.156688184 | −1 | 1 | 1 | NR |
| MTHFR | MTHFR_Site6_Site4_RR | 0.150085134 | 1.170128253 | −1 | 1 | 1 | NR |
| ICAM1 | ICAM1_Site4_Site1_FF | 0.151103565 | 1.140763716 | −1 | 1 | 1 | NR |
| MTHFD1 | MTHFD1_Site1_Site7_RF | 0.114751424 | 1.175547906 | −1 | 1 | 1 | NR |

TABLE 3-continued

Example 1 - 65 Selected genes from EpiSwitch ™ Array analysis

| Gene | Probes* | adjusted p value | EpiSwitch ™ ratio | HC_NR_MTX | HC_R_MTX | NR_R_MTX | Association |
|---|---|---|---|---|---|---|---|
| NFAT | NFAT_Site11_Site10_RR | 0.158903523 | 1.197478705 | −1 | 1 | 1 | NR |
| NFAT | NFAT_Site10_Site9_RF | 0.160614052 | 1.197478705 | −1 | 1 | 1 | NR |
| MafB | MafB_Site5_Site2_RF | 0.167291268 | 1.164733586 | −1 | 1 | 1 | NR |
| NFAT | NFAT_Site7_Site10_RR | 0.169766598 | 1.189207115 | −1 | 1 | 1 | NR |
| FCGR2A | FCGR2A_Site3_Site7_RR | 0.180386617 | 1.125058485 | −1 | 1 | 1 | NR |
| MafB | MafB_Site6_Site2_RF | 0.186948332 | 1.107008782 | −1 | 1 | 1 | NR |
| ADORA2A | ADORA2A_Site1_Site7_FR | 0.191209559 | 1.138131035 | −1 | 1 | 1 | NR |
| MMP9 | MMP9_Site2_Site3_FR | 0.192328613 | 1.132883885 | −1 | 1 | 1 | NR |
| COL2A1 | COL2A1_Site7_Site2_FF | 0.193661549 | 1.112136086 | −1 | 1 | 1 | NR |
| TNFRSF1B | TNFRSF1B_Site1_Site7_FR | 0.19556991 | 1.154018752 | −1 | 1 | 1 | NR |
| FCGR2A | FCGR2A_Site3_Site2_RR | 0.197822331 | 1.117287138 | −1 | 1 | 1 | NR |

*Probes were designed based on 3 dimensional orientation of the chromosomal confirmation sites. Hence, these were either FF (Forward-Forward), FR (Forward-Reverse), RF (Reverse-Forward) or RR (Reverse-Reverse).

Key
HC_NR_MTX  1 = loop in HC
           0 = Not_Relevant
           "−1" = loop in NR
HC_R_MTX   1 = loop in HC
           0 = Not_Relevant
           "−1" = loop in R
NR_R_MTX   1 = loop in NR
           0 = Not_Relevant
           "−1" = loop in R

TABLE 4

Example 1 - Patient characteristics - Validation Cohort

| | Baseline | | | 6 months | | | |
|---|---|---|---|---|---|---|---|
| | Non-Responder | responder | P value | Non-Responder | responder | P value | Healthy control |
| Age - years | 58 ± 14.5 | 54 ± 13.2 | 0.26 | — | — | — | 45115.4 |
| Males - no. (%) | 10 (33) | 13 (43) | 0.6 | — | — | — | 11 (37) |
| Caucasian - no. (%) | 30 (100) | 28 (97)$ | — | — | — | — | — |
| Body mass index - kg/m² | 28.3 ± 5.4 | 27.4 ± 4.6$$ | 0.48 | — | — | — | — |
| Patient global assessment (VAS, 0-100 mm) | 48 ± 30.2 | 62 ± 23.0 | 0.05 | 64 ± 23.2 | 11 ± 12.9 | <0.0001 | — |
| €Physician global assessment (VAS, 0-100 mm) | 46 ± 22.7 | 54 ± 21.0 | 0.19 | 39 ± 6.4 | 6.4 ± 6.1 | <0.0001 | — |
| Number of swollen joints (0-28) | 5.8 ± 3.7 | 8.3 ± 4.3 | 0.006 | 6.0 ± 5.2 | 0.2 ± 0.48 | <0.0001 | — |
| Number of tender joints (0-28) | 8.4 ± 6.2 | 7.9 ± 5.2 | 0.97 | 11.6 ± 7.7 | 0.4 ± 0.72 | <0.0001 | — |
| €CDAI | 23.6 ± 10.9 | 27.8 ± 9.8 | 0.13 | 27.9 ± 12.6 | 2.3 ± 2.2 | <0.0001 | — |
| #DAS28-CRP | 4.8 ± 1.0 | 5.1 ± 0.9 | 0.27 | 5.0 ± 0.8 | 1.8 ± 0.44 | <0.0001 | — |
| §DAS28-ESR | 5.2 ± 0.8 | 5.2 ± 1.0 | 0.98 | 5.3 ± 0.8 | 1.8 ± 0.45 | <0.0001 | — |
| €RF (IU/ml) | 196 ± 244 | 138 ± 155 | 0.48 | — | — | — | — |
| ∞CCP (U/ml) | 244 ± 201 | 314 ± 798 | 0.25 | — | — | — | — |
| #C-reactive protein (mg/liter) | 25.8 ± 33.7 | 23.4 ± 30.0 | 0.40 | 12.7 ± 12.2 | 5.5 ± 5.6 | 0.005 | — |
| §Erythrocyte sedimentation rate (mm/hour) | 35 ± 19.8 | 22.6 ± 16.2 | 0.02 | 23 ± 18.6 | 8.5 ± 5.6 | 0.0004 | — |
| ¶Whole Blood cell count | 8.4 ± 2.2 | 7.5 ± 1.7 | 0.09 | 7.6 ± 2.4 | 6.5 ± 1.7 | 0.07 | — |
| ¶Lymphocytes | 1.9 ± 0.59 | 1.7 ± 0.78 | 0.09 | 1.8 ± 0.76 | 1.7 ± 0.95 | 0.31 | — |
| ¶Monocytes | 0.63 ± 0.16 | 0.59 ± 0.22 | 0.50 | 0.59 ± 0.45 | 0.52 ± 0.13 | 0.38 | — |
| ¶Eosinophil | 0.18 ± 0.14 | 0.19 ± 0.13 | 0.55 | 0.19 ± 0.15 | 0.17 ± 0.12 | 0.89 | — |

TABLE 4-continued

Example 1 - Patient characteristics - Validation Cohort

|  | Baseline | | | 6 months | | | |
| --- | --- | --- | --- | --- | --- | --- | --- |
|  | Non-Responder | responder | P value | Non-Responder | responder | P value | Healthy control |
| ¶Platelets | 332 ± 107 | 307 ± 86 | 0.34 | 299 ± 103 | 270 ± 79 | 0.25 | — |
| Current smoker - no. (%) | 10 (33) | 4 (14) | — | — | — | — | — |
| Previous smoker - no. (%) | 10 (33) | 9 (31) | — | — | — | — | — |
| Non-smoker - no. (%) | 10 (33) | 16 (55) | — | — | — | — | — |

The Fisher exact unconditional test is used to assess differences in proportions between the two groups. To examine differences in continuous variables between the two groups, we used the independent samples t-test or the Mann-Whitney U-test (depending on distribution of data).
$One patient "other" (non-white, non-South East Asian, non-Indian Sub-Continent, Non-Afro-Caribbean), one patient did not give an answer.
$$n = 25 in responders for BMI,
€Baseline - n = 29 non-R, n = 30 R; 6m - n = 30 non-R, n = 29,
Baseline - n = 26 non-R, n = 29 R; 6m - n = 21 non-R, n = 29,
§Baseline - n = 19 non-R, n = 23 R; 6m - n = 19 non-R, n = 22,
ᶜBaseline n = 13 non-R, n = 23 R,
∞Baseline - n = 26 non-R, n = 29 R,
¶Baseline - n = 29 non-R, n = 27 R; 6m - n = 28 non-R, n = 25

TABLE 6

Example 1-Observed and predicted number of R and NR to MTX monotherapy at 6 months using the EpiSwitch ™ CCS model.

|  | Predicted response | | |
| --- | --- | --- | --- |
| Observed response | Non-responder | Undefined | Responder |
| Non-responder | 25 | 3 | 2 |
| Responder | 2 | 4 | 24 |

Cut off levels were chosen based on the probability of response to MTX of (approximately) >0.70 for NR and <0.3 for R. NR and R were defined as described in the methods.

Example 1A—RA Analysis: MTX Responders Vs. Non-Responders, and RA Vs. Healthy Controls: Work Subsequent to Example 1

Following on after Example 1, in Example 1A, a biostatistical hypergeometric analysis was carried out, using the "Statistical Pipeline" method(s) at the beginning of the Examples section in the present specification, to generate further refined DNA probes stratifying between MTX responders vs. MTX non-responders, for RA patients on MTX monotherapy.

Example 1A Results: Table 7 (part a and continuation part b) hereinafter discloses Probe and Loci data for RA-MTX—DNA probes stratifying between responders (R) and non-responders (NR). B=B-statistic (lods or B), which is the log-odds that that gene is differentially expressed. FC is the non-log Fold Change. FC_1 is the non-log Fold Change centred around zero. It is seen that Table 7a includes the sequences of 25 refined preferable DNA probes (60mers) for identifying MTX responders (MTX-R), and of 24 (or 25) refined preferable DNA probes (60mers) for identifying MTX non-responders (MTX-NR), from the hypergeometric analysis. Table 9 (parts a, b and c) hereinafter discloses enriched data from a hypergeometric analysis of RA patients vs. healthy controls (HC), and does not relate to the MTX response in RA patients.

TABLE 7a

Example 1A. Probe and Loci data for RA-MTX -probes stratifying between responders and non-responders.

| FC | FC_1 | LS | Loop detected | 60 mer |
| --- | --- | --- | --- | --- |
| 0.5774097 | -1.7318725 | -1 | MTX-R | TGTTTTTTGGCTGCATAAATGTCTTCTTTCGAAATAATCATCAAAATATTTTTCATTGAC (SEQ ID NO: 1) |
| 0.6052669 | -1.6521636 | -1 | MTX-R | CACCCCCATCTCCCTTTGCTGACTCTCTTCGATGAATCCATTTTTTTGGAAATAGATGAT (SEQ ID NO: 2) |
| 0.6567507 | -1.5226477 | -1 | MTX-R | CACCCCCATCTCCCTTTGCTGACTCTCTTCGAACTGTGGCAATTTTAACTTTTCAAATTG (SEQ ID NO: 3) |
| 0.6624775 | -1.5094851 | -1 | MTX-R | CACCCCCATCTCCCTTTGCTGACTCTCTTCGAGGCATGATTTGAGTCTTGACAGAAGTTC (SEQ ID NO: 4) |
| 0.6628804 | -1.5085678 | -1 | MTX-R | TGCCAGTATTTTATTGAGGATTTTTGCATCGAGATTGGGTTGCATCATGTTGGCCAGGCT (SEQ ID NO: 5) |
| 0.6850588 | -1.4597286 | -1 | MTX-R | TGTTTTTTGGCTGCATAAATGTCTTCTTTCGAACTCATGGGCACAAGCAATCCTCCCACC (SEQ ID NO: 6) |
| 0.6868153 | -1.4559955 | -1 | MTX-R | TGCCAGTATTTTATTGAGGATTTTTGCATCGAACAGATGGAGGGAAGAGGGGATAGCTCC (SEQ ID NO: 7) |
| 0.6890053 | -1.4513676 | -1 | MTX-R | TGCCCTAGAGATCTGTGGAACTTTGAACTCGAGTCAAAGAGATATCAAGAGCTTCTATCA (SEQ ID NO: 8) |

TABLE 7a-continued

Example 1A. Probe and Loci data for RA-MTX –probes stratifying between responders and non-responders.

| FC | FC_1 | LS | Loop detected | 60 mer |
|---|---|---|---|---|
| 0.6943398 | -1.4402171 | -1 | MTX-R | CACCCCCATCTCCCTTTGCTGACTCTCTTCGAGGGCAGAATGAGCCTCAGACATCTCCAG (SEQ ID NO: 9) |
| 0.6963019 | -1.4361587 | -1 | MTX-R | TCTCCTGCCTGATTGCCCTGCCAGAACTICGATTTGGGCTATAGTGTTGTTCCAGTCTAA (SEQ ID NO: 10) |
| 0.7008036 | -1.4269334 | -1 | MTX-R | CACCCCCATCTCCCTTTGCTGACTCTCTTCGATCTTGAAGAGATCTCTTCTTAGCAAAGC (SEQ ID NO: 11) |
| 0.7132593 | -1.4020146 | -1 | MTX-R | CACCCCCATCTCCCTTTGCTGACTCTCTTCGAAATATTTTTGCTTGAGCTCCTGTCTCAT (SEQ ID NO: 12) |
| 0.7141705 | -1.4002258 | -1 | MTX-R | TAGGCGCACATGCACACAGCTCGCCTCTTCGACCCAGGAAGATCCAAAGGAGGAACTGAG (SEQ ID NO: 13) |
| 0.7156204 | -1.397389 | -1 | MTX-R | CCCCCACCCCCATCCCAGGAAATTGGTTTCGATGAGAGAAGGCAAGAGAACATGGGGTCT (SEQ ID NO: 14) |
| 0.7183721 | -1.3920362 | -1 | MTX-R | TGCCAGTATTTTATTGAGGATTTTTGCATCGAGTTCAAAGTTCCACAGATCTCTAGGGCA (SEQ ID NO: 15) |
| 0.7189408 | -1.390935 | -1 | MTX-R | CTAAAAATTACATCCAGGAAATGAGATATCGAAAGAAGACATTTATGCAGCCAAAAAACA (SEQ ID NO: 16) |
| 0.722487 | -1.384108 | -1 | MTX-R | TAGGCGCACATGCACACAGCTCGCCTCTTCGATGTACAAGCTGCCTATTGATAGACTTTC (SEQ ID NO: 17) |
| 0.7254458 | -1.3784627 | -1 | MTX-R | AAAGTTGTGCAATCAGGCAAGTCAAGATTCGAAAGAAGACATTTATGCAGCCAAAAAACA (SEQ ID NO: 18) |
| 0.7374119 | -1.3560941 | -1 | MTX-R | CACCCCCATCTCCCTTTGCTGACTCTCTTCGAGTGGTGAGCAGCCAAACCAGGGTTCACT (SEQ ID NO: 19) |
| 0.7374768 | -1.3559748 | -1 | MTX-R | GGGTCTTGCTATGTTGCCCAGGCTGGCCTCGAGATCAGCCTGGGCAACACGGTGAAAACC (SEQ ID NO: 20) |
| 0.738555 | -1.3539954 | -1 | MTX-R | CTGGTTTAGTCTTGGGAGAGTGTATGIGTCGAGTTAAGCCATCTGCAAATAGCAAGAGAG (SEQ ID NO: 21) |
| 0.7415639 | -1.3485014 | -1 | MTX-R | AGCCTTGCATCCCAGGGATGAAGCCCACTCGAGATATAGATTGAGCCCCAGTTTTTGGAG (SEQ ID NO: 22) |
| 0.7422652 | -1.3472274 | -1 | MTX-R | ATCGTGTGGGCTGTGTGTGGCAGACTGTTCGAAATCGGAAGCCTCTCTGAAGGTCCAAGG (SEQ ID NO: 23) |
| 0.7430431 | -1.3458169 | -1 | MTX-R | TGCCAGTATTTTATTGAGGATTTTTGCATCGAATTCCTGGGTTTATATCCCAATCATTGT (SEQ ID NO: 24) |
| 0.7432273 | -1.3454835 | -1 | MTX-R | CACCCCCATCTCCCTTTGCTGACTCTCTTCGATATTGGTGTATATTCAAAGGGTACTTGA (SEQ ID NO: 25) |
| 1.6553355 | 1.65533547 | 1 | MTX-NR | TGATCACTGTTTCCTATGAGGATACAGCTCGAGGGGCAGGGGCGGTCCTGGGCCAGGCG (SEQ ID NO: 26) |
| 1.4321012 | 1.43210121 | 1 | MTX-NR | AACTTATGATTCTAATCTTGAATGTCTGTCGATCTATGAGGAAATGCCCCCAGCCTCCCA (SEQ ID NO: 27) |
| 1.4179763 | 1.41797626 | 1 | MTX-NR | CATAATGCATGTGCATGAAAACTAATCTTCGATCTATGAGGAAATGCCCCCAGCCTCCCA (SEQ ID NO: 28) |
| 1.4150017 | 1.41500165 | 1 | MTX-NR | ATCAGTAAGCTGGTCAGCTACCCATGAATCGATCTATGAGGAAATGCCCCCAGCCTCCCA (SEQ ID NO: 29) |
| 1.3755396 | 1.37553964 | 1 | MTX-NR | GTGTCCCAATTTCTAGTGCACTGTGAACTCGACCTCGCGGGAGGGGTGCCAGGCCGCATC (SEQ ID NO: 30) |
| 1.366009 | 1.36600904 | 1 | MTX-NR | CCGGGGCTTCTCGTTTAAGAATTCTITGTCGATCTATGAGGAAATGCCCCCAGCCTCCCA (SEQ ID NO: 31) |
| 1.3611955 | 1.36119553 | 1 | MTX-NR | GTCTTTGAAGAAGGACTAATGCTTAGTATCGAGTGCAGCGCCGGTGGGCCAGCACTGCTG (SEQ ID NO: 32) |
| 1.3408009 | 1.34080092 | 1 | MTX-NR | GTTCATTTAAACATTTTATTATGTATATTCGAGGGGCCAGGCTTTTATACCCCCATCTGA (SEQ ID NO: 33) |

TABLE 7a-continued

Example 1A. Probe and Loci data for RA-MTX -probes stratifying between responders and non-responders.

| FC | FC_1 | LS | Loop detected | 60 mer |
|---|---|---|---|---|
| 1.3350815 | 1.33508153 | 1 | MTX-NR | TTCTCCACAGCCGGCCGGTCCTTGGCAGTCGAGGGGCAGGGGCGGTCCTGGGCCAGGCG (SEQ ID NO: 34) |
| 1.3191431 | 1.31914307 | 1 | MTX-NR | GCAACACATACAACGACTAATCTTCTTTTCGACGCCGAGGAGCTCTGCAGTGGGGCGTA (SEQ ID NO: 35) |
| 1.3183444 | 1.31834441 | 1 | MTX-NR | GTAGGTGCTGAGTAAGTGAGCACTIGCCTCGAGGGGCAGGGGCGGTCCTGGGCCAGGCG (SEQ ID NO: 36) |
| 1.3164851 | 1.31648512 | 1 | MTX-NR | CAGAAAGACCTTGCAATCATACGGTGCTTCGACGCCGAGGAGCTCTGCAGTGGGGCGTA (SEQ ID NO: 37) |
| 1.3056925 | 1.3056925 | 1 | MTX-NR | TACTGTGCTGTGCTCGTCAAAGAGTATGTCGATCTATGAGGAAATGCCCCCAGCCTCCCA (SEQ ID NO: 38) |
| 1.2876529 | 1.2876529 | 1 | MTX-NR | CAGAAATTAATCAAATGCAAGTGCACCCTCGACCACCCAAGGGCTGAGGAGTGCGGGCAC (SEQ ID NO: 39) |
| 1.2777853 | 1.27778527 | 1 | MTX-NR | AAGGGACCTAGTCCCCTATTAAGATTTCTCGAGGGGCCAGGCTTTTATACCCCCATCTGA (SEQ ID NO: 40) |
| 1.2773474 | 1.2773474 | 1 | MTX-NR | CCTGCCGAGACACGGGACGTGGGATTGCTCGATCTATGAGGAAATGCCCCCAGCCTCCCA (SEQ ID NO: 41) |
| 1.2754233 | 1.2754233 | 1 | MTX-NR | CCAAAGCTCGCTTTCTTAACCACTATGCTCGAGGGGCCAGGCTTTTATACCCCCATCTGA (SEQ ID NO: 42) |
| 1.2747737 | 1.27477371 | 1 | MTX-NR | TGAATTGTGTAGCGTAAGAATTTATATCTCGAAGTTTGTGAACTGGCAGGTGGACGGGGA (SEQ ID NO: 43) |
| 1.2710171 | 1.2710171 | 1 | MTX-NR | ACCTGATCTGGGGAAGATTAGGAATTGTTCGAAACCAATTTCCTGGGATGGGGTGGGG (SEQ ID NO: 44) |
| 1.2689263 | 1.26892631 | 1 | MTX-NR | GCAAGAGGATCTCTTGAGGCCCAGGAGTTCGAGGGGCCAGGCTTTTATACCCCCATCTGA (SEQ ID NO: 45) |
| 1.2665372 | 1.2665372 | 1 | MTX-NR | TATCAAGTGATCCAAAAGGCTGCCAGTGTCGAGGGGCAGGGGCGGTCCTGGGCCAGGCG (SEQ ID NO: 46) |
| 1.2648953 | 1.26489531 | 1 | MTX-NR | AAGGGACCTAGTCCCCTATTAAGATTTCTCGAAACCAATTTCCTGGGATGGGGTGGGG (SEQ ID NO: 47) |
| 1.2592485 | 1.25924848 | 1 | MTX-NR | TATGGACTTTGTAGTCTCATATCAAAGCTCGAAACCAATTTCCTGGGATGGGGTGGGG (SEQ ID NO: 48) |
| 1.2559537 | 1.25595366 | 1 | MTX-NR | AAAAATAATCTGGCTCTACACTTAGGATTCGAAACCAATTTCCTGGGATGGGGTGGGG (SEQ ID NO: 49) |

TABLE 7b

Example 1A - Probe And Loci data for RA-MTX

| | | | Probe Location | | | | 4 kb Sequence Location | | | |
|---|---|---|---|---|---|---|---|---|---|---|
| FC | FC_1 | Chr | Start1 | End1 | Start2 | End2 | Chr | Start1 | End1 | Start2 | End2 |
| 0.5774097 | −1.7318725 | 12 | 69702274 | 69702303 | 69759619 | 69759648 | 12 | 69702274 | 69706273 | 69759619 | 69763618 |
| 0.6052669 | −1.6521636 | 7 | 22743265 | 22743294 | 22801876 | 22801905 | 7 | 22739295 | 22743294 | 22797906 | 22801905 |
| 0.6567507 | −1.5226477 | 7 | 22743265 | 22743294 | 22769055 | 22769084 | 7 | 22739295 | 22743294 | 22769055 | 22773054 |
| 0.6624775 | −1.5094851 | 7 | 22743265 | 22743294 | 22757576 | 22757605 | 7 | 22739295 | 22743294 | 22757576 | 22761575 |
| 0.6628804 | −1.5085678 | 1 | 67644699 | 67644728 | 67729398 | 67729427 | 1 | 67640729 | 67644728 | 67725428 | 67729427 |
| 0.6850588 | −1.4597286 | 12 | 69702274 | 69702303 | 69805129 | 69805158 | 12 | 69702274 | 69706273 | 69805129 | 69809128 |
| 0.6868153 | −1.4559955 | 1 | 67644699 | 67644728 | 67672222 | 67672251 | 1 | 67640729 | 67644728 | 67672222 | 67676221 |
| 0.6890053 | −1.4513676 | 1 | 67673763 | 67673792 | 67752422 | 67752451 | 1 | 67669793 | 67673792 | 67748452 | 67752451 |
| 0.6943398 | −1.4402171 | 7 | 22743265 | 22743294 | 22766800 | 22766829 | 7 | 22739295 | 22743294 | 22762830 | 22766829 |
| 0.6963019 | −1.4361587 | 4 | 123383001 | 123383030 | 123399247 | 123399276 | | 123379031 | 123383030 | 123399247 | 123403246 |
| 0.7008036 | −1.4269334 | 7 | 22743265 | 22743294 | 22765456 | 22765485 | 7 | 22739295 | 22743294 | 22765456 | 22769455 |
| 0.7132593 | −1.4020146 | 7 | 22718635 | 22718664 | 22743265 | 22743294 | 7 | 22718635 | 22722634 | 22739295 | 22743294 |
| 0.7141705 | −1.4002258 | 12 | 48397660 | 48397689 | 48423816 | 48423845 | 12 | 48397660 | 48401659 | 48423816 | 48427815 |
| 0.7156204 | −1.397389 | 17 | 32738857 | 32738886 | 32777305 | 32777334 | 17 | 32738857 | 32742856 | 32777305 | 32781304 |
| 0.7183721 | −1.3920362 | 1 | 67644699 | 67644728 | 67673763 | 67673792 | 1 | 67640729 | 67644728 | 67669793 | 67673792 |

TABLE 7b-continued

Example 1A - Probe And Loci data for RA-MTX

| | | | Probe Location | | | | 4 kb Sequence Location | | | |
|---|---|---|---|---|---|---|---|---|---|---|---|
| FC | FC_1 | Chr | Start1 | End1 | Start2 | End2 | Chr | Start1 | End1 | Start2 | End2 |
| 0.7189408 | −1.390935 | 12 | 69702274 | 69702303 | 69766052 | 69766081 | 12 | 69702274 | 69706273 | 69762082 | 69766081 |
| 0.722487 | −1.384108 | 12 | 48397660 | 48397689 | 48412400 | 48412429 | 12 | 48397660 | 48401659 | 48412400 | 48416399 |
| 0.7254458 | −1.3784627 | 12 | 69702274 | 69702303 | 69806507 | 69806536 | 12 | 69702274 | 69706273 | 69802537 | 69806536 |
| 0.7374119 | −1.3560941 | 7 | 22743265 | 22743294 | 22773903 | 22773932 | 7 | 22739295 | 22743294 | 22769933 | 22773932 |
| 0.7374768 | −1.3559748 | 19 | 55449063 | 55449092 | 55486679 | 55486708 | 19 | 55449063 | 55453062 | 55482709 | 55486708 |
| 0.738555 | −1.3539954 | 17 | 32622187 | 32622216 | 32745745 | 32745774 | 17 | 32618217 | 32622216 | 32745745 | 32749744 |
| 0.7415639 | −1.3485014 | 13 | 43129388 | 43129417 | 43181041 | 43181070 | 13 | 43125418 | 43129417 | 43181041 | 43185040 |
| | | 10 | 104130466 | 104130495 | 104156468 | 104156497 | 10 | 104126496 | 104130495 | 104152498 | 104156497 |
| 0.7430431 | −1.3458169 | 1 | 67614064 | 67614093 | 67644699 | 67644728 | 1 | 67614064 | 67618063 | 67640729 | 67644728 |
| 0.7432273 | −1.3454835 | 7 | 22743265 | 22743294 | 22798802 | 22798831 | 7 | 22739295 | 22743294 | 22798802 | 22802801 |
| 1.6553355 | 1.65533547 | 1 | 2460436 | 2460465 | 2486982 | 2487011 | 1 | 2456466 | 2460465 | 2486982 | 2490981 |
| 1.4321012 | 1.43210121 | 10 | 6391740 | 6391769 | 6577853 | 6577882 | 10 | 6391740 | 6395739 | 6577853 | 6581852 |
| 1.4179763 | 1.41797626 | 10 | 6520005 | 6520034 | 6577853 | 6577882 | 10 | 6516035 | 6520034 | 6577853 | 6581852 |
| 1.4150017 | 1.41500165 | 10 | 6427823 | 6427852 | 6577853 | 6577882 | 10 | 6427823 | 6431822 | 6577853 | 6581852 |
| 1.3755396 | 1.37553964 | 18 | 74845065 | 74845094 | 74866978 | 74867007 | 18 | 74845065 | 74849064 | 74863008 | 74867007 |
| 1.366009 | 1.36600904 | 10 | 6470268 | 6470297 | 6577853 | 6577882 | 10 | 6466298 | 6470297 | 6577853 | 6581852 |
| 1.3611955 | 1.36119553 | 20 | 44704386 | 44704415 | 44720665 | 44720694 | 20 | 44700416 | 44704415 | 44716695 | 44720694 |
| 1.3408009 | 1.34080092 | 17 | 32551069 | 32551098 | 32617664 | 32617693 | 17 | 32551069 | 32555068 | 32617664 | 32621663 |
| 1.3350815 | 1.33508153 | 1 | 2486982 | 2487011 | 2540813 | 2540842 | 1 | 2486982 | 2490981 | 2536843 | 2540842 |
| 1.3191431 | 1.31914307 | 12 | 66647072 | 66647101 | 66696510 | 66696539 | 12 | 66647072 | 66651071 | 66696510 | 66700509 |
| 1.3183444 | 1.31834441 | 1 | 2476023 | 2476052 | 2486982 | 2487011 | 1 | 2472053 | 2476052 | 2486982 | 2490981 |
| 1.3164851 | 1.31648512 | 12 | 66663907 | 66663936 | 66696510 | 66696539 | 12 | 66663907 | 66667906 | 66696510 | 66700509 |
| 1.3056925 | 1.3056925 | 10 | 6556987 | 6557016 | 6577853 | 6577882 | 10 | 6556987 | 6560986 | 6577853 | 6581852 |
| 1.2876529 | 1.2876529 | 12 | 6268999 | 6269028 | 6304632 | 6304661 | 12 | 6268999 | 6272998 | 6300662 | 6304661 |
| 1.2777853 | 1.27778527 | 17 | 32617664 | 32617693 | 32708031 | 32708060 | 17 | 32617664 | 32621663 | 32704061 | 32708060 |
| 1.2773474 | 1.2773474 | 10 | 6442502 | 6442531 | 6577853 | 6577882 | 10 | 6442502 | 6446501 | 6577853 | 6581852 |
| 1.2754233 | 1.2754233 | 17 | 32529051 | 32529080 | 32617664 | 32617693 | 17 | 32525081 | 32529080 | 32617664 | 32621663 |
| 1.2747737 | 1.27477371 | 19 | 45364170 | 45364199 | 45397229 | 45397258 | 19 | 45360200 | 45364199 | 45397229 | 45401228 |
| 1.2710171 | 1.2710171 | 17 | 32689356 | 32689385 | 32738857 | 32738886 | 17 | 32685386 | 32689385 | 32738857 | 32742856 |
| 1.2665372 | 1.2665372 | 1 | 2486982 | 2487011 | 2556784 | 2556813 | 1 | 2486982 | 2490981 | 2552814 | 2556813 |
| 1.2648953 | 1.26489531 | 17 | 32708031 | 32708060 | 32738857 | 32738886 | 17 | 32704061 | 32708060 | 32738857 | 32742856 |
| 1.2593382 | 1.25933818 | 1 | 110420097 | 110420126 | 110472386 | 110472415 | 1 | 110416127 | 110420126 | 110472386 | 110476385 |
| 1.2592485 | 1.25924848 | 17 | 32553720 | 32553749 | 32738857 | 32738886 | 17 | 32549750 | 32553749 | 32738857 | 32742856 |
| 1.2559537 | 1.25595366 | 17 | 32522613 | 32522642 | 32738857 | 32738886 | 17 | 32522613 | 32526612 | 32738857 | 32742856 |

TABLE 7c continuation of Tables 7a and 7b

| probe | Gene Locus | Probe_Count_Total | Probe_Count_Sig | Hyper_G_Stats | FDR_Hyper_G | Percent_Sig | logFC | Ave Expr | t | P. Value | Adj. P. Value | B | FC | FC_1 | LS | Loop detected |
|---|---|---|---|---|---|---|---|---|---|---|---|---|---|---|---|---|
| 12_69702273_69705360_69759618_69766081_RR | 12_69702273_69705360_69759618_69766081 | 4 | 2 | 0.034576041 | 0.518640615 | 50 | -0.792332744 | -0.792332744 | -6.352796842 | 0.001540038 | 0.2362361 | -0.525734091 | 0.577409703 | -1.731872526 | 1 | MTX-R |
| IL-6_Site4_Site5_FF | IL-6 | 48 | 13 | 7.18E-05 | 0.014530844 | 27.08 | -0.724356533 | -0.724356533 | -4.707112783 | 0.005590201 | 0.249035946 | -1.652257403 | 0.605266944 | -1.652163579 | 1 | MTX-R |
| IL-6_Site4_Site2_FR | IL-6 | 48 | 13 | 7.18E-05 | 0.014530844 | 27.08 | -0.606582168 | -0.606582168 | -6.460394591 | 0.001429141 | 0.2362361 | -0.464821575 | 0.656750743 | -1.522647688 | 1 | MTX-R |
| IL-6_Site3_FR | IL-6 | 48 | 13 | 7.18E-05 | 0.014530844 | 27.08 | -0.594056548 | -0.594056548 | -8.583674236 | 0.000391843 | 0.2362361 | 0.497776542 | 0.662477542 | -1.509485133 | 1 | MTX-R |
| IL-23R_Site4_Site2_FF | IL-23R | 104 | 19 | 0.000550011 | 0.054890393 | 18.27 | -0.593179555 | -0.593179555 | -4.111539379 | 0.009661387 | 0.255484712 | -2.16568129 | 0.662880374 | -1.508567818 | 1 | MTX-R |
| 12_69702273_69705360_69805128_69806536_RR | 12_69702273_69705360_69805128_69806536 | 4 | 2 | 0.034576041 | 0.518640615 | 50 | -0.545700188 | -0.545700188 | -11.32682228 | 0.000106595 | 0.2362361 | 1.272674673 | 0.68505884 | -1.459728628 | 1 | MTX-R |
| IL-23R_Site4_Site3_FR | IL-23R | 104 | 19 | 0.000550011 | 0.054890393 | 18.27 | -0.542005944 | -0.542005944 | -5.42869826 | 0.003062642 | 0.238248996 | -1.109864705 | 0.686815287 | -1.455995548 | 1 | MTX-R |
| IL-23R_Site3 | IL-23R | 104 | 19 | 0.000550011 | 0.054890393 | 18.27 | -0.537412982 | -0.537412982 | -5.114255946 | 0.00395047 | 0.245648426 | -1.336115162 | 0.689005315 | -1.451367613 | 1 | MTX-R |
| IL-6_Site7_FF | IL-6 | 48 | 13 | 7.18E-05 | 0.014530844 | 27.08 | -0.526286321 | -0.526286321 | -9.186377243 | 0.000285762 | 0.2362361 | 0.704172023 | 0.694339754 | -1.440217119 | 1 | MTX-R |
| IL-2_Site4_FF | IL-2 | 44 | 7 | 0.059144295 | 0.772691596 | 15.91 | -0.522215223 | -0.522215223 | -5.718310426 | 0.002446187 | 0.2362361 | -0.914385499 | 0.696301857 | -1.436158743 | 1 | MTX-R |
| IL-6_Site4_FR | IL-6 | 48 | 13 | 7.18E-05 | 0.014530844 | 27.08 | -0.512918 | -0.512918 | -7.365051101 | 0.000791901 | 0.2362361 | -0.003263498 | 0.700803556 | -1.4269334 | 1 | MTX-R |
| IL-6_Site1_FR | IL-6 | 48 | 13 | 7.18E-05 | 0.014530844 | 27.08 | -0.487501401 | -0.487501401 | -10.39123759 | 0.000160265 | 0.2362361 | 1.051647199 | 0.71325932 | -1.402014627 | 1 | MTX-R |
| IL-6_Site6_Site4_RF | | | | | | | | | | | | | | | | |

TABLE 7c-continued continuation of Tables 7a and 7b

| probe | Gene Locus | Probe_Count_Total | Probe_Count_Sig | Hyper_G_Stats | FDR_Hyper_G | Percent Sig | logFC | Ave Expr | t | P. Value | Adj. P. Value | B | FC | FC_1 | LS | Loop detected |
|---|---|---|---|---|---|---|---|---|---|---|---|---|---|---|---|---|
| COL2A1_Site2_Site5_RR | COL2A1 | 100 | 15 | 0.013266079 | 0.488432899 | 15 | -0.485659509 | -0.485659509 | -5.378633994 | 0.003186918 | 0.238248996 | -1.144888013 | 0.714170522 | -1.400225814 | 1 | MTX-R |
| CCL2_Site6_Site4_RR | CCL2 | 404 | 58 | 9.15E-06 | 0.003705017 | 14.36 | -0.482733674 | -0.482733674 | -8.467642183 | 0.000417345 | 0.2362361 | 0.455161713 | 0.715620353 | -1.397388986 | 1 | MTX-R |
| IL-23R_Site4_Site3_FF | IL-23R | 104 | 19 | 0.000550011 | 0.054890393 | 18.27 | -0.477196734 | -0.477196734 | -4.678820538 | 0.005731165 | 0.249035946 | -1.67524497 | 0.71837212 | -1.392036205 | 1 | MTX-R |
| 12_69702273_69705360_69759618_69766081_RF | 12_69702273_69705360_69759618_69766081 | 4 | 2 | 0.034576041 | 0.518640615 | 50 | -0.47605502 | -0.47605502 | -6.933158571 | 0.001041262 | 0.2362361 | -0.21283591 | 0.718940848 | -1.390935016 | 1 | MTX-R |
| COL2A1_Site2_Site4_RR | COL2A1 | 100 | 15 | 0.013266079 | 0.488432899 | 15 | -0.468956553 | -0.468956553 | -4.969850387 | 0.004457667 | 0.247336967 | -1.44516118 | 0.722486957 | -1.384108032 | 1 | MTX-R |
| 12_69702273_69705360_69805128_69806536_RF | 12_69702273_69705360_69805128_69806536 | 4 | 2 | 0.034576041 | 0.518640615 | 50 | -0.463060243 | -0.463060243 | -8.264131154 | 0.000467027 | 0.2362361 | 0.378009148 | 0.725445811 | -1.378462712 | 1 | MTX-R |
| IL-6_Site4_Site2_FF | IL-6 | 48 | 13 | 7.18E-05 | 0.014530844 | 27.08 | -0.439457343 | -0.439457343 | -9.296613034 | 0.000270277 | 0.2362361 | 0.739375667 | 0.737411927 | -1.356094149 | 1 | MTX-R |
| 19_55449062_55451429_55484960_55486708_RF | 19_55449062_55451429_55484960_55486708 | 4 | 2 | 0.034576041 | 0.518640615 | 50 | -0.439330382 | -0.439330382 | -3.343380062 | 0.021128841 | 0.2949434 | -2.923926031 | 0.737476825 | -1.355974814 | 1 | MTX-R |
| CCL2_Site10_Site13_FR | CCL2 | 404 | 58 | 9.15E-06 | 0.003705017 | 14.36 | -0.437222819 | -0.437222819 | -6.961047822 | 0.001022576 | 0.2362361 | -0.198730934 | 0.738854956 | -1.353995383 | 1 | MTX-R |
| TNFSF11_Site4_Site2_FR | TNFSF11 | 52 | 12 | 0.000677659 | 0.054890393 | 23.08 | -0.431357024 | -0.431357024 | -3.690911039 | 0.01466314 | 0.27772544 | -2.567190834 | 0.741563929 | -1.348501404 | 1 | MTX-R |
| NFKB2_Site5_Site2_FF | NFKB2 | 54 | 9 | 0.026686973 | 0.518640615 | 16.67 | -0.42999336 | -0.42999336 | -7.280958467 | 0.000834343 | 0.2362361 | -0.0426056 | 0.742265202 | -1.347227376 | 1 | MTX-R |
| IL-23R_Site5_Site4_RF | IL-23R | 104 | 19 | 0.000550011 | 0.054890393 | 18.27 | -0.428482185 | -0.428482185 | -5.623009709 | 0.002631353 | 0.2362361 | -0.997392524 | 0.743043107 | -1.345816939 | 1 | MTX-R |

TABLE 7c-continued continuation of Tables 7a and 7b

| probe | Gene Locus | Probe_Count_Total | Probe_Count_Sig | Hyper_G_Stats | FDR_Hyper_G | Percent_Sig | logFC | Ave Expr | t | P. Value | Adj. P. Value | B | FC | FC_1 | LS | Loop detected |
|---|---|---|---|---|---|---|---|---|---|---|---|---|---|---|---|---|
| IL-6_Site5_Site4 | IL-6 | 48 | 13 | 7.18E-05 | 0.014530844 | 27.08 | -0.428124668 | -0.428124668 | -7.957232876 | 0.000555975 | 0.2362361 | 0.255568458 | 0.743227265 | -1.345483471 | 1 | MTX-R |
| TNFRSF14_Site4_Site1_FR | TNFRSF14 | 112 | 14 | 0.063886514 | 0.784061767 | 12.5 | 0.727123624 | 0.727123624 | 3.49919083 | 0.017894673 | 0.286624284 | -2.761197677 | 1.655335471 | 1.655335471 | 1 | MTX-NR |
| PRKCQ_Site1_Site4_RR | PRKCQ | 213 | 31 | 0.000852984 | 0.057576386 | 14.55 | 0.518133451 | 0.518133451 | 3.441802618 | 0.019015331 | 0.289191715 | -2.820609109 | 1.432101206 | 1.432101206 | 1 | MTX-NR |
| PRKCQ_Site7_Site4_FR | PRKCQ | 213 | 31 | 0.000852984 | 0.057576386 | 14.55 | 0.503833375 | 0.503833375 | 3.563003996 | 0.016736154 | 0.282950401 | -2.695857596 | 1.417976256 | 1.417976256 | 1 | MTX-NR |
| PRKCQ_Site9 | PRKCQ | 213 | 31 | 0.000852984 | 0.057576386 | 14.55 | 0.50080374 | 0.50080374 | 3.901543743 | 0.011859009 | 0.26637802 | -2.362004516 | 1.415001654 | 1.415001654 | 1 | MTX-NR |
| 18_74845064_74846657_74864995_74867007_RF | 18_74845064_74846657_74864995_74867007 | 4 | 2 | 0.034576041 | 0.518640615 | 50 | 0.459997712 | 0.459997712 | 3.6256234 | 0.015682006 | 0.282950401 | -2.632482122 | 1.375539636 | 1.375539636 | 1 | MTX-NR |
| PRKCQ_Site2_Site4_FR | PRKCQ | 213 | 31 | 0.000852984 | 0.057576386 | 14.55 | 0.44996703 | 0.44996703 | 3.494064593 | 0.017991649 | 0.286624284 | -2.76647964 | 1.366009039 | 1.366009039 | 1 | MTX-NR |
| CD40_Site10_Site9_FF | CD40 | 142 | 17 | 0.062222744 | 0.784061767 | 11.97 | 0.444874319 | 0.444874319 | 3.596360937 | 0.016164851 | 0.282950401 | -2.662006295 | 1.36119553 | 1.36119553 | 1 | MTX-NR |
| CCL2_Site1_Site10_RR | CCL2 | 404 | 58 | 9.15E-06 | 0.003705017 | 14.36 | 0.423095044 | 0.423095044 | 4.037430853 | 0.010378328 | 0.256491595 | -2.234032001 | 1.34080092 | 1.34080092 | 1 | MTX-NR |
| TNFRSF14_Site8_RF | TNFRSF14 | 112 | 14 | 0.063886514 | 0.784061767 | 12.5 | 0.41692785 | 0.41692785 | 3.395381579 | 0.019980609 | 0.289483909 | -2.869115138 | 1.335081534 | 1.335081534 | 1 | MTX-NR |
| IRAK3_Site2_Site5_RR | IRAK3 | 75 | 11 | 0.036066824 | 0.521680846 | 14.67 | 0.399601038 | 0.399601038 | 4.778321582 | 0.005252968 | 0.249035946 | -1.594997683 | 1.319143065 | 1.319143065 | 1 | MTX-NR |
| TNFRSF14_Site6_Site1_FR | TNFRSF14 | 112 | 14 | 0.063886514 | 0.784061767 | 12.5 | 0.398727315 | 0.398727315 | 3.546617882 | 0.017025241 | 0.283912444 | -2.712563011 | 1.318344409 | 1.318344409 | 1 | MTX-NR |
| IRAK3_Site4_Site5_RR | IRAK3 | 75 | 11 | 0.036066824 | 0.521680846 | 14.67 | 0.396691209 | 0.396691209 | 6.129428964 | 0.001804535 | 0.2362361 | -0.656668121 | 1.316485115 | 1.316485115 | 1 | MTX-NR |
| PRKCQ_Site3_Site4_RR | PRKCQ | 213 | 31 | 0.000852984 | 0.057576386 | 14.55 | 0.384815172 | 0.384815172 | 4.130430098 | 0.009487914 | 0.255484712 | -2.148419919 | 1.3056925 | 1.3056925 | 1 | MTX-NR |

TABLE 7c-continued continuation of Tables 7a and 7b

| probe | Gene Locus | Probe_Count_Total | Probe_Count_Sig | Hyper_G_Stats | FDR_Hyper_G | Percent_Sig | logFC | Ave Expr | t | P. Value | Adj. P. Value | B | FC | FC_1 | LS | Loop detected |
|---|---|---|---|---|---|---|---|---|---|---|---|---|---|---|---|---|
| 12_6268998_6272753_6301795_6304661_RF | 12_6268998_6272753_6301795_6304661 | 2 | 2 | 0.006428387 | 0.289277402 | 100 | 0.364743757 | 0.364743757 | 3.5905166 | 0.016263314 | 0.282950401 | -2.667922157 | 1.287652904 | 1.287652904 | 1 | MTX-NR |
| CCL2_Site10_Site5_RF | CCL2 | 404 | 58 | 9.15E-06 | 0.003705017 | 14.36 | 0.353645409 | 0.353645409 | 4.378884995 | 0.007511833 | 0.255484712 | -1.92743217 | 1.277785266 | 1.277785266 | 1 | MTX-NR |
| PRKCQ_Site8_Site4_RR | PRKCQ | 213 | 31 | 0.000852984 | 0.057576386 | 14.55 | 0.353150952 | 0.353150952 | 4.981896454 | 0.00441255 | 0.247336967 | -1.435937375 | 1.277347404 | 1.277347404 | 1 | MTX-NR |
| CCL2_Site12_Site10_FR | CCL2 | 404 | 58 | 9.15E-06 | 0.003705017 | 14.36 | 0.350976141 | 0.350976141 | 4.528090618 | 0.006555946 | 0.251096737 | -1.800021979 | 1.275423299 | 1.275423299 | 1 | MTX-NR |
| ApoE_Site3_Site6_FR | ApoE | 96 | 17 | 0.001508547 | 0.081621699 | 17.71 | 0.350241172 | 0.350241172 | 5.557940873 | 0.002767294 | 0.2362361 | -1.021147938 | 1.27477371 | 1.27477371 | 1 | MTX-NR |
| CCL2_Site7_Site6_FR | CCL2 | 404 | 58 | 9.15E-06 | 0.003705017 | 14.36 | 0.345983436 | 0.345983436 | 3.556342165 | 0.016853001 | 0.283624894 | -2.702643166 | 1.271017097 | 1.271017097 | 1 | MTX-NR |
| CCL2_Site2_Site10_FR | CCL2 | 404 | 58 | 9.15E-06 | 0.003705017 | 14.36 | 0.343608292 | 0.343608292 | 4.809544682 | 0.005112639 | 0.249035946 | -1.570158657 | 1.268926312 | 1.268926312 | 1 | MTX-NR |
| TNFRSF14_Site1_Site9_RF | TNFRSF14 | 112 | 14 | 0.063886514 | 0.784061767 | 12.5 | 0.340889449 | 0.340889449 | 3.734122588 | 0.014030572 | 0.276682133 | -2.524417542 | 1.266537198 | 1.266537198 | 1 | MTX-NR |
| CCL2_Site5_Site6_FR | CCL2 | 404 | 58 | 9.15E-06 | 0.003705017 | 14.36 | 0.339017988 | 0.339017988 | 4.192080779 | 0.008946373 | 0.255484712 | -2.092541211 | 1.264895314 | 1.264895314 | 1 | MTX-NR |
| M-CSF_Site8_Site3_FR | M-CSF | 96 | 13 | 0.042613318 | 0.595117032 | 13.54 | 0.332665749 | 0.332665749 | 4.605504441 | 0.006116205 | 0.249035946 | -1.735449183 | 1.259338177 | 1.259338177 | 1 | MTX-NR |
| CCL2_Site11_Site6_FR | CCL2 | 404 | 58 | 9.15E-06 | 0.003705017 | 14.36 | 0.332562994 | 0.332562994 | 3.935674905 | 0.011465355 | 0.262959895 | -2.329538136 | 1.259248484 | 1.259248484 | 1 | MTX-NR |
| CCL2_Site12_Site6_RR | CCL2 | 404 | 58 | 9.15E-06 | 0.003705017 | 14.36 | 0.328783229 | 0.328783229 | 3.876162824 | 0.012161863 | 0.267229746 | -2.386288494 | 1.255953655 | 1.255953655 | 1 | MTX-NR |

TABLE 8a

Example 1 - Stratifying between RA-MTX responders and non-responders

| Probes | NR_R_P.Value | NR_R_adj.P.Val | Probe sequence 60 mer |
|---|---|---|---|
| TNFRSF14_Site4_Site1_FR | 0.001232118 | 0.079419805 | TGATCACTGTTTCCTATGAGGATACAGCTCGAGGGGCGGTCCTGGCCAGCG (SEQ ID NO: 50) |
| TNFRSF14_Site4_Site1_RR | 0.002061691 | 0.082014717 | AACCTGGAGAACGCCAAGCGCTTCGCCATCGAGGGGCAGGGGCGCGTCCTGGGCCAGCG (SEQ ID NO: 51) |
| TNFRSF1A_Site2_Site5_FR | 0.004469941 | 0.093842223 | CTACCTTTGTGCACTTGGTACAGCAAATCGACGGCCCCGTGAGGGCGGGGCGGGGACCC (SEQ ID NO: 52) |
| TNFRSF1A_Site1_Site5_FR | 0.005468033 | 0.09532964 | CATCAATTATAACTCACCTTACAGATCATCGACGGGCCCCGTGAGGCGGGGCGGGACCC (SEQ ID NO: 53) |
| TNFRSF14_Site4_Site8_FR | 0.005244102 | 0.094393734 | TGATCACTGTTTCCTATGAGAGATACAGCTCGAAGATTAGGTAAAGGTGGGACGCGAGA (SEQ ID NO: 54) |
| RUNX1_Site7_Site2_RR | 0.001313112 | 0.079419805 | GAAAGGTAATTGCCCCAATATTTATTTTCGAAACAGATCGGCGCGGCTCGGGTTACACAC (SEQ ID NO: 55) |
| TNFRSF14_Site1_Site8_RF | 0.003725772 | 0.090200643 | TTCTCCACAGCCGGCCGGTCCTTGGCAGTCGAGGGGCAGGGGCGTCTGGGCCAGGCG (SEQ ID NO: 56) |
| 18_74845064_74846657_74864995_74867007_RF | 0.001604249 | 0.079419805 | CGTGTCCCAATTCTAGTGCACTGTGAACTCGACCTCGCGGGAGGGGTGCCAGGCCGCAT (SEQ ID NO: 57) |
| PRKCZ_Site8_Site6_FR | 1.26726E-05 | 0.079228864 | CCTCTCTTCTAAAGTCTCAACATCACTCGACTGGAGAGCCCGGGGCCTCCGCGCCCGCTT (SEQ ID NO: 58) |
| RUNX1_Site5_Site2_RR | 0.000540863 | 0.079228864 | GTTTCCCTTGATGCTCAGAGAAAGGCTCGAAACAGATCGGCGCGGCTCGGGTTACACAC (SEQ ID NO: 59) |
| PRKCQ_Site7_Site4_FR | 0.003958472 | 0.090816122 | CATAATGCATGTCATGAAACTAATCTTCGATCTATGAGGAAATGCCCCAGCCTCCCA (SEQ ID NO: 60) |
| 18_74756101_74757557_74845064_74846657_RR | 0.003489147 | 0.089578901 | AGATGTGTAAGTCACCAGGGAGTGCATTCGCGACCTCGCGGGAGGGGTGCCAGGCCGCAT (SEQ ID NO: 61) |
| PRKCQ_Site10_Site4_FR | 0.004639159 | 0.093842223 | GTAATGGTGCCATCATCATAGCTCAAGCTCCTCGATCTATGAGGAAATGCCCCAGCCTCCCA (SEQ ID NO: 62) |
| PRKCQ_Site10_Site4_RR | 0.007812066 | 0.108064059 | AATACAAAGGATGGTATATTTTGCATATTCGATCTATGAGGAAATGCCCCAGCCTCCCA (SEQ ID NO: 63) |
| PRKCZ_Site8_Site9_FR | 0.000560117 | 0.079228864 | CCTCTCTTCTAAAAGGTCTCAACATCACTCGATGGTGCGGAGGTGGCCGGCAGGGTTGG (SEQ ID NO: 64) |

TABLE 8a-continued

Example 1 - Stratifying between RA-MTX responders and non-responders

| Probes | NR_R_P.Value | NR_R_adj.P.Val | Probe sequence 60 mer |
|---|---|---|---|
| MTHFD1_Site5_Site1_RF | 0.000404338 | 0.079228864 | ATAATTCTTCCTGGCACATAATAAGTATTCGAATCGGCGGGTTCCGGCGTGGGTTTCAG (SEQ ID NO: 65) |
| NFAT_Site6_Site1_FF | 0.000514351 | 0.079228864 | TCTAAAGGGATTTCCACTATATGTAGATTCGAGGGGCGTGTGCGCGCGTGGCGGGGCCCG (SEQ ID NO: 66) |
| PRKCQ_Site11_Site4_RR | 0.006796573 | 0.102494645 | AACTTATGATTCTAATCTTGAATGTCGTCGATCTATGAGGAAATGCCCCCAGCCTCCCA (SEQ ID NO: 67) |
| TNFRSF1A_Site5_Site6_FF | 0.011987094 | 0.126537326 | GAGGTGGGCAGATCACCGGGGTCAGGGTATCGAGGCCCATCACTGGCGGGAGACGGGAGG (SEQ ID NO: 68) |
| 18_74845064_74846657_74864266_74864995_RF | 0.008686097 | 0.111746517 | ACTGAATATGAAAAAAAATGTAAAAATTATCGACCTCCGCGGGAGGGGTGCCAGGCCCAT (SEQ ID NO: 69) |
| PRKCQ_Site7_Site4_RR | 0.011239245 | 0.123381356 | GATTTTATAGCAAATTTACAAAAATGAGTCGATCTATGAGGAAATGCCCCCAGCCTCCCA (SEQ ID NO: 70) |
| PRKCZ_Site5_Ste9_RR | 0.002885944 | 0.086622849 | ACCAAGAGTTGGACCCCCCTTTTTGATGTTCGATGGTGCGGAGGTGGCCGGCCAGGGTTGG (SEQ ID NO: 71) |
| MAL_Site4_Site2_FR | 0.000818457 | 0.079228864 | TATATTGCTATCTACTAGCAAAGGATAATCGAAGAGAGTTCAGGGCGCGTGCCGCGGCGCT (SEQ ID NO: 72) |
| PRKCQ_Site9_Site4_RR | 0.003669785 | 0.090206643 | ATCAGTAAGCTGTCAGCTACCCATGAATCGATCTATGAGGAAATGCCCCCAGCCTCCCA (SEQ ID NO: 73) |
| TNFRSF14_Site_Site8_FR | 0.000995361 | 0.079228864 | TGAAAACAGTTCATCCTGAGTTTCAGTCTCGAAGATTAGGTAAAGGTGGGGACGCGGAGA (SEQ ID NO: 74) |
| IFNAR1_Site2_Site4_RR | 0.004801376 | 0.093849223 | GTGCAGAGCGAGAGCGGGCAGAGGCCGTCGAAACTCGGAGAATTCATCTGAAATGATTA (SEQ ID NO: 75) |
| IL-21R_Site5_Site2_RR | 0.034533931 | 0.199109911 | GAGGCAGGCAGATCATGAGGTCAGGAGTTCGAGCCCTGGACCCCAGCTAATGAGG (SEQ ID NO: 76) |
| 19_10326358_10327821_10368389_10370560_RR | 0.000174676 | 0.079228864 | GCTCACTGCAACCTCCACCTCCCAGGTTCGCGAACCTCCTGATAACTTCAGCATTAACAG (SEQ ID NO: 77) |
| 19_55449062_55451429_55484960_55486708_RF | 7.78E-05 | 0.079228864 | AGGGTCTTGCTATGTTGCCCAGGCTCGAAGCCTCCGAGATCAGCCTGGGCAACACCGTGAAAAC (SEQ ID NO: 78) |
| TLR1_Site4_Site7_FR | 0.000969535 | 0.079228864 | TGTAATATAAGCATAGCTCACTGCAGCCTCGAAGCATTTGTACGACATTCTCATCTTCTT (SEQ ID NO: 79) |
| IRF5_Site8_Site2_FF | 0.000148986 | 0.079228864 | ACAGAGGAGCGAGGCCCGATCCTTACTTTCGAACTCCTGACCTCGTGATCTGCCCACCTC (SEQ ID NO: 80) |

TABLE 8a-continued

Example 1 - Stratifying between RA-MTX responders and non-responders

| Probes | NR_R_P.Value | NR_R_adj.P.Val | Probe sequence 60 mer |
|---|---|---|---|
| SPRED2_Site4_Site8_RF | 0.018236449 | 0.149371667 | GGGTTTCACCATGTTAGCCAGGATGGTCTCGATCTCCrGACCTCATGATCCGCCTGCCTC (SEQ ID NO: 81) |
| IKBKB_Site5_Site8_FR | 0.013123191 | 0.130076121 | GCATTTCACCATGTTGGTGAGGCTGGTCTCGAAGAGTTCACACGTGTCCAAATTTGGTGG (SEQ ID NO: 82) |
| TLR1_Site9_Site2_FF | 0.002914123 | 0.086622849 | CTGGGATCACAGGCATGTGCCACCATGCTCGACAAGAATAGTCTCCTTGTTTCTGAACAT (SEQ ID NO: 83) |
| CD28_Site1_Site9_RR | 0.003257956 | 0.088621062 | GTATTTCTGGTTCTAGATCCTTGAGGAATCGAGCAGAAGGAGTCTCTCCCTGAGGCCACC (SEQ ID NO: 84) |
| 12_10289678_10290500_10350455_10351677_RF | 0.001491578 | 0.079419805 | CGAGGCGGGCGGATCACGAGGTCAGGAGATCGACCCCACGTTCTCACCACCTGTTTCTT (SEQ ID NO: 85) |
| CD28_Site1_Site8_RR | 0.007644106 | 0.107723492 | GTATTTCTGGTTCTAGATCCTTGAGGAATCGACCTCTCTGGGCTCAACCTATCCTCCCACC (SEQ ID NO: 86) |
| CXCL8_Site2_Site6_RF | 0.002891692 | 0.086622849 | GGGTTTCACTGTGTTAGCCAGGATGGTCTCGACCTCCCTGGCTCAAGTGATCTTCCCACC (SEQ ID NO: 87) |
| IL-23R_Site4_Site3_RF | 0.001588257 | 0.079419805 | TGCCCTAGAGATCTGTGAACTTGAACTCGATATATGAAAATAGTTTTAATTATAAA (SEQ ID NO: 88) |
| RBPJ_Site14_Site13_FF | 0.010539749 | 0.118804917 | GGTGGGGAATCACTTGAGGTCAGAAGTTCGAGACCATCCTGGCAACATGGTAAAACCC (SEQ ID NO: 89) |
| CHUK_Site7_Site2_RF | 0.000132328 | 0.079228864 | AATGGCACGATCACGGCTCACTCGAGCCTCGAATGTTACTGACAGTGGACACAGTAAGAA (SEQ ID NO: 90) |
| SH2B3_Site6_Site5_FF | 0.003743845 | 0.090200643 | GAGTTTTGCCATGTTGCCCAGGCTGGTCTCGAGAACAGCCTGCCAACATGGTGAAACCC (SEQ ID NO: 91) |
| IRAK3_Site7_Site5_FR | 0.00056928 | 0.079228864 | AGGTCTCACTATGTTGCCGAGGCTGGTCTCGACGCCCGAGGAGCTCTGCAGTGGGGCGTA (SEQ ID NO: 92) |
| CD28_Site4_Site2_RF | 0.014801185 | 0.136839161 | GGGTTTCACCATGTTGGCGAGGCTGGTCTCGAACTCCTGACCTCAGGTGATCCGCCTGCC (SEQ ID NO: 93) |
| CD28_Site5_Site6_FR | 0.007402719 | 0.106291976 | GGTGGGTGGATCACCTGAGGTCAGGAGTTCGACCTAAGGGTGGTCATAATTCTGCTGTCTG (SEQ ID NO: 94) |
| 19_39424583_39425930_39445791_39449626_FF | 0.001743055 | 0.079577656 | GGGTCTCACAGCTTCAGAGCTGAGAGCCTAGGCTTCAGTGAGCCATAATCACGCCACTA (SEQ ID NO: 95) |
| IL-1a_and_IL-1b_Site1_Site7_RF | 0.002815998 | 0.086622849 | CTTTGGGAGGCCAAGGTGAGTGCTTGACATCTCATTTGATAGATTAAGTCAACG (SEQ ID NO: 96) |

TABLE 8a-continued

Example 1 - Stratifying between RA-MTX responders and non-responders

| Probes | NR_R_P.Value | NR_R_adj.P.Val | Probe sequence 60 mer |
|---|---|---|---|
| IRAK3_Site7_Site1_FF | 0.00166033 | 0.079419805 | AGGTCTCCACTATGTTGCCCGGGCTGGTCTCGAACAGCAGCGTGTGCCGCCGAGCGCGCC (SEQ ID NO: 97) |
| C5orf30_Site2_Site8_FR | 0.00524841 | 0.094393734 | TCTGTCGCCCAGTTGGAGTACAGTGGCTCGAGGATGTCCTATTTGCCACCTTATCTAA (SEQ ID NO: 98) |
| CXCL13_Site1_Site3_RR | 6.56394E-05 | 0.079228864 | TTATATCTCCTACCTCCAAGCCTGGCAGTCGATTCCAAAGTGAAGCAAAAAAAAACTTC (SEQ ID NO: 99) |
| 14_55507409_55508411_55583475_55586339_RF | 0.003368236 | 0.088703855 | AAAGACCCTGTCTCTAAATAATAGAACATCGAGATCATGCCACTGACTCCAGCCTGGG (SEQ ID NO: 100) |
| 14_91450408_91451505_91524833_91527062_FF | 0.004287708 | 0.093190996 | GGGGTTTTTCCATGTTAGTCAGGCTGGTCTAATGGCTCCCTTACCTTGCTGGCTGTGGGC (SEQ ID NO: 101) |
| IL-23_Site4_Site5_FR | 0.021765214 | 0.160960834 | AGTGGCATGATCACAGCTCACTGCCACCTCGAAACCAAACCCTGTGACTTCAACACCCAA (SEQ ID NO: 102) |
| IL-17A_Site3_Site1_RR | 0.009698852 | 0.115042065 | CCCTCCCTCAACATGCAGGGATTACAATTCGAAGATGTCTGAAGGAAGCAATTGGGAAA (SEQ ID NO: 103) |

TABLE 8b

Example 1 - Stratifying between RA-MTX responders and non-responders

| Probe Location | | | | | 4 kb Sequence Location | | | | |
|---|---|---|---|---|---|---|---|---|---|
| Chr | Start1 | End1 | Start2 | End2 | Chr | Start1 | End1 | Start2 | End2 |
| 1 | 2460436 | 2460465 | 2486982 | 2487011 | 1 | 2456466 | 2460465 | 2486982 | 2490981 |
| 1 | 2457910 | 2457939 | 2486982 | 2487011 | 1 | 2457910 | 2461909 | 2486982 | 2490981 |
| 12 | 6443253 | 6443282 | 6472689 | 6472718 | 12 | 6439283 | 6443282 | 6472689 | 6476688 |
| 12 | 6452140 | 6452169 | 6472689 | 6472718 | 12 | 6448170 | 6452169 | 6472689 | 6476688 |
| 1 | 2460436 | 2460465 | 2539015 | 2539044 | 1 | 2456466 | 2460465 | 2539015 | 2543014 |
| 21 | 36117642 | 36117671 | 36260589 | 36260618 | 21 | 36117642 | 36121641 | 36260589 | 36264588 |
| 1 | 2486982 | 2487011 | 2540813 | 2540842 | 1 | 2486982 | 2490981 | 2536843 | 2540842 |
| 18 | 74845065 | 74845094 | 74866978 | 74867007 | 18 | 74845065 | 74849064 | 74863008 | 74867007 |
| 1 | 1977899 | 1977928 | 2066129 | 2066158 | 1 | 1973929 | 1977928 | 2066129 | 2070128 |
| 21 | 36206580 | 36206609 | 36260589 | 36260618 | 21 | 36206580 | 36210579 | 36260589 | 36264588 |
| 10 | 6520005 | 6520034 | 6577853 | 6577882 | 10 | 6516035 | 6520034 | 6577853 | 6581852 |
| 18 | 74756102 | 74756131 | 74845065 | 74845094 | 18 | 74756102 | 74760101 | 74845065 | 74849064 |
| 10 | 6454073 | 6454102 | 6577853 | 6577882 | 10 | 6450103 | 6454102 | 6577853 | 6581852 |
| 10 | 6448929 | 6448958 | 6577853 | 6577882 | 10 | 6448929 | 6452928 | 6577853 | 6581852 |
| 1 | 1977899 | 1977928 | 2125692 | 2125721 | 1 | 1973929 | 1977928 | 2125692 | 2129691 |
| 14 | 64856944 | 64856973 | 64805460 | 64805493 | 14 | 64852973 | 64856973 | 64805460 | 64801460 |
| 18 | 77135881 | 77135910 | 77156058 | 77156087 | 18 | 77131911 | 77135910 | 77152088 | 77156087 |
| 10 | 6391740 | 6391769 | 6577853 | 6577882 | 10 | 6391740 | 6395739 | 6577853 | 6581852 |
| 12 | 6473688 | 6473717 | 6494374 | 6494403 | 12 | 6469717 | 6473717 | 6490404 | 6494403 |
| 18 | 74845065 | 74845094 | 74864966 | 74864995 | 18 | 74845065 | 74849064 | 74860996 | 74864995 |
| 10 | 6515356 | 6515385 | 6577853 | 6577882 | 10 | 6515356 | 6519355 | 6577853 | 6581852 |
| 1 | 2035712 | 2035741 | 2125692 | 2125721 | 1 | 2035712 | 2039711 | 2125692 | 2129691 |
| 2 | 95655673 | 95655703 | 95691307 | 95691336 | 2 | 95651704 | 95655703 | 95691307 | 95695306 |
| 10 | 6427823 | 6427852 | 6577853 | 6577882 | 10 | 6427823 | 6431822 | 6577853 | 6581852 |
| 1 | 2483531 | 2483560 | 2539015 | 2539044 | 1 | 2479561 | 2483560 | 2539015 | 2543014 |
| 21 | 34696685 | 34696714 | 34746263 | 34746292 | 21 | 34696685 | 34700684 | 34746263 | 34750262 |
| 16 | 27367634 | 27367663 | 27460580 | 27460609 | 16 | 27367634 | 27371633 | 27460580 | 27464579 |
| 19 | 10326359 | 10326388 | 10368390 | 10368419 | 19 | 10326359 | 10330358 | 10368390 | 10372389 |
| 19 | 55449063 | 55449092 | 55486679 | 55486708 | 19 | 55449063 | 55453062 | 55482709 | 55486708 |
| 4 | 38794092 | 38794121 | 38904213 | 38904242 | 4 | 38790122 | 38794121 | 38904213 | 38908212 |
| 7 | 128578517 | 128578546 | 128592079 | 128592108 | 7 | 128574547 | 128578546 | 128588109 | 128592108 |
| 2 | 65604070 | 65604099 | 65634253 | 65634282 | 2 | 65604070 | 65608069 | 65630283 | 65634282 |
| 8 | 42092338 | 42092367 | 42202562 | 42202591 | 8 | 42088368 | 42092367 | 42202562 | 42206561 |
| 4 | 38788263 | 38788292 | 38859677 | 38859706 | 4 | 38784293 | 38788292 | 38855707 | 38859706 |
| 2 | 204566973 | 204567002 | 204624489 | 204624518 | 2 | 204566973 | 204570972 | 204624489 | 204628488 |
| 12 | 10289679 | 10289708 | 10351648 | 10351677 | 12 | 10289679 | 10293678 | 10347678 | 10351677 |
| 2 | 204566973 | 204567002 | 204645538 | 204645567 | 2 | 204566973 | 204570972 | 204645538 | 204649537 |
| 4 | 74601393 | 74601422 | 74662726 | 74662755 | 4 | 74601393 | 74605392 | 74658756 | 74662755 |
| 1 | 67639374 | 67639403 | 67673763 | 67673792 | 1 | 67639374 | 67643373 | 67669793 | 67673792 |
| 4 | 26109288 | 26109317 | 26147759 | 26147788 | 4 | 26105374 | 26109317 | 26143789 | 26147788 |
| 10 | 101933094 | 101933123 | 101989686 | 101989715 | 10 | 101933094 | 101937093 | 101985716 | 101989715 |
| 12 | 111834072 | 111834101 | 111901271 | 111901300 | 12 | 111830102 | 111834101 | 111897301 | 111901300 |
| 12 | 66544383 | 66544412 | 66696510 | 66696539 | 12 | 66540413 | 66544412 | 66696510 | 66700509 |
| 2 | 204522870 | 204522899 | 204607547 | 204607576 | 2 | 204522870 | 204526869 | 204603577 | 204607576 |
| 2 | 204541606 | 204541635 | 204582161 | 204582190 | 2 | 204537636 | 204541635 | 204582161 | 204586160 |
| 19 | 39425901 | 39425930 | 39449597 | 39449626 | 19 | 39421931 | 39425930 | 39445627 | 39449626 |
| 2 | 113627760 | 113627789 | 113530289 | 113530318 | 2 | 113623789 | 113627789 | 113530289 | 113526289 |
| 12 | 66544383 | 66544412 | 66583104 | 66583133 | 12 | 66540413 | 66544412 | 66579134 | 66583133 |
| 5 | 102618306 | 102618335 | 102629447 | 102629476 | 5 | 102614336 | 102618335 | 102629447 | 102633446 |
| 4 | 78431568 | 78431597 | 78523781 | 78523810 | 4 | 78431568 | 78435567 | 78523781 | 78527780 |
| 14 | 55507410 | 55507439 | 55586310 | 55586339 | 14 | 55507410 | 55511409 | 55582340 | 55586339 |
| 14 | 91451476 | 91451505 | 91527033 | 91527062 | 14 | 91447506 | 91451505 | 91523063 | 91527062 |
| 12 | 56741028 | 56741057 | 56754855 | 56754884 | 12 | 56737058 | 56741057 | 56754855 | 56758854 |
| 6 | 52026497 | 52026526 | 52049432 | 52049461 | 6 | 52026497 | 52030496 | 52049432 | 52053431 |

TABLE 9a

Example 1A-RA vs. healthy (HC)

| probe | GeneLocus | Probe_Count_Total | Probe_Count_Sig | HyperG_Stats | FDR_HyperG | Percent_Sig | reps.. |
|---|---|---|---|---|---|---|---|
| 3_112025276_112034935_112084448_112086795_RR | CD200 | 26 | 8 | 0.0009 | 0.034641 | 30.77 | 4 |
| 7_80168823_80173631_80193869_80200362_FF | CD36 | 127 | 31 | 3.33E-08 | 1.03E-05 | 24.41 | 2 |
| 10_98399260_98400639_98464393_98468588_RR | PIK3AP1 | 210 | 32 | 0.000597 | 0.026269 | 15.24 | 4 |
| 10_98397707_98399014_98464393_98468588_RR | PIK3AP1 | 210 | 32 | 0.000597 | 0.026269 | 15.24 | 2 |
| 10_98426247_98429729_98464393_98468588_RR | PIK3AP1 | 210 | 32 | 0.000597 | 0.026269 | 15.24 | 2 |
| 5_7348279_7353422_7459585_7461017_RR | ADCY2 | 364 | 41 | 0.028605 | 0.534587 | 11.26 | 4 |
| 1_167474157_167477896_167516923_167519477_FF | CD247 | 254 | 28 | 0.076338 | 0.800928 | 11.02 | 4 |
| 10_98413942_98416630_98464393_98468588_RR | PIK3AP1 | 210 | 32 | 0.000597 | 0.026269 | 15.24 | 3 |
| 10_98406449_98407502_98464393_98468588_RR | PIK3AP1 | 210 | 32 | 0.000597 | 0.026269 | 15.24 | 2 |

TABLE 9a-continued

Example 1A-RA vs. healthy (HC)

| probe | GeneLocus | Probe_Count_Total | Probe_Count_Sig | HyperG_Stats | FDR_HyperG | Percent_Sig | reps.. |
|---|---|---|---|---|---|---|---|
| 10_98374146_98380277_98464393_98468588_FR | PIK3AP1 | 210 | 32 | 0.000597 | 0.026269 | 15.24 | 4 |
| 10_98397707_98399014_98464393_98468588_FR | PIK3AP1 | 210 | 32 | 0.000597 | 0.026269 | 15.24 | 3 |
| 22_40991346_40993921_41008883_41010718_FR | MKL1 | 183 | 29 | 0.000555 | 0.026269 | 15.85 | 3 |
| 5_7375991_7381724_7459585_7461017_RF | ADCY2 | 364 | 41 | 0.028605 | 0.534587 | 11.26 | 4 |
| 22_40896154_40899434_41056322_41063897_FF | MKL1 | 183 | 29 | 0.000555 | 0.026269 | 15.85 | 2 |
| 10_98442806_98446178_98464393_98468588_FR | PIK3AP1 | 210 | 32 | 0.000597 | 0.026269 | 15.24 | 3 |
| 10_98464393_98468588_98520690_98524157_RF | PIK3AP1 | 210 | 32 | 0.000597 | 0.026269 | 15.24 | 4 |
| 10_98362077_98370186_98464393_98468588_FR | PIK3AP1 | 210 | 32 | 0.000597 | 0.026269 | 15.24 | 4 |
| 3_112025276_112034935_112094416_112098885_RR | CD200 | 26 | 8 | 0.0009 | 0.034641 | 30.77 | 4 |
| 5_7402050_7407728_7612925_7619203_RR | ADCY2 | 364 | 41 | 0.028605 | 0.534587 | 11.26 | 4 |
| 10_98362077_98370186_98464393_98468588_RR | PIK3AP1 | 210 | 32 | 0.000597 | 0.026269 | 15.24 | 3 |
| 11_93832833_93843526_93895630_93897747_FR | PANX1 | 29 | 5 | 0.088438 | 0.801142 | 17.24 | 2 |
| 10_98413942_98416630_98464393_98468588_FR | PIK3AP1 | 210 | 32 | 0.000597 | 0.026269 | 15.24 | 4 |
| 11_93843526_93849067_93895630_93897747_RR | PANX1 | 29 | 5 | 0.088438 | 0.801142 | 17.24 | 4 |
| 10_98442806_98446178_98464393_98468588_RR | PIK3AP1 | 210 | 32 | 0.000597 | 0.026269 | 15.24 | 4 |
| 22_40871339_40876622_41008883_41010718_FR | MKL1 | 183 | 29 | 0.000555 | 0.026269 | 15.85 | 4 |
| 22_40848625_40853672_41008883_41010718_FR | MKL1 | 183 | 29 | 0.000555 | 0.026269 | 15.85 | 4 |
| 17_73322245_73323380_73394039_73395972_FF | GRB2 | 270 | 32 | 0.026522 | 0.534587 | 11.85 | 4 |
| 2_173587206_173590304_173788215_173791519_FF | RAPGEF4 | 195 | 22 | 0.088283 | 0.801142 | 11.28 | 3 |
| X_19753406_19760963_19778202_19779729_RF | SH3KBP1 | 291 | 33 | 0.042262 | 0.681595 | 11.34 | 4 |
| 22_40796444_40801147_40909402_40912220_RR | MKL1 | 183 | 29 | 0.000555 | 0.026269 | 15.85 | 4 |
| 22_40896154_40899434_40931576_40935727_FF | MKL1 | 183 | 29 | 0.000555 | 0.026269 | 15.85 | 4 |
| 22_40796444_40801147_40871339_40876622_RR | MKL1 | 183 | 29 | 0.000555 | 0.026269 | 15.85 | 4 |
| 7_55061795_55064635_55224588_55235839_RR | EGFR | 209 | 35 | 5.02E−05 | 0.007733 | 16.75 | 4 |
| 11_119100257_119101910_119157901_119160975_FR | CBL | 41 | 7 | 0.050372 | 0.71046 | 17.07 | 3 |
| 1_167399005_167402982_167413430_167415364_RF | CD247 | 254 | 28 | 0.076338 | 0.800928 | 11.02 | 4 |
| 22_40909402_40912220_40931576_40935727_RF | MKL1 | 183 | 29 | 0.000555 | 0.026269 | 15.85 | 4 |
| 17_73352725_73353799_73428595_73430537_RF | GRB2 | 270 | 32 | 0.026522 | 0.534587 | 11.85 | 4 |
| 7_80168823_80173631_80308967_80317006_FF | CD36 | 127 | 31 | 3.33E−08 | 1.03E−05 | 24.41 | 4 |
| 22_40909402_40912220_41075227_41079714_RF | MKL1 | 183 | 29 | 0.000555 | 0.026269 | 15.85 | 4 |
| X_19545819_19548298_19747473_19749276_FF | SH3KBP1 | 291 | 33 | 0.042262 | 0.681595 | 11.34 | 4 |
| 10_98401433_98405814_98464393_98468588_RR | PIK3AP1 | 210 | 32 | 0.000597 | 0.026269 | 15.24 | 4 |
| 17_73347837_73349062_73428595_73430537_RF | GRB2 | 270 | 32 | 0.026522 | 0.534587 | 11.85 | 4 |
| X_19644496_19650796_19920428_19925492_FF | SH3KBP1 | 291 | 33 | 0.042262 | 0.681595 | 11.34 | 2 |
| 7_80078955_80088693_80121443_80124810_RR | CD36 | 127 | 31 | 3.33E−08 | 1.03E−05 | 24.41 | 4 |
| 22_40871339_40876622_40909402_40912220_RR | MKL1 | 183 | 29 | 0.000555 | 0.026269 | 15.85 | 4 |
| 22_40888137_40890603_41008883_41010718_RR | MKL1 | 183 | 29 | 0.000555 | 0.026269 | 15.85 | 2 |
| 11_93858215_93861587_93895630_93897747_FR | PANX1 | 29 | 5 | 0.088438 | 0.801142 | 17.24 | 4 |
| 22_40909402_40912220_41008883_41010718_FR | MKL1 | 183 | 29 | 0.000555 | 0.026269 | 15.85 | 2 |
| 22_40909402_40912220_40944160_40947074_RF | MKL1 | 183 | 29 | 0.000555 | 0.026269 | 15.85 | 3 |
| 17_73401174_73403644_73443323_73445724_FF | GRB2 | 270 | 32 | 0.026522 | 0.534587 | 11.85 | 4 |

TABLE 9b

Example 1A - RA vs. healthy (HC)

| Avg_CV | logFC | AveExpr | t | P.Value | adj.P.Val | B | FC | FC_1 | LS.x | Loop detected |
|---|---|---|---|---|---|---|---|---|---|---|
| 22.5672 | 0.685577 | 0.685577 | 7.208757 | 6.20E−05 | 0.067791 | 2.137374 | 1.608346 | 1.608346 | 1 | RA |
| 2.8578 | 0.513592 | 0.513592 | 5.758269 | 0.000319 | 0.067791 | 0.70324 | 1.4276 | 1.4276 | 1 | RA |
| 3.9824 | 0.509022 | 0.509022 | 5.490428 | 0.000444 | 0.067791 | 0.402326 | 1.423085 | 1.423085 | 1 | RA |
| 4.8484 | 0.49927 | 0.49927 | 5.744216 | 0.000324 | 0.067791 | 0.687747 | 1.413498 | 1.413498 | 1 | RA |
| 3.7034 | 0.497429 | 0.497429 | 5.438056 | 0.000474 | 0.067791 | 0.342088 | 1.411696 | 1.411696 | 1 | RA |
| 25.3272 | 0.481183 | 0.481183 | 5.488293 | 0.000445 | 0.067791 | 0.39988 | 1.395888 | 1.395888 | 1 | RA |
| 3.902 | 0.477912 | 0.477912 | 4.775775 | 0.001128 | 0.084274 | 0.459904 | 1.392726 | 1.392726 | 1 | RA |
| 3.4802 | 0.473702 | 0.473702 | 5.498122 | 0.000439 | 0.067791 | 0.411136 | 1.388668 | 1.388668 | 1 | RA |
| 4.5316 | 0.466456 | 0.466456 | 5.514684 | 0.00043 | 0.067791 | 0.430069 | 1.381711 | 1.381711 | 1 | RA |
| 4.3162 | 0.464731 | 0.464731 | 4.947314 | 0.000895 | 0.079113 | 0.244976 | 1.38006 | 1.38006 | 1 | RA |
| 4.07 | 0.450917 | 0.450917 | 5.861317 | 0.000281 | 0.067791 | 0.815863 | 1.366909 | 1.366909 | 1 | RA |
| 2.468 | 0.449615 | 0.449615 | 6.187618 | 0.000191 | 0.067791 | 1.161199 | 1.365676 | 1.365676 | 1 | RA |
| 28.4296 | 0.44389 | 0.44389 | 6.177656 | 0.000193 | 0.067791 | 1.150906 | 1.360267 | 1.360267 | 1 | RA |
| 1.959 | 0.434213 | 0.434213 | 5.114367 | 0.000718 | 0.076048 | −0.04052 | 1.351174 | 1.351174 | 1 | RA |
| 4.0442 | 0.433359 | 0.433359 | 5.322391 | 0.000549 | 0.070404 | 0.207413 | 1.350374 | 1.350374 | 1 | RA |
| 4.3738 | 0.433217 | 0.433217 | 4.906707 | 0.000945 | 0.079113 | 0.295398 | 1.350241 | 1.350241 | 1 | RA |
| 3.6068 | 0.431233 | 0.431233 | 5.069327 | 0.000762 | 0.078192 | 0.095173 | 1.348386 | 1.348386 | 1 | RA |
| 7.675 | 0.430701 | 0.430701 | 3.417531 | 0.008129 | 0.14654 | 2.330752 | 1.347889 | 1.347889 | 1 | RA |
| 2.4692 | 0.429497 | 0.429497 | 4.529234 | 0.001583 | 0.094398 | 0.777617 | 1.346764 | 1.346764 | 1 | RA |
| 6.9092 | 0.424613 | 0.424613 | 4.919181 | 0.00093 | 0.079113 | 0.279879 | 1.342212 | 1.342212 | 1 | RA |
| 0.861 | 0.418444 | 0.418444 | 3.453029 | 0.007695 | 0.144805 | 2.278502 | 1.336486 | 1.336486 | 1 | RA |
| 3.8908 | 0.418119 | 0.418119 | 4.618943 | 0.001398 | 0.092869 | 0.660814 | 1.336184 | 1.336184 | 1 | RA |
| 3.9704 | 0.412721 | 0.412721 | 3.265842 | 0.01029 | 0.157013 | −2.55552 | 1.331194 | 1.331194 | 1 | RA |

TABLE 9b-continued

Example 1A - RA vs. healthy (HC)

| Avg_CV | logFC | AveExpr | t | P.Value | adj.P.Val | B | FC | FC_1 | LS.x | Loop detected |
|---|---|---|---|---|---|---|---|---|---|---|
| 4.374 | 0.411793 | 0.411793 | 4.953972 | 0.000888 | 0.079113 | 0.236736 | 1.330338 | 1.330338 | 1 | RA |
| 2.2892 | 0.399862 | 0.399862 | 5.585453 | 0.000394 | 0.067791 | 0.510449 | 1.319382 | 1.319382 | 1 | RA |
| 3.2674 | 0.398739 | 0.398739 | 5.342329 | 0.000535 | 0.06998 | 0.230789 | 1.318355 | 1.318355 | 1 | RA |
| 4.4132 | 0.397225 | 0.397225 | 4.054922 | 0.003115 | 0.118804 | −1.417412 | 1.316972 | 1.316972 | 1 | RA |
| 4.4052 | 0.395013 | 0.395013 | 5.008 | 0.000826 | 0.079113 | −0.170148 | 1.314955 | 1.314955 | 1 | RA |
| 29.626 | 0.393804 | 0.393804 | 3.646302 | 0.005726 | 0.137876 | −1.996639 | 1.313853 | 1.313853 | 1 | RA |
| 2.9968 | 0.388334 | 0.388334 | 3.462029 | 0.007589 | 0.144805 | −2.265278 | 1.308881 | 1.308881 | 1 | RA |
| 3.9034 | 0.386289 | 0.386289 | 4.286116 | 0.00223 | 0.107797 | −1.100959 | 1.307027 | 1.307027 | 1 | RA |
| 4.137 | 0.385157 | 0.385157 | 3.466476 | 0.007538 | 0.144805 | −2.258746 | 1.306002 | 1.306002 | 1 | RA |
| 16.4644 | 0.3851 | 0.3851 | 2.766312 | 0.022719 | 0.20414 | −3.307709 | 1.30595 | 1.30595 | 1 | RA |
| 4.0986 | 0.385001 | 0.385001 | 5.604724 | 0.000385 | 0.067791 | 0.532193 | 1.305861 | 1.305861 | 1 | RA |
| 16.621 | 0.384436 | 0.384436 | 2.93912 | 0.017235 | 0.186238 | −3.046125 | 1.305349 | 1.305349 | 1 | RA |
| 2.9874 | 0.37983 | 0.37983 | 3.321482 | 0.009435 | 0.152196 | −2.472807 | 1.301188 | 1.301188 | 1 | RA |
| 3.5382 | 0.379663 | 0.379663 | 5.968229 | 0.000247 | 0.067791 | 0.930887 | 1.301038 | 1.301038 | 1 | RA |
| 26.1988 | 0.37908 | 0.37908 | 4.66095 | 0.001319 | 0.089846 | −0.606589 | 1.300513 | 1.300513 | 1 | RA |
| 3.7712 | 0.37846 | 0.37846 | 3.732483 | 0.005026 | 0.129648 | −1.872495 | 1.299954 | 1.299954 | 1 | RA |
| 5.4524 | 0.377994 | 0.377994 | 4.038461 | 0.003191 | 0.119364 | −1.440267 | 1.299533 | 1.299533 | 1 | RA |
| 5.6888 | 0.377948 | 0.377948 | 4.703842 | 0.001244 | 0.08826 | −0.551533 | 1.299492 | 1.299492 | 1 | RA |
| 5.8806 | 0.377857 | 0.377857 | 5.484525 | 0.000447 | 0.067791 | 0.39556 | 1.29941 | 1.29941 | 1 | RA |
| 1.8516 | 0.374725 | 0.374725 | 5.431708 | 0.000478 | 0.067791 | 0.334755 | 1.296592 | 1.296592 | 1 | RA |
| 3.655 | 0.367548 | 0.367548 | 2.983814 | 0.016052 | 0.184597 | −2.978625 | 1.290159 | 1.290159 | 1 | RA |
| 2.5222 | 0.365318 | 0.365318 | 3.184975 | 0.01168 | 0.160965 | −2.676233 | 1.288166 | 1.288166 | 1 | RA |
| 2.1288 | 0.364614 | 0.364614 | 5.288952 | 0.000573 | 0.070842 | 0.168055 | 1.287537 | 1.287537 | 1 | RA |
| 3.2306 | 0.363046 | 0.363046 | 3.338237 | 0.009192 | 0.151385 | −2.447957 | 1.286139 | 1.286139 | 1 | RA |
| 5.2484 | 0.36296 | 0.36296 | 3.68495 | 0.0054 | 0.134402 | −1.940843 | 1.286062 | 1.286062 | 1 | RA |
| 2.7764 | 0.362854 | 0.362854 | 3.558769 | 0.006542 | 0.144805 | −2.123725 | 1.285967 | 1.285967 | 1 | RA |
| 2.8922 | 0.362136 | 0.362136 | 3.154388 | 0.012256 | 0.165143 | −2.722033 | 1.285327 | 1.285327 | 1 | RA |

TABLE 93

Example 1A. RA vs, healthy (HC)

| Probe sequence/ Probe location 60 mer | Chr | Start1 | End1 | Start2 | End2 |
|---|---|---|---|---|---|
| TATATAATTTCCACTTTGTTTTTAATAATCGAA ACATAACTGTTCTAAAATATGTCAAGT (SEQ ID NO: 104) | 3 | 112025277 | 112025306 | 112084449 | 112084478 |
| TGCTGAAAGAAAACACAATTTATTTAAGTCGA GACCATCCTAGCTAACACGGTGAAACCC (SEQ ID NO: 105) | 7 | 80173602 | 80173631 | 80200333 | 80200362 |
| GTTTTAACATTTAAAGATAAAATCCCCATCGAA CCCAGGGAGGCAGAGGTAGCAGTGAGC (SEQ ID NO: 106) | 10 | 98399261 | 98399290 | 98464394 | 98464423 |
| AGCTGATTGTGTAACTCTCAGTCTGAGCTCGAACCC AGGGAGGCAGAGGTAGCAGTGAGC (SEQ ID NO: 107) | 10 | 98397708 | 98397737 | 98461394 | 98464423 |
| GGGAAATAAATATTATGAAGCTTTAGTGTCGAACCC AGGGAGGCAGAGGTAGCAGTGAGC (SEQ ID NO: 108) | 10 | 98426248 | 98426277 | 98464394 | 98164423 |
| TACCAGGAAGATATTTTATAAATGAATGTCGAAGACA GTTTTGAGATTTGCTTTTCCTAG (SEQ ID NO: 109) | 5 | 7348280 | 7348309 | 7459586 | 7459615 |
| TAAGTGGGAGAAAAGACAAAGATTTCTCTCGAGGTG AGCGGATCACCTGAGGTCAGGAGT (SEQ ID NO: 110) | 1 | 167477867 | 167477896 | 167519448 | 167519477 |
| AGATCTTAAAGCAAGCTAAAAGAGCTATTCGAACCC AGGGAGGCAGAGGTAGCAGTGAGC (SEQ ID NO: 111) | 10 | 98413943 | 98413972 | 98464394 | 98464423 |
| TCTCCTTTTGGGCACATAGGACATAAAATCGAACC CAGGGAGGCAGAGGTAGCAGTGAGC (SEQ ID NO: 112) | 10 | 98406450 | 98406179 | 98464394 | 98464423 |

TABLE 93-continued

Example 1A. RA vs. healthy (HC)

| | | | | | |
|---|---|---|---|---|---|
| TTCATTCCCGCAAAAGGGTCATATATACTCGAACCC AGGGAGGCAGAGGTAGCAGTGAGC (SEQ ID NO: 113) | 10 | 98380248 | 98380277 | 98464394 | 98464423 |
| ATACTGACACACTATTCCACCCACAAAGTCGAACCC AGGGAGGCAGAGGTAGCAGTGAGC (SEQ ID NO: 114) | 10 | 98398985 | 98399014 | 98464394 | 98464423 |
| CTAATGTGCTAGTTTGTCCACATATTAATCGAGC CTGCAGTGAGCCATGATCATGCCACT (SEQ ID NO: 115) | 22 | 40993892 | 40993921 | 41008884 | 41008913 |
| TTCTTTCTTTAAGCTTTGCTTCTATCATTCGAGATA ATTTAGAATTAAGAAGGAATAAAC (SEQ ID NO: 116) | 5 | 7375992 | 7376021 | 7180988 | 7161017 |
| AGGTTTTGCCAAGTTGGCTGGGATGGTCTCGAGACC AGCCTGACCAACATGGAGAAACCC (SEQ ID NO: 117) | 22 | 40899405 | 40899434 | 41063868 | 41063897 |
| GGAACCAAACTGGAATTCAGGAGACAATTCGAACCC AGGGAGGCAGAGGTAGCAGTGAGC (SEQ ID NO: 118) | 10 | 98446149 | 98446178 | 98464394 | 98464423 |
| CACATTAACACCTGTCAATAAACAGGATTCGAACCCA GGGAGGCAGAGGTAGCAGTGAGC (SEQ ID NO: 119) | 10 | 98464394 | 98464423 | 98524128 | 98524157 |
| GTACAAAGAAGTGATGTAGCATGTCCTGTC GAACCCAGGGAGGCAGAGGTAGCAGTGAGC (SEQ ID NO: 120) | 10 | 98370157 | 98370186 | 98464394 | 98464423 |
| TATATAATTTCCACTTTGTTTTTAATAATCG AAGGACATATGATGGGTGTGGCTCGCCTG (SEQ ID NO: 121) | 3 | 112025277 | 112025306 | 112094417 | 112094446 |
| AGAAATGAGTCAGGTTCAATGAATTGTCTC GAGACCATCATGGCTAACACGGTGAAACCC (SEQ ID NO: 122) | 5 | 7402051 | 7402080 | 7612926 | 7612955 |
| CAAGTGGATGGGACACCCACCATGTCCCTCG AACCAGGGAGGCAGAGGTAGCAGTGAGC (SEQ ID NO: 123) | 10 | 98362078 | 98362107 | 98464394 | 98464423 |
| AATCTTTCATGAGGAGGCAATCAAGATGTC GACTGCTGTGCTAGCAATGAGCGAGGCTCC (SEQ ID NO: 124) | 11 | 93843497 | 93843526 | 93895631 | 93895660 |
| GAAGTCACCGTCGGCAGGTTCTGCTGCTTC GAACCCAGGGAGGCAGAGGTAGCAGTGAGC (SEQ ID NO: 125) | 10 | 98416601 | 98416630 | 98464394 | 98464423 |
| GTCAAACCTTTGAAAACTGCAGCTCCAGTCG ACTGCTGTGCTAGCAATGAGCGAGGCTCC (SEQ ID NO: 126) | 11 | 93843527 | 93843556 | 93895631 | 93895660 |
| GTTGTGACAATTTTCACAGAAGCGTTGTTCG AACCCAGGGAGGCAGAGGTAGCAGTGAGC (SEQ ID NO: 127) | 10 | 98442807 | 98442836 | 98464394 | 98464423 |
| AATGCTTATGTTCTAATTCCAAAAGGAATCG AGCCTGCAGTGAGCCATGATCATGCCACT (SEQ ID NO: 128) | 22 | 40876593 | 40876622 | 41008884 | 41008913 |
| GCTCTGTCAAGAAGACAGAGCAAGGTCTTCG AGCCTGCAGTGAGCCATGATCATGCCACT (SEQ ID NO: 129) | 22 | 40853643 | 40853672 | 41008884 | 41008913 |
| GGGTTTCACCGTGTTAGCCAGGATGGTCTCG AGACCATCCTGGCTAACATGGTGAAACCA (SEQ ID NO: 130) | 17 | 73323351 | 73323380 | 73395943 | 73395972 |
| ATATAAATTACATGTCAAGAAGATAATGTCG AGACCATCCTGACCAACATGGTGAAACCT (SEQ ID NO: 131) | 2 | 173590275 | 173590304 | 173791490 | 173791519 |

TABLE 93-continued

| Example 1A. RA vs, healthy (HC) | | | | | |
|---|---|---|---|---|---|
| CATGATAGTTAAGAGATCATATCTAGAATCG ATTCTCTATTTCATTTATTTCCACTGTAA (SEQ ID NO: 132) | X | 19753407 | 19753436 | 19779700 | 19779729 |
| GGGTTTCACCATATTGGCCAGGCTGGTCTCG AGACCAGCCTGGCCAACATGGTGAAACCC (SEQ ID NO: 133) | 22 | 40796445 | 40796474 | 40909403 | 40909432 |
| AGGTTTTGCCAAGTTGGCTGGGATGGTCTCG AGACCATCCTGGCCAACATGGTGAAACC (SEQ ID NO: 134) | 22 | 40899405 | 40899434 | 40935698 | 40935727 |
| GGCTGGCAGATCACCTAAGGTCAGGCATTCG AGAGCATGAAATAAAGACTTGTTAAGGCT (SEQ ID NO: 135) | 11 | 119101881 | 119101910 | 119157902 | 119157931 |
| GAGTGATTGTGGTTCCGAGGTCAGGAGGTC GACATATTTCCTGTTCCCTTGGAATAAAAA (SEQ ID NO: 136) | 7 | 55061796 | 55061825 | 55224589 | 55224618 |
| TCCAGGTACTTCTCTTAGCCTTATGGCTTCG ATGTGAGAGGCACTCTCTTTCACTAATAG (SEQ ID NO: 137) | 1 | 167399006 | 167399035 | 167415335 | 167415364 |
| GGTTTTCACCATGTTGGCCAGGATGGTCTC GAGACCAGCCTGGCCAACATGGTGAAACCC (SEQ ID NO: 138) | 22 | 40909403 | 40909432 | 40935698 | 40935727 |
| TTTATATTTTAAAAATTTGGGTTTTTTTTCG AGGCTGCAATGAGCCATGATCACACCACT (SEQ ID NO: 139) | 17 | 73352522 | 73352551 | 73430508 | 73430537 |
| TGCTGAAAGAAAACACAATTTATTTAAGTC GAATAAATGTGTGGCTATCTTACAGTGATT (SEQ ID NO: 140) | 7 | 80173602 | 80173631 | 80316977 | 80317006 |
| GGGTTTCACCATGTTAGCCAGGATGGTCTC GAGACCAGCCTGGCCAACATGGTGAAACCC (SEQ ID NO: 141) | 22 | 40909403 | 40909432 | 41079685 | 41079714 |
| GAGTTTCACCATGTTGACCAGGCTGGTCTC GAGATCAGCCTGGGCAACATGGTGAAACCC (SEQ ID NO: 142) | X | 19548269 | 19548298 | 19749247 | 19749276 |
| GGGAGGACTGGATCAGGAATCTGTGTCTTC GAACCCAGGGAGGCAGAGGTAGCAGTGAGC (SEQ ID NO: 143) | 10 | 98401434 | 98401463 | 98464394 | 98464423 |
| TACAACAATTAAGATATCACCTATATTCTCGA GACCATCCTAGCTAACATGGTGAAATCT (SEQ ID NO: 144) | 17 | 73347838 | 73347867 | 73428596 | 73428625 |
| GAGGGAAAAATACTAAGGCCACTAAAAATCG AGACCATCCTGGACAACATGGAGAAACAC (SEQ ID NO: 145) | X | 19650767 | 19650796 | 19925463 | 19925492 |
| GGGTTTTAACATATTGGCCAGGCTGGTCTCG AGACCAGCCTGGCCAATGTGGTGAAACCC (SEQ ID NO: 146) | 7 | 80078956 | 80078985 | 80121444 | 80121473 |
| GGATTTCACCATGTTGGCCAGGCTGGTCTCG AGACCAGCCTGGCCAACATGGTGAAACCC (SEQ ID NO: 147) | 22 | 40871340 | 40871369 | 40909403 | 40909432 |
| GTTTATTGCAGCATTGGCCTGTGGAGACTCG AGCCTGCAGTGAGCCATGATCATGCCACT (SEQ ID NO: 148) | 22 | 40888138 | 40888167 | 41008884 | 41008913 |
| AAACGGGACCAGCAGCGCTACTCAGGCCTC GACTGCTGTGCTAGCAATGAGCGAGGCTCC (SEQ ID NO: 149) | 11 | 93861558 | 93861587 | 93895631 | 93895660 |
| CCATGTTGGTCAGGCTGGTCTCAAACTCTCGA GACCAGCCTGGCCAACATGGTGAAACCC (SEQ ID NO: 150) | 22 | 40909403 | 40909432 | 41010689 | 41010718 |

TABLE 93-continued

| Example 1A. RA vs, healthy (HC) | | | | | |
|---|---|---|---|---|---|
| GGGTTTCTCCATGCTGGTCAGGCTGGTCTCG<br>AGACCAGCCTGGCCAACATGGTGAAACCC<br>(SEQ ID NO: 151) | | 22 | 40909403 | 40909432 | 40947045 | 40947074 |
| GGGTTTCGCCATGTTGGCCAGGCTGGTCTCG<br>AGACCAGCCTGGCCAACATGGTGAAACCC<br>(SEQ ID NO: 152) | | 17 | 73403615 | 73403644 | 73445695 | 73445724 |

| Probe sequence/ Probe location<br>60 mer | Chr | Start1 | End1 | Start2 | End2 |
|---|---|---|---|---|---|
| TATATAATTTCCACTTTGTTTTTAATAATCGAA<br>ACATAACTGTTCTAAAATATGTCAAGT<br>(SEQ ID NO: 104) | 3 | 112025277 | 112029276 | 112084449 | 112088448 |
| TGCTGAAAGAAAACACAATTTATTTAAGTCGA<br>GACCATCCTAGCTAACACGGTGAAACCC<br>(SEQ ID NO: 105) | 7 | 80169632 | 80173631 | 80196363 | 80200362 |
| GTTTTAACATTTAAAGATAAAATCCCCATCGAA<br>CCCAGGGAGGCAGAGGTAGCAGTGAGC<br>(SEQ ID NO: 106) | 10 | 98399261 | 98403260 | 98464394 | 98468393 |
| AGCTGATTGTGTAACTCTCAGTCTGAGCTCGAACCC<br>AGGGAGGCAGAGGTAGCAGTGAGC<br>(SEQ ID NO: 107) | 10 | 98397708 | 98401707 | 98464394 | 98468393 |
| GGGAAATAAATATTATGAAGCTTTAGTGTCGAACCC<br>AGGGAGGCAGAGGTAGCAGTGAGC<br>(SEQ ID NO: 108) | 10 | 98426248 | 98430247 | 98464394 | 98468343 |
| TACCAGGAAGATATTTTATAAATGAATGTCGAAGACA<br>GTTTTGAGATTTGCTTTTCCTAG<br>(SEQ ID NO: 109) | 5 | 7348280 | 7352279 | 7459586 | 7463585 |
| TAAGTGGGAGAAAAGACAAAGATTTCTCTCGAGGTG<br>AGCGGATCACCTGAGGTCAGGAGT<br>(SEQ ID NO: 110) | 1 | 167473897 | 167477968 | 167515784 | 167519477 |
| AGATCTTAAAGCAAGCTAAAAGAGCTATTCGAACCC<br>AGGGAGGCAGAGGTAGCAGTGAGC<br>(SEQ ID NO: 111) | 10 | 98413913 | 98417942 | 98464396 | 98468393 |
| TCTCCTTTTGGGCACATAGGACATAAAAATCGAACC<br>CAGGGAGGCAGAGGTAGCAGTGAGC<br>(SEQ ID NO: 112) | 10 | 98406450 | 98410449 | 98461394 | 98468393 |
| TTCATTCCCGCAAAAGGGTCATATATACTCGAACCC<br>AGGGAGGCAGAGGTAGCAGTGAGC<br>(SEQ ID NO: 113) | 10 | 98376278 | 98380277 | 98464394 | 98468393 |
| ATACTGACACACTATTCCACCCACAAAGTCGAACCC<br>AGGGAGGCAGAGGTAGCAGTGAGC<br>(SEQ ID NO: 114) | 10 | 98395015 | 98399014 | 98464394 | 98468393 |
| CTAATGTGCTAGTTTGTCCACATATTAATCGAGC<br>CTGCAGTGAGCCATGATCATGCCACT<br>(SEQ ID NO: 115) | 22 | 40989922 | 40993921 | 41008884 | 41012383 |
| TTCTTTCTTTAAGCTTTGCTTCTATCATTCGAGATA<br>ATTTAGAATTAAGAAGGAATAAAC<br>(SEQ ID NO: 116) | 5 | 7375992 | 7379991 | 7457018 | 7461017 |
| AGGTTTTGCCAAGTTGGCTGGGATGGTCTCGAGACC<br>AGCCTGACCAACATGGAGAAACCC<br>(SEQ ID NO: 117) | 22 | 40895435 | 40899434 | 41059898 | 41063897 |
| GGAACCAAACTGGAATTCAGGAGACAATTCGAACCC<br>AGGGAGGCAGAGGTAGCAGTGAGC<br>(SEQ ID NO: 118) | 10 | 98442179 | 98446178 | 98464394 | 98468393 |
| CACATTAACACCTGTCAATAAACAGGATTCGAACCCA<br>GGGAGGCAGAGGTAGCAGTGAGC<br>(SEQ ID NO: 119) | 10 | 98464394 | 98468393 | 98520158 | 98524157 |
| GTACAAAGAAGTGATGTAGCATGTCCTGTC<br>GAACCCAGGGAGGCAGAGGTAGCAGTGAGC<br>(SEQ ID NO: 120) | 10 | 98366187 | 98370186 | 98464394 | 98468393 |

TABLE 93-continued

| Example 1A. RA vs. healthy (HC) | | | | | |
|---|---|---|---|---|---|
| TATATAATTTCCACTTTGTTTTTAATAATCG AAGGACATATGATGGGTGTGGCTCGCCTG (SEQ ID NO: 121) | 3 | 112025277 | 112029276 | 112094417 | 112098416 |
| AGAAATGAGTCAGGTTCAATGAATTGTCTC GAGACCATCATGGCTAACACGGTGAAACCC (SEQ ID NO: 122) | 5 | 7402051 | 7406050 | 7612926 | 7616925 |
| CAAGTGGATGGGACACCCACCATGTCCCTCG AACCAGGGAGGCAGAGGTAGCAGTGAGC (SEQ ID NO: 123) | 10 | 98362078 | 98366077 | 98464394 | 98468393 |
| AATCTTTCATGAGGAGGCAATCAAGATGTC GACTGCTGTGCTAGCAATGAGCGAGGCTCC (SEQ ID NO: 124) | 11 | 93839527 | 93843526 | 93895631 | 93899630 |
| GAAGTCACCGTCGGCAGGTTCTGCTGCTTC GAACCCAGGGAGGCAGAGGTAGCAGTGAGC (SEQ ID NO: 125) | 10 | 98412631 | 98416630 | 98464394 | 98468393 |
| GTCAAACCTTTGAAAACTGCAGCTCCAGTCG ACTGCTGTGCTAGCAATGAGCGAGGCTCC (SEQ ID NO: 126) | 11 | 93843527 | 93847526 | 93895631 | 93899630 |
| GTTGTGACAATTTTCACAGAAGCGTTGTTCG AACCCAGGGAGGCAGAGGTAGCAGTGAGC (SEQ ID NO: 127) | 10 | 98442807 | 98446806 | 98464394 | 98468393 |
| AATGCTTATGTTCTAATTCCAAAAGGAATCG AGCCTGCAGTGAGCCATGATCATGCCACT (SEQ ID NO: 128) | 22 | 40872623 | 40876622 | 41008884 | 41012883 |
| GCTCTGTCAAGAAGACAGAGCAAGGTCTTCG AGCCTGCAGTGAGCCATGATCATGCCACT (SEQ ID NO: 129) | 22 | 40849673 | 40853672 | 41008884 | 4102883 |
| GGGTTTCACCGTGTTAGCCAGGATGGTCTCG AGACCATCCTGGCTAACATGGTGAAACCA (SEQ ID NO: 130) | 17 | 73319381 | 73323380 | 73391973 | 73395972 |
| ATATAAATTACATGTCAAGAAGATAATGTCG AGACCATCCTGACCAACATGGTGAAACCT (SEQ ID NO: 131) | 2 | 173586305 | 173590304 | 173787520 | 173791519 |
| CATGATAGTTAAGAGATCATATCTAGAATCG ATTCTCTATTTCATTTATTTCCACTGTAA (SEQ ID NO: 132) | X | 19753407 | 19757406 | 19775730 | 19779729 |
| GGGTTTCACCATATTGGCCAGGCTGGTCTCG AGACCAGCCTGGCCAACATGGTGAAACCC (SEQ ID NO: 133) | 22 | 40796445 | 40800444 | 40909403 | 40913402 |
| AGGTTTTGCCAAGTTGGCTGGGATGGTCTCG AGACCATCCTGGCCAACATGGTGAAACC (SEQ ID NO: 134) | 22 | 40895435 | 40899434 | 40931728 | 40935727 |
| GGCTGGCAGATCACCTAAGGTCAGGCATTCG AGAGCATGAAATAAAGACTTGTTAAGGCT (SEQ ID NO: 135) | 11 | 119097911 | 119101910 | 119157902 | 119161901 |
| GAGTGATTGTGGTTCCGAGGTCAGGAGGTC GACATATTTCCTGTTCCCTTGGAATAAAAA (SEQ ID NO: 136) | 7 | 55061796 | 55065795 | 55224589 | 55228588 |
| TCCAGGTACTTCTCTTAGCCTTATGGCTTCG ATGTGAGAGGCACTCTCTTTCACTAATAG (SEQ ID NO: 137) | 1 | 167399006 | 167403005 | 167411365 | 167415364 |
| GGTTTTCACCATGTTGGCCAGGATGGTCTC GAGACCAGCCTGGCCAACATGGTGAAACCC (SEQ ID NO: 138) | 22 | 40909403 | 40913402 | 40931728 | 40935727 |
| TTTATATTTTAAAAATTTGGGTTTTTTTCG AGGCTGCAATGAGCCATGATCACACCACT (SEQ ID NO: 139) | 17 | 73352522 | 73356521 | 73426538 | 73430537 |

TABLE 93-continued

| Example 1A. RA vs, healthy (HC) | | | | | |
|---|---|---|---|---|---|
| TGCTGAAAGAAAACACAATTTATTTAAGTC GAATAAATGTGTGGCTATCTTACAGTGATT (SEQ ID NO: 140) | 7 | 80169632 | 80173631 | 80313007 | 80317006 |
| GGGTTTCACCATGTTAGCCAGGATGGTCTC GAGACCAGCCTGGCCAACATGGTGAAACCC (SEQ ID NO: 141) | 22 | 40909403 | 40913402 | 41075715 | 41079714 |
| GAGTTTCACCATGTTGACCAGGCTGGTCTC GAGATCAGCCTGGGCAACATGGTGAAACCC (SEQ ID NO: 142) | X | 19544299 | 19548298 | 19745277 | 19749276 |
| GGGAGGACTGGATCAGGAATCTGTGTCTTC GAACCCAGGGAGGCAGAGGTAGCAGTGAGC (SEQ ID NO: 143) | 10 | 98401434 | 98405433 | 98464394 | 98468393 |
| TACAACAATTAAGATATCACCTATATTCTCGA GACCATCCTAGCTAACATGGTGAAATCT (SEQ ID NO: 144) | 17 | 73347838 | 73351837 | 73428596 | 73432595 |
| GAGGGAAAAATACTAAGGCCACTAAAAATCG AGACCATCCTGGACAACATGGAGAAACAC (SEQ ID NO: 145) | X | 19646797 | 19650796 | 19921493 | 19925492 |
| GGGTTTTAACATATTGGCCAGGCTGGTCTCG AGACCAGCCTGGCCAATGTGGTGAAACCC (SEQ ID NO: 146) | 7 | 80078956 | 80082955 | 80121444 | 80125443 |
| GGATTTCACCATGTTGGCCAGGCTGGTCTCG AGACCAGCCTGGCCAACATGGTGAAACCC (SEQ ID NO: 147) | 22 | 40871340 | 40875339 | 40909403 | 40913402 |
| GTTTATTGCAGCATTGGCCTGTGGAGACTCG AGCCTGCAGTGAGCCATGATCATGCCACT (SEQ ID NO: 148) | 22 | 40888138 | 40892137 | 41008884 | 41012883 |
| AAACGGGACCAGCAGCGCTACTCAGGCCTC GACTGCTGTGCTAGCAATGAGCGAGGCTCC (SEQ ID NO: 149) | 11 | 93857588 | 93861587 | 93895631 | 93899630 |
| CCATGTTGGTCAGGCTGGTCTCAAACTCTCGA GACCAGCCTGGCCAACATGGTGAAACCC (SEQ ID NO: 150) | 22 | 40909403 | 40913402 | 41006719 | 41010718 |
| GGGTTTCTCCATGCTGGTCAGGCTGGTCTCG AGACCAGCCTGGCCAACATGGTGAAACCC (SEQ ID NO: 151) | 22 | 40909403 | 40913402 | 40943075 | 40947074 |
| GGGTTTCGCCATGTTGGCCAGGCTGGTCTCG AGACCAGCCTGGCCAACATGGTGAAACCC (SEQ ID NO: 152) | 17 | 73399645 | 73403644 | 73441725 | 73445724 |

The invention claimed is:

1. A method of selecting a human subject and treating the selected human subject, wherein the selected human subject is responsive to a specific therapy for rheumatoid arthritis and is in need of therapy for rheumatoid arthritis, and wherein the method comprises detecting the presence or absence of a first, second, third, fourth and fifth chromosomal interaction in a sample from the human subject, wherein selecting the human subject as responsive to the specific therapy is based on detection of:

the absence of a first chromosomal interaction,
the presence of a second chromosomal interaction,
the absence of a third chromosomal interaction,
the presence of a fourth chromosomal interaction, and
the presence of a fifth chromosomal interaction;

and treating the selected human subject for rheumatoid arthritis by administering to the selected human subject the specific therapy, wherein said detecting is carried out by (a) cross-linking of chromosome regions in the sample from the human subject which have come together in a chromosome interaction;

(b) subjecting said cross-linked regions to cleavage;

(c) ligating said cross-linked cleaved DNA ends to form ligated nucleic acids; and (d) detecting the presence or absence of the ligated nucleic acids to thereby detect whether regions have been brought together in a chromosome interaction;

wherein:

the first chromosomal interaction is on chromosome 4 in the CXCL13 gene and the ligated nucleic acid corresponding to the first chromosomal interaction is detected by the probe sequence: TTATATCTCCTACCTCCAAGCCTGGCAGTCGATTCCAAAGTGAAGCAAAAAAAAAAC TTC (SEQ ID NO: 99), the second chromosomal interaction is on chromosome 21 in the IFNAR1 gene and the ligated nucleic acid corresponding to the second chromosomal interaction is detected by the probe sequence: GTGCAGAGCGAGAGCGGGGCAGAGGCGGTCGAAACTGGGAGAATTCATCTGAAAT GATTA (SEQ ID NO: 75), the third chromosomal interaction is on chromosome 6 in the IL-17A gene and the ligated nucleic acid corresponding to the third chromosomal interaction is detected by the probe sequence: CCCTCCCTCAACATGCAGGGATTACAATTCGAAGATGGTCTGAAGGAAGCAATTGG GAAA (SEQ ID NO: 103), the fourth chromosomal interaction is on chromosome 16 in the IL-21R gene and the ligated nucleic acid corresponding to the fourth chromosomal interaction is detected by the probe sequence: GAGGCAGGCAGATCATGAGGTCAGGAGTTCGAGCCCTGGACCCCAGGCCAGCTAAT GAGG (SEQ ID NO: 76), and the fifth chromosomal interaction is on chromosome 12 in the IL-23 gene and the ligated nucleic acid corresponding to the fifth chromosomal interaction is detected by the probe sequence: AGTGGCATGATCACAGCTCACTGCCACCTCGAAACCAAACCCTGTGACTTCAACACC CAA (SEQ ID NO: 102), and wherein the specific therapy comprises methotrexate or a pharmaceutically acceptable salt thereof.

* * * * *